United States Patent
Barany et al.

(10) Patent No.: US 10,011,862 B2
(45) Date of Patent: Jul. 3, 2018

(54) METHOD FOR RELATIVE QUANTIFICATION OF CHANGES IN DNA METHYLATION, USING COMBINED NUCLEASE, LIGATION, AND POLYMERASE REACTIONS

(71) Applicant: CORNELL UNIVERSITY, Ithaca, NY (US)

(72) Inventors: Francis Barany, New York, NY (US); Eugene Spier, Los Altos, CA (US)

(73) Assignee: Cornell University, Ithaca, NY (US)

(*) Notice: Subject to any disclaimer, the term of this patent is extended or adjusted under 35 U.S.C. 154(b) by 140 days.

(21) Appl. No.: 14/775,876

(22) PCT Filed: Mar. 13, 2014

(86) PCT No.: PCT/US2014/026027
§ 371 (c)(1),
(2) Date: Dec. 21, 2015

(87) PCT Pub. No.: WO2014/160199
PCT Pub. Date: Oct. 2, 2014

(65) Prior Publication Data
US 2016/0032357 A1 Feb. 4, 2016

Related U.S. Application Data

(66) Substitute for application No. 61/783,657, filed on Mar. 14, 2013.

(51) Int. Cl.
*C12Q 1/68* (2018.01)
*C12Q 1/683* (2018.01)
*C12Q 1/6858* (2018.01)
*C12Q 1/6886* (2018.01)

(52) U.S. Cl.
CPC ........... *C12Q 1/683* (2013.01); *C12Q 1/6858* (2013.01); *C12Q 1/6886* (2013.01); *C12Q 2600/154* (2013.01)

(58) Field of Classification Search
None
See application file for complete search history.

(56) References Cited

U.S. PATENT DOCUMENTS

| 7,358,048 B2 | 4/2008 | Barany et al. |
| 7,459,274 B2 | 12/2008 | Lakey et al. |
| 2007/0092883 A1 | 4/2007 | Schouten et al. |
| 2011/0212846 A1* | 9/2011 | Spier ............ C12Q 1/686 506/7 |

FOREIGN PATENT DOCUMENTS

| WO | 0026401 A1 | 5/2000 |
| WO | 2005040399 A2 | 5/2005 |
| WO | 2006088978 A1 | 8/2006 |

OTHER PUBLICATIONS

Supplementary European Search Report for Corresponding European Patent Application No. 14773880.1 (dated Sep. 28, 2016).
Khulan et al., "Comparative Isoschizomer Profiling of Cytosine Methylation: The HELP Assay," Genome Research 16(8):1046-1055 (2006).
Tong et al., "Detection of Restriction Enzyme-Digested Target DNA by PCR Amplification Using A Stem-Loop Primer: Application to the Detection of Hypomethylated Fetal DNA in Maternal Plasma," Clinical Chemistry 53(11):1906-1914.
International Search Report and Written Opinon for corresponding application No. PCT/US14/26027 dated Jul. 29, 2014.
Examination Report for EP14773880.1 dated Jul. 11, 2017.

* cited by examiner

*Primary Examiner* — James Martinell
(74) *Attorney, Agent, or Firm* — LeClairRyan PLLC

(57) ABSTRACT

The present invention is directed to methods for identifying the presence of one or more methylated or unmethylated target nucleotide sequences in a sample that involve a nuclease-ligation reaction. In some embodiments, the ligation products formed in the nuclease-ligation process of the present invention are subsequently amplified using a polymerase chain reaction. The ligated product sequences or extension products thereof are detected, and the presence of one or more methylated or unmethylated target nucleotide sequences in the sample is identified based on the detection.

25 Claims, 16 Drawing Sheets

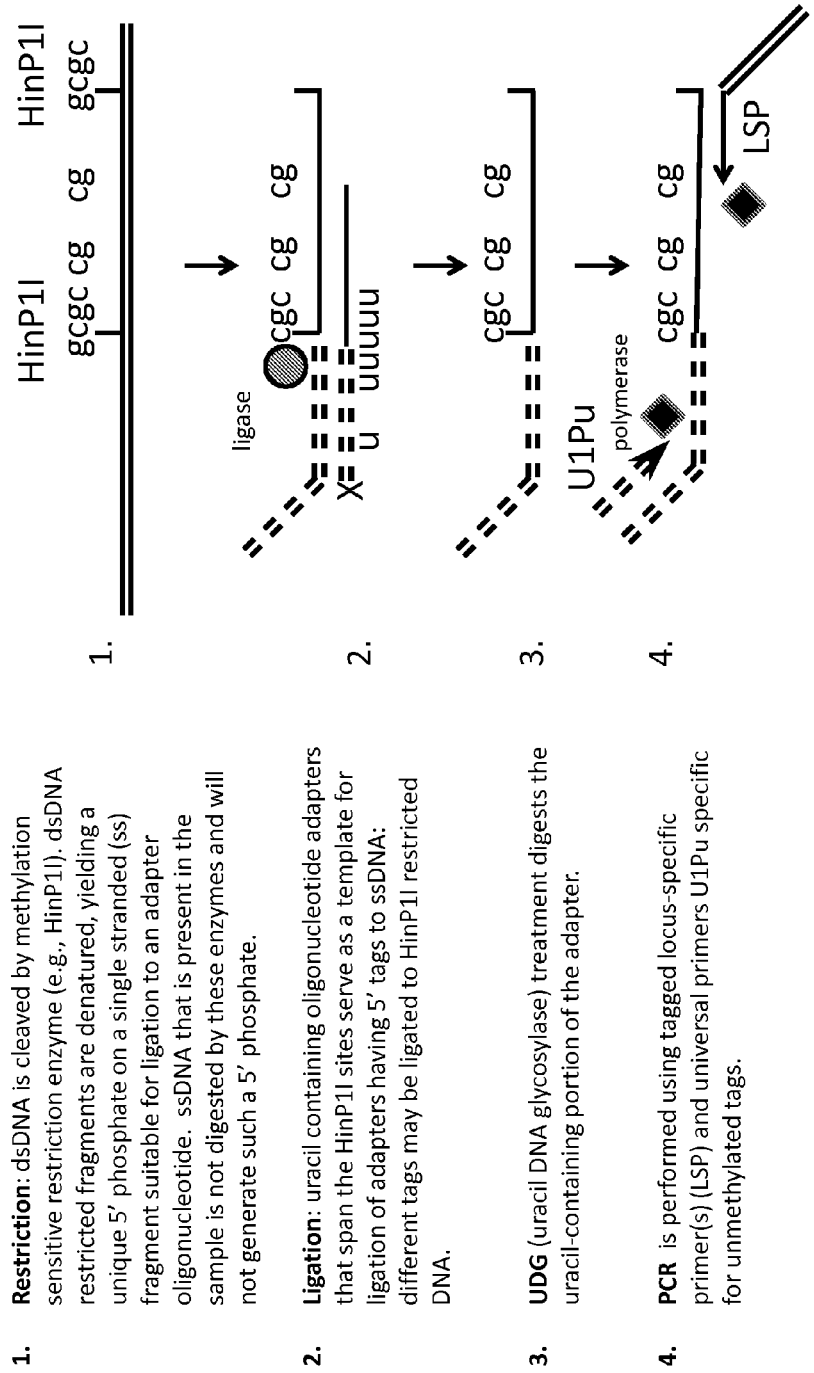

Figure 1A

1. Restriction: dsDNA is cleaved by methylation sensitive restriction enzyme (e.g., HinP1I), dsDNA restricted fragments are denatured, yielding a unique 5' phosphate on a single stranded (ss) fragment suitable for ligation to an adapter oligonucleotide. ssDNA that is present in the sample is not digested by these enzymes and will not generate such a 5' phosphate.

2. Ligation: uracil containing oligonucleotide adapters that span the HinP1I sites serve as a template for ligation of adapters having 5' tags to ssDNA: different tags may be ligated to HinP1I restricted DNA.

3. UDG (uracil DNA glycosylase) treatment digests the uracil-containing portion of the adapter.

4. PCR is performed using tagged locus-specific primer(s) (LSP) and universal primers U1Pu specific for unmethylated tags.

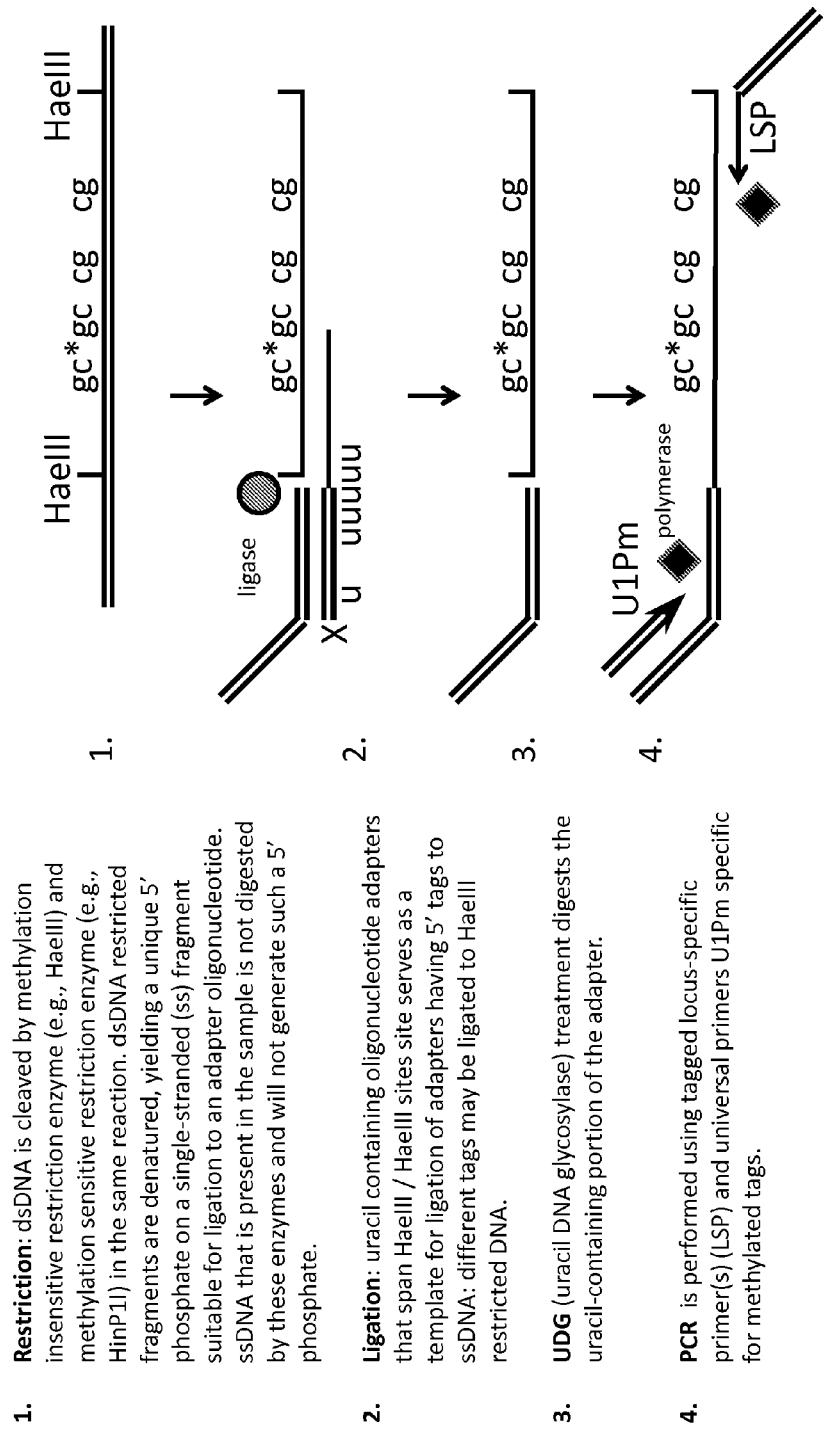

Figure 1B

1. Restriction: dsDNA is cleaved by methylation insensitive restriction enzyme (e.g., HaeIII) and methylation sensitive restriction enzyme (e.g., HinP1I) in the same reaction. dsDNA restricted fragments are denatured, yielding a unique 5' phosphate on a single-stranded (ss) fragment suitable for ligation to an adapter oligonucleotide. ssDNA that is present in the sample is not digested by these enzymes and will not generate such a 5' phosphate.

2. Ligation: uracil containing oligonucleotide adapters that span HaeIII / HaeIII sites site serves as a template for ligation of adapters having 5' tags to ssDNA: different tags may be ligated to HaeIII restricted DNA.

3. UDG (uracil DNA glycosylase) treatment digests the uracil-containing portion of the adapter.

4. PCR is performed using tagged locus-specific primer(s) (LSP) and universal primers U1Pm specific for methylated tags.

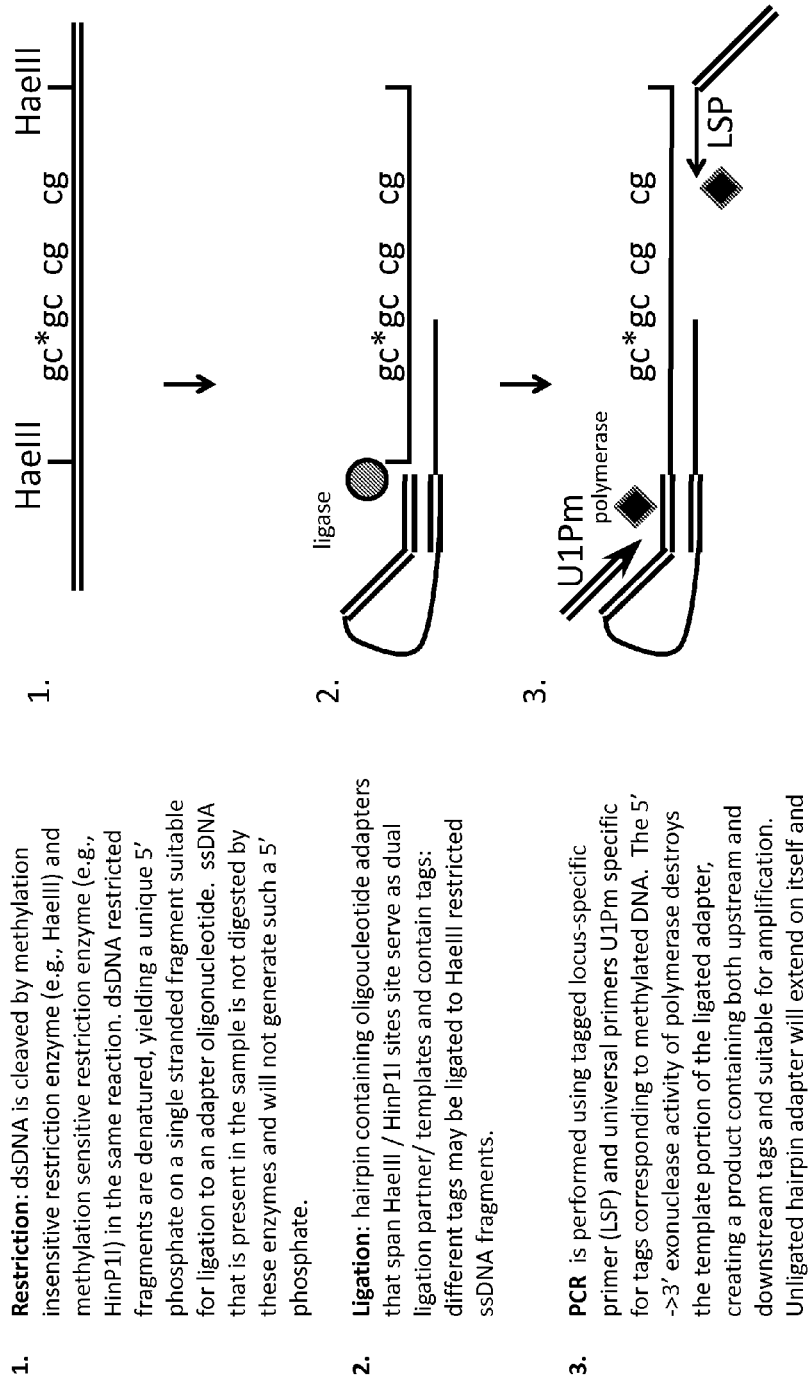

1. Restriction: dsDNA is cleaved by methylation insensitive restriction enzyme (e.g., HaeIII) and methylation sensitive restriction enzyme (e.g., HinP1I) in the same reaction. dsDNA restricted fragments are denatured, yielding a unique 5' phosphate on a single stranded fragment suitable for ligation to an adapter oligonucleotide. ssDNA that is present in the sample is not digested by these enzymes and will not generate such a 5' phosphate.

2. Ligation: hairpin containing oligoucleotide adapters that span HaeIII / HinP1I sites site serve as dual ligation partner/ templates and contain tags: different tags may be ligated to HaeIII restricted ssDNA fragments.

3. PCR is performed using tagged locus-specific primer (LSP) and universal primers U1Pm specific for tags corresponding to methylated DNA. The 5' ->3' exonuclease activity of polymerase destroys the template portion of the ligated adapter, creating a product containing both upstream and downstream tags and suitable for amplification. Unligated hairpin adapter will extend on itself and not amplify further.

Figure 2B

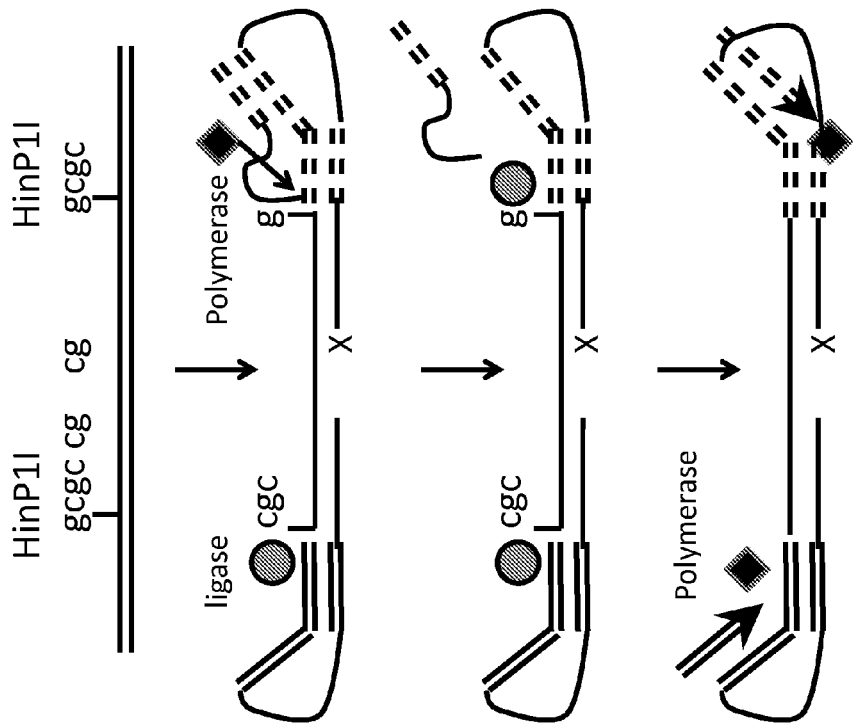

1. Restriction digest using methylation-sensitive enzyme, e.g., HinP1I. Only unmethylated DNA is restricted.

2. Ligation of hairpin containing adapters that span HinP1I sites serve as dual ligation partner/ templates and contain different tags. The downstream ligation adapter has a 5' tail that is cleaved off by the 5'→3' activity of Taq polymerase when hybridized to the digestion product, but uncleaved adapter hybridizes back to the Universal Primer U2' region such that it inhibits subsequent priming of the unligated adapter.

3. PCR using universal primers detects only DNA where both sites are unmethylated. The 5'→3' exonuclease activity of polymerase destroys the template portion of both ligated oligonucleotide adapters, creating a product containing both upstream and downstream tags and suitable for amplification. Unligated upstream adapters extend on themselves and are not amplified.

Figure 9B

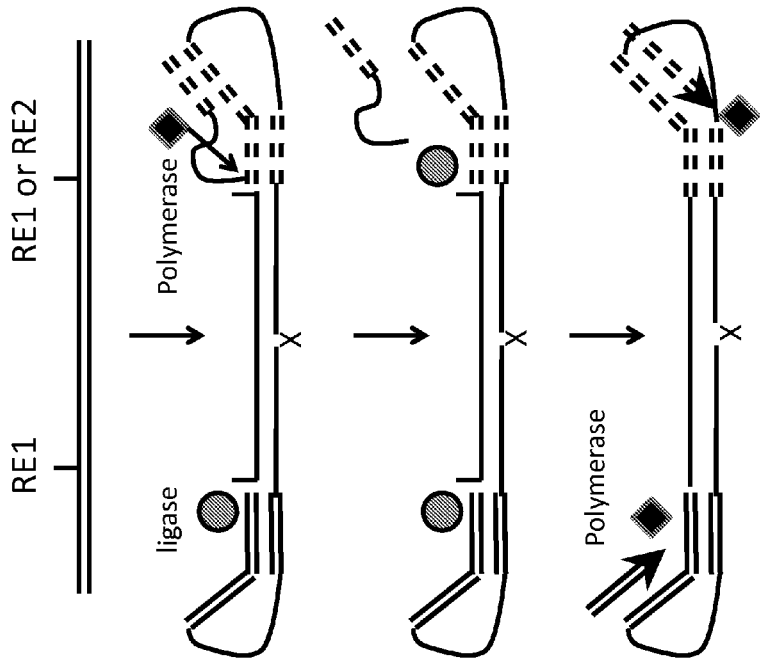

Figure 9C

1. Restriction Endonuclease (RE) digest using: (i) Methyl-insensitive enzyme(s) to form fragment, with at least one internal methyl sensitive sites, to select for methylated DNA, and/or (ii) Methylation-sensitive enzyme(s), to select for unmethylated DNA.

2. Ligation of hairpin containing coupled oligonucleotide adapters that span RE sites serve as dual ligation partner/ templates and contain different tags. The downstream ligation oligonucleotide adapter has a 5' tail that is cleaved off by the 5'→3' activity of Taq polymerase when hybridized to a digestion product, but uncleaved adapter hybridizes back to the Universal Primer U2' region such that it inhibits priming of the unligated adapter.

3. PCR using universal primers detects only DNA where both sites are unmethylated. The 5'→3' exonuclease activity of polymerase destroys the template portion of ligated adapters, creating a product containing both upstream and downstream tags and suitable for amplification. Unligated upstream hairpin extends on itself till block (X) and is not amplified.

METHOD FOR RELATIVE QUANTIFICATION OF CHANGES IN DNA METHYLATION, USING COMBINED NUCLEASE, LIGATION, AND POLYMERASE REACTIONS

This application is a national stage application under 35 U.S.C. § 371 of PCT International Application No. PCT/US14/26027, filed Mar. 13, 2014, which claims the benefit of U.S. Provisional patent application Ser. No. 61/783,657, filed Mar. 14, 2013, which is hereby incorporated by reference in its entirety.

FIELD OF THE INVENTION

The present invention relates to a method for relative quantification of changes in DNA methylation using combined nuclease, ligation, and polymerase reactions.

BACKGROUND OF THE INVENTION

Cancers contain altered methylation patterns that result in aberrant expression of critical genes. Hypermethylation turns off expression of genes required to regulate normal growth while hypomethylation allows for inappropriate expression of genes that allow cells to proliferate. Promoters for genes often have regions of high CpG content known as "CpG Islands". When genes, such as tumor suppressor genes with promoter CpG islands, are turned off, this is usually accompanied with methylation of most CpG sequences within the promoter and first intron regions. Aberrant promoter hypermethylation occurs at the 5-position of cytosine within the CpG dinucleotide. (Gardiner-Garden et al., *J. Mol. Biol.*, 196(2): 261-82 (1987)). It inactivates the expression of critical genes that are involved in tumor suppression, DNA repair, control of tumor metastasis, and invasion (Cheng et al., Genome Res. 16(2): 282-89 (2005), Feinberg et al., *Nature*, 301: 89-92 (1983); Jones et al., *Nat. Rev. Genet.*, 3(6): 415-28 (2002)). There is a great need in both basic and clinical research to identify promoter DNA methylation status with high efficiency and accuracy for disease diagnoses and prognoses.

The presence and absence of methylation in certain genetic regions has prenatal diagnostic and prognostic applications. For example, aberrant methylation on regions on chromosomes 13, 18, 21, X, and Y can be used to diagnose Down syndrome (Patsalis et al., *Exp. Opin. Biol. Ther.* 12(Suppl. 1): S155-S161 (2012). Because fetal DNA and maternal DNA are differentially methylated, cell-free DNA in maternal plasma can provide a source of fetal DNA, which can be obtained non-invasively and utilized to assess the methylation state of the aforementioned chromosomes.

Currently, a number of groups use bisulfite approaches to detect the presence of low levels of methylated DNA in serum, as a marker of early cancer (deVos, *Clinical Chemistry* 55(7):1337-1346 (2009), Lind et al., *Molecular Cancer* 10:85 (2011)). However, often a single marker gives unacceptably high false-positive and false-negative results (Alquist et al., *Clin. Gastroenterol. Hepatol.* 10(3): 272-277 (2012)). Thus, a single or a few methylation markers is insufficient for robust detection of early cancer from the serum. There is an urgent need for methods with multiplexed detection of very low levels of methylated DNA when the majority of DNA with the same sequence is unmethylated. For example, detection of multiple methylated DNA sequences in cell-free DNA isolated from serum may enable early detection of cancer. Likewise, methods for multiplexed detection of very low levels of unmethylated DNA when the majority of DNA with the same sequence is methylated are also urgently needed for applications such as early detection of cancer.

Various methods have been developed for the study of promoter DNA methylation status of known genes (Laird P. W., *Nature Review Cancer*, 3: 253-266 (2003)). These methods can generally be grouped into two categories: methylation-sensitive restriction endonuclease assays and sodium bisulfite conversion based approaches.

Methylation-Sensitive Restriction Endonuclease Digestion Methods:

This approach takes advantage of methyl-sensitive restriction enzymes, wherein genomic DNA is cleaved when unmethylated, and this is followed by a PCR amplification using primers that flank the site(s) (Singer-Sam et al., *Nucleic Acids Res.*, 18(3): 687 (1990), Singer-Sam et al., *Mol. Cell. Biol.*, 10(9): 4987-9 (1990)). A methylated restriction endonuclease site results in the presence of the proper PCR product. The credibility of this method depends on the complete digestion of unmethylated DNA by the restriction endonuclease. This problem is exacerbated by: (i) limiting amounts of methylated DNA in the sample, (ii) the requirement of some restriction enzymes to bind two unmethylated sites simultaneously, and (iii) the lack of, or poor activity of restriction enzymes to single-stranded DNA that may arise during sample preparation. It is difficult to drive endonuclease digestions to completion. Thus, it is sometimes difficult to determine whether PCR amplicons result from incomplete digestion (i.e. false positives) or from those of low abundance methylation sites (i.e. true positives). Restriction enzyme techniques are based on removing the unmethylated DNA, and assuming that PCR amplification of the remaining DNA arises because it was methylated, and consequently the method is susceptible to false positives arising from incomplete removal of unmethylated DNA. This technique has the disadvantage that it is not accurate for finding low levels of methylated DNA when the majority of the same sequence is unmethylated, as would be the case with detection of cancer-associated methylation at multiple markers in cell free DNA from the serum.

Sodium-Bisulfite-Based Chemical Conversion.

Chemical conversion of cytosines to uracils using bisulfite can be used to detect DNA methylation differences. 5-methylcytosines are resistant to conversion, and deamination only occurs on unmethylated cytosines (Frommer et al., *Proc. Natl. Acad. Sci. USA*, 89(5): 1827-31 (1992)). Bisulfite can be quantitatively added to the 5-6 double bonds of cytosine if there is no methyl group on the 5 position. Bisulfite addition renders the cytosine susceptible to hydrolytic deamination; subsequent elimination of the bisulfite results in the formation of uracil (Voss et al., *Anal. Chem.*, 70(18): 3818-3823 (1998)). One strand of the modified DNA sequences can then be PCR amplified and sequenced. However, due to stromal cell contamination in a typical clinical sample, direct sequencing without cloning the PCR products reduces the sensitivity of the technique. It requires about 25% of the alleles to be methylated for accurate detection (Myohanen et al., *DNA Sequence*, 5: 1-8 (1994).

Development of methylation-specific PCR (MSP) has allowed the sensitive and specific study of low abundance methylation sequences (Herman et al., *Proc. Natl. Acad. Sci. USA*, 93(18): 9821-6 (1996)). MSP relies upon chemical modification of DNA using bisulfite, and specifically designed PCR primers that are complementary to the bisulfite modified DNA template. Typically, more than three CpG sites have to be included in the oligonucleotide sequences. Two sets of MSP PCR primers are designed, one set of the MSP primers has the sequence to perfectly hybridize to the complementary strand of the bisulfite-treated methylated DNA sequence with methyl-cytosines residing on the CpG sites. The other set of the MSP primers is only designed to perfectly hybridize to the complementary strand of the bisulfite-treated DNA sequence in the absence of methylated cytosine. Consequently, the MSP specific PCR products only results from the DNA template which contains methyl-cytosines.

There are three major difficulties with this approach. The design of MSP primers requires sufficient numbers of methylated cytosines to be present in the primer sequence to ensure the selection capability. It may not be sufficiently sensitive to distinguish partial methylated sequences from fully methylated one. In addition, this assay analyzes one gene at a time, and both sets of MSP primers have different annealing temperatures which may further slowdown its throughput. Finally, bisulfite treatment of DNA often nicks the DNA (i.e. destroys the backbone chain) as it is also converting unmethylated cytosines to uracil. Conditions which assure that all unmethylated cytosines are converted to uracil may also destroy the DNA. Conditions which assure that sufficient DNA remains intact may not assure that all unmethylated cytosines are converted to uracil. Thus, absence of a band may be the consequence of destroying too much of the starting DNA and, consequently, insufficient amplification, leading to a false negative result. Likewise, presence of a band may be the consequence of incomplete conversion of unmethylated cytosine to uracil, allowing for primer binding at an unmethylated site, and leading to a false positive result. Some of these problems may be overcome by combining the use of Bisulfite treatment, the polymerase chain reaction, and the ligase detection reaction (see U.S. Pat. No. 7,358,048 to Barany et al.)

A further improvement of this technique employs a blocking oligonucleotide that hybridizes to the sequence for bisulfite-converted unmethylated DNA, thus enriching for amplification of bisulfite-converted methylated DNA (deVos et al., *Clinical Chemistry* 55(7):1337-1346 (2009)). The disadvantage is that bisulfite treatment destroys from 50% to 90% of the original DNA integrity by nicking it. When starting with DNA from the serum (with average length of about 160 bases), this can be a significant problem. Further, converting C's to U's reduces the complexity of the sequence from 4 bases to 3 bases. Thus, non-specific amplifications can occur. This usually necessitates a nested-PCR approach; this runs the risk of carryover contamination and is generally not ideal for multiplexed amplifications.

The present invention is directed at overcoming this and other deficiencies in the art.

SUMMARY OF THE INVENTION

A first aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues and subjecting the one or more target nucleic acid molecules in the sample to at least one methylation insensitive enzyme digestion reaction and at least one methylation sensitive enzyme digestion reaction to form a plurality of digestion products. A plurality of oligonucleotide adapters are provided, each oligonucleotide adapter comprising a first primer-specific portion and a 3' end, said 3' end being configured to ligate to a 5' portion of a digestion product and hybridized to its complement, wherein the complement of the 3' end is coupled to a region complementary to a 5' portion of a digestion product. The digestion products are subjected to a ligation reaction comprising a denaturation treatment to form single-stranded digestion products, a hybridization treatment, wherein the single-stranded digestion products hybridize to their complementary region of the oligonucleotide adapters in a sequence-specific manner such that the 3' end of the adapter is adjacent to the 5' end of the single-stranded digestion product, and ligation treatment, wherein the oligonucleotide adapters ligate to their hybridized single-stranded digestion products thereby forming adapter tagged digestion products. The method further involves providing one or more primary oligonucleotide primer sets, each primary primer set comprising (i) a first primary oligonucleotide primer having a nucleotide sequence that is the same as the first primer specific portion of the adapter tagged digestion products, and (ii) a second primary oligonucleotide primer comprising a nucleotide sequence that is complementary to a region of the digestion product that is 3' of one or more methylated, uncleaved restriction sites, and a second primer-specific portion. The plurality of adapter tagged digestion products, the one or more primary oligonucleotide primer sets, and a first polymerase are blended to form a first polymerase chain reaction mixture, and the first polymerase chain reaction mixture is subjected to one or more polymerase chain reaction cycles comprising a denaturation treatment, a hybridization treatment, and an extension treatment thereby forming primary extension products. The primary extension products are detected and distinguished, thereby identifying the presence of one or more target nucleic acid molecules differing from other nucleic acid molecules in the sample by one or more methylated residues.

Another aspect of the present invention is directed to a method for identifying, in a sample, one or more target nucleic acid molecules differing from other nucleic acid molecules in the sample by one or more unmethylated residues. This method involves providing a sample containing one or more target nucleic acid molecules potentially containing one or more unmethylated residues and subjecting the one or more target nucleic acid molecules in the sample to at least one methylation sensitive enzyme digestion reaction to form a plurality of digestion products comprising one or more unmethylated residues. A plurality of oligonucleotide adapters are provided, each oligonucleotide adapter comprising a first primer-specific portion and a 3' end, said 3' end being configured to ligate to a 5' portion of a digestion product and hybridized to its complement, wherein the complement of the 3' end is coupled to a region complementary to a 5' portion of a digestion product. The digestion products are subject to a ligation reaction comprising a denaturation treatment to form single-stranded digestion products, a hybridization treatment, wherein the single-stranded digestion products hybridize to their complementary region of the oligonucleotide adapters in a sequence-specific manner such that the 3' end of the adapter is adjacent to the 5' end of the single-stranded digestion product, and ligation treatment, wherein the oligonucleotide adapters ligate to their hybridized single-stranded digestion products thereby forming adapter tagged digestion products. The method further involves providing one or more primary oligonucleotide primer sets, each primary primer set comprising (i) a first primary oligonucleotide primer comprising a nucleotide sequence that is the same as the first primer specific portion of the adapter tagged digestion products and (ii) a second primary oligonucleotide primer comprising a nucleotide sequence that is complementary to a region of the digestion product, and a second primer-specific portion. The plurality of adapter tagged digestion products, the one or more primary oligonucleotide primer sets, and a first polymerase are blended to form a first polymerase chain reaction mixture, and the first polymerase chain reaction mixture is subjected to one or more polymerase chain reaction cycles comprising a denaturation treatment, a hybridization treatment, and an extension treatment thereby forming primary extension products. The primary extension products are detected and distinguished, thereby identifying the presence of one or more target nucleic acid molecules differing from other nucleic acid molecules in the sample by one or more unmethylated residues.

Another aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues, and subjecting the one or more target nucleic acid molecules in the sample to at least one methylation insensitive enzyme digestion reaction and at least one methylation sensitive enzyme digestion reaction to form a plurality of digestion products comprising one or more methylated uncleaved restriction sites. A plurality of oligonucleotide adapter sets are provided, each oligonucleotide adapter set comprising (a) a first oligonucleotide adapter having a 3' end configured to ligate to a 5' end of a digestion product and hybridized to its complement, wherein the complement of the 3' end is coupled to a region complementary to a 5' portion of a digestion product and (b) a second oligonucleotide adapter having a 5' end configured to ligate to a 3' end of a digestion product and hybridized to its complement, wherein the complement of the 5' end is coupled to a region complementary to a 3' portion of a digestion product. The digestion products are subject to a ligation reaction comprising a denaturation treatment to form single-stranded digestion products, a hybridization treatment, wherein the single-stranded digestion products hybridize to their complementary regions of the first and second oligonucleotide adapters of an oligonucleotide adapter set in a sequence-specific manner such that the 3' end of the first adapter is adjacent to the 5' end of the single-stranded digestion product and the 5' end of the second adapter is adjacent to the 3' end of the single-stranded digestion product, and a ligation treatment, wherein the oligonucleotide adapters ligate to their hybridized single-stranded digestion products thereby forming dual adapter tagged digestion products. The dual adapter tagged digestion products are detected, thereby identifying one or more target nucleic acid molecules differing from other nucleic acid molecules in the sample by one or more methylated residues.

Another aspect of the present invention is directed to a method for identifying, in a sample, one or more target nucleic acid molecules differing from other nucleic acid molecules in the sample by one or more unmethylated residues. This method involves providing a sample containing one or more target nucleic acid molecules potentially containing one or more unmethylated residues and subjecting the one or more target nucleic acid molecules in the sample to a methylation sensitive enzyme digestion that digests unmethylated, but not methylated nucleic acid molecules to form a plurality of digestion products comprising one or more unmethylated residues. A plurality of oligonucleotide adapter sets are provided, each oligonucleotide adapter set comprising (a) a first oligonucleotide adapter having a 3' end configured to ligate to a 5' end of a digestion product and hybridized to its complement, wherein the complement of the 3' end is coupled to a region complementary to a 5' portion of a digestion product and (b) a second oligonucleotide adapter having a 5' end configured to ligate to a 3' end of a digestion product and hybridized to its complement, wherein the complement of a 5' end is coupled to a region complementary to the 3' portion of a digestion product. The digestion products are subjected to a ligation reaction comprising a denaturation treatment to form single-stranded digestion products, a hybridization treatment, wherein the single-stranded digestion products hybridize to their complementary regions of the first and second oligonucleotide adapters of an oligonucleotide adapter set in a sequence-specific manner such that the 3' end of the first adapter is adjacent to the 5' end of the single-stranded digestion product and the 5' end of the second adapter is adjacent to the 3' end of the single-stranded digestion product, and a ligation treatment, wherein the oligonucleotide adapters ligate to their hybridized single-stranded digestion products thereby forming dual adapter tagged digestion products. The dual adapter tagged digestion products are detected, thereby identifying one or more target nucleic acid molecules differing from other nucleic acid molecules in the sample by one or more unmethylated residues.

The above-described methods for detecting methylated residues in target nucleic acid molecule have multiple levels of discrimination allowing for the highest levels of sensitivity and specificity, even when trying to detect low-abundance methylated target nucleic acid molecules.

When using a single oligonucleotide adapter approach, these levels of discrimination include: (i) use of methylation insensitive restriction enzyme to generate a unique ligation competent 5' phosphate on double-stranded target nucleic acid molecules, (ii) use of methylation sensitive restriction enzymes to cleave double-stranded target nucleic acid molecules when not methylated, (iii) use of ligation fidelity of thermostable ligase to ligate correct oligonucleotide adapter to digested target nucleic acid molecule, (iv) use of locus specific oligonucleotide primer and polymerase to amplify adapter tagged target nucleic acid molecules, and (v) use of sequences on the 3' end of oligonucleotide adapter, such that when they are not ligated to the target nucleic acid molecules, they form hairpins and extend on themselves to form products that do not amplify and are not detected.

When using a dual adapter approach, these levels of discrimination include: (i) use of methylation insensitive restriction enzyme to generate unique ligation competent 5' phosphate and 3' OH on double-stranded target nucleic acid molecules, (ii) use of methylation sensitive restriction enzymes to cleave double-stranded target nucleic acid molecules when not methylated, (iii) use of ligation fidelity of thermostable ligase to ligate correct oligonucleotide adapters to target nucleic acid molecules, (iv) use of 5'→3' nuclease activity of polymerase or Fen nuclease on downstream oligonucleotide adapter, and (v) use of sequences on both the 3' and 5' ends of oligonucleotide adapters, such that when they are not ligated to the target nucleic acid molecules, they form hairpins to prevent primer binding, or extend on themselves to form products that do not amplify and are not detected.

Likewise, the above-described methods for detecting unmethylated residues in target DNA have multiple levels of discrimination allowing for the highest levels of sensitivity and specificity, even with low-abundance unmethylated targets. These levels of discrimination mirror those articulated above, where use of methylation insensitive restriction enzymes is optional. Finally, an overwhelming advantage of the methods described herein is the ability to simultaneously detect and quantify low-abundance methylated and unmethylated targets in the same initial nuclease-ligation reactions.

BRIEF DESCRIPTION OF THE DRAWINGS

FIGS. 1A-1B show one embodiment of the restriction endonuclease-ligation-polymerase process of the present invention. In FIG. 1A, double-stranded target DNA is cleaved by methylation sensitive restriction enzyme(s) (e.g., HinP1I). The dsDNA digestion products containing one or more unmethylated residues are denatured, generating a single stranded digestion product having a unique ligation competent 5' $PO_4$ that is suitable for ligation to an oligonucleotide adapter. ssDNA that is present in the sample is not digested by these enzymes and will not generate such a 5' phosphate. An oligonucleotide adapter is provided that comprises a first primer-specific portion and a 3' end configured to ligate to the digestion product. The 3' end of the oligonucleotide adapter is hybridized to its complement, where the complement of the 3' end is coupled to a region complementary to a 5' portion of a digestion product. The complement of the 3' end and the region complementary to a 5' portion of the digestion product comprise a uracil containing oligonucleotide as shown in FIG. 1A, step 2. The oligonucleotide adapter hybridizes and ligates to its corresponding digestion product in a sequence specific manner (FIG. 1A, step 2) to form adapter tagged digestion products. Subsequently, the hybridized uracil containing oligonucleotide is digested away using uracil DNA glycosylase (UDG). A primary PCR is performed using a primary primer set comprising (i) a first primary oligonucleotide primer comprising a nucleotide sequence that is the same as the first primer specific portion of the adapter tagged digestions products and (ii) a second primary oligonucleotide primer comprising a nucleotide sequence that is complementary to a region of the digestion product, and a second primer-specific portion. This approach will generate PCR products only if the target sequence is unmethylated at the site that generates the 5' end suitable for ligation. FIG. 1B is analogous to FIG. 1A; however, in this case, double-stranded target DNA is cleaved by both methylation insensitive restriction enzyme(s) (e.g. HaeIII), and methylation sensitive restriction enzyme(s) (e.g., HinP1I). In this example, the second primary oligonucleotide primer comprises a nucleotide sequence that is complementary to a region of the digestion product that is downstream of one or more methylated, uncleaved restriction sites, and a second primer-specific portion. This approach will generate PCR products only if the target DNA sequences between the adapter and the locus specific primers were methylated (and hence refractory to cleavage by the methylation-sensitive enzymes). Methylated cytosine is shown as "c*". Ligase is shown as a circle; polymerase as a diamond. Examples of methylation sensitive restriction enzymes that can be used: AciI, HinP1I, Hpy99I, HpyCH4IV, BstUI, HpaII, HhaI or a combination thereof. Examples of methylation insensitive restriction enzymes that can be used: MspI, HaeIII, AluI, TaqI, HpyCH4V, HpyCH4III, BfaI, NlaIII, DdeI, BsaJI, or a combination thereof.

FIGS. 2A-2B show an embodiment of the restriction endonuclease-ligation-polymerase process of the present invention using a hairpinned ligation adapter. In FIG. 2A, double-stranded target DNA is cleaved by methylation sensitive restriction enzyme(s) (e.g., HinP1I). The dsDNA digestion products are denatured, generating a single stranded digestion product having a unique ligation competent 5' $PO_4$ that is suitable for ligation to an oligonucleotide adapter. In this figure, the first primer-specific portion and the complement of the 3' end of each oligonucleotide adapter are coupled to permit hairpin formation. After denaturation, the single-stranded digestion products hybridize to their complementary region of the hairpinned oligonucleotide adapters in a sequence-specific manner such that the 3' end of the adapter is adjacent to the 5' phosphate end of the single-stranded digestion product, and in the presence of a DNA ligase, the oligonucleotide adapters ligate to their hybridized single-stranded digestion products to form adapter tagged digestion products. PCR is performed using a primary primer set as described in reference to FIG. 1A. The 5'→3' exonuclease activity of polymerase destroys the template portion of the ligated oligonucleotide, creating a primary extension product. Unligated hairpin oligonucleotide adapters will extend on themselves and not amplify further. This approach will generate PCR products only if the target sequence is unmethylated at the site that generates the 5' end suitable for ligation. FIG. 2B is analogous to FIG. 2A; however, in this case, double-stranded target DNA is cleaved by both methylation insensitive restriction enzyme(s) (e.g. HaeIII), and methylation sensitive restriction enzyme(s) (e.g., HinP1I). In this example, the second primary oligonucleotide primer comprises a nucleotide sequence that is complementary to a region of the digestion product portion of the adapter tagged digestion product that is downstream of one or more methylated, uncleaved restriction sites, and a second primer-specific portion (locus-specific tag). This approach will generate PCR products only if the target DNA sequences between the adapter and the locus specific primers were methylated (and hence refractory to cleavage by the methylation-sensitive enzymes). Methylated cytosine is shown as "c*". Ligase is shown as a circle; polymerase as a diamond. Examples of methylation sensitive restriction enzymes that can be used: AciI, HinP1I, Hpy99I, HpyCH4IV, BstUI, HpaII, HhaI or a combination thereof. Examples of methylation insensitive restriction enzymes that can be used: MspI, HaeIII, AluI, TaqI, HpyCH4V, HpyCH4III, BfaI, NlaIII, DdeI, BsaJI, or a combination thereof.

FIGS. 9A-9D show various embodiments of the restriction endonuclease-ligation process of the present invention using dual ligation. In FIG. 9A, Step 1, double-stranded target DNA is cleaved by methylation sensitive restriction enzyme(s) (e.g., HinP1I). dsDNA digested fragments are denatured, generating single-stranded digestion products containing a unique ligation competent 5' $PO_4$ as well as a unique ligation competent 3'OH. Single-stranded DNA that is present in the sample is not digested by these enzymes and will not generate such a 5' phosphate or 3' OH. A plurality of oligonucleotide adapter sets are added, each oligonucleotide adapter set comprising a first oligonucleotide adapter having a 3' end configured to ligate to a 5' end of a digestion product and hybridized to its complement, where the complement of the 3' end is coupled to a region complementary to the 5' portion of an digestion product, and a second oligonucleotide adapter having a 5' end configured to ligate to a 3' end of a digestion product and hybridized to its complement, where the complement of the 5' end is coupled to a region complementary to the 3' portion of a digestion product. In this figure, the complementary portions of the oligonucleotide adaptors and the regions of the adapters that are complementary to the digestion product comprise uracil containing oligonucleotides. After denaturation, the single-stranded digestion products hybridize and ligate to their corresponding oligonucleotide adapters of an adapter set in a sequence specific manner (FIG. 9A, Step 2). Subsequently, the hybridized uracil containing oligonucleotide is digested away using uracil DNA glycosylase (UDG). An optional PCR is performed (FIG. 9A, Step 3) using a primary primer set comprising (i) a first primary oligonucleotide primer comprising a nucleotide sequence that is the same as the first primer specific portion of the dual adapter tagged digestions products and (ii) a second primary oligonucleotide primer comprising a nucleotide sequence that is complementary to the second primer-specific portion of the dual adapter tagged digestions products. This approach will generate detectable products corresponding to genomic DNA fragments where both restriction endonuclease sites are unmethylated, thereby allowing for the generation of a specific 5' phosphorylated end and a specific 3' end suitable for ligation. In samples where at least one of these sites is methylated or DNA is single-stranded, the DNA is not digested by these enzymes and will not generate a substrate suitable for ligation, and thus no PCR amplification or signal. Ligase is shown as a circle; polymerase as a diamond. FIG. 9B shows another embodiment of the restriction endonuclease-ligation process of the present invention using dual ligation of hairpinned adapters. The process is similar to that described for FIG. 9A, except that the 3' end and the complement of the 3' end of the first oligonucleotide adapter are coupled to permit the first oligonucleotide adapter to form a hairpin, and the 5' end and the complement of the 5' end of the second oligonucleotide adapter are coupled to permit the second oligonucleotide adapter to form a hairpin. The second hairpinned oligonucleotide adapter also has a 5' oligonucleotide flap portion containing a nucleotide sequence that is complementary to a 3' region of the second oligonucleotide adapter. The "X"" in the template oligonucleotide indicates a blocking group on the 3' end, e.g., a phosphate, C3 or any other moiety non-extendable by a polymerase. After denaturation, the single-stranded digestion products hybridize to their complementary region of the first and second oligonucleotide adapters in a sequence-specific manner. The 5' oligonucleotide flap of the second oligonucleotide adapter is cleaved to generate a ligation competent 5' phosphate, and in the presence of DNA ligase, the oligonucleotide adapters ligate to their hybridized single-stranded digestion products to form dual adapter tagged digestion products (FIG. 9B, Step 2). An optional PCR is performed as described in FIG. 9A (FIG. 9B, Step 3). This approach will generate ligation or PCR products corresponding to genomic DNA fragments where both sites are unmethylated, generating a specific 5' phosphorylated end and a specific 3' end suitable for ligation. In samples where at least one site is methylated or DNA is single-stranded, it is not digested by these enzymes and will not generate a substrate suitable for ligation, and thus no PCR amplification or signal. FIGS. 9C and 9D show the generalized embodiment of the restriction endonuclease-ligation process of the present invention for detection of either unmethylated and/or methylated residues using dual ligation of coupled hairpin adapters. In FIG. 9C double-stranded target DNA is digested with methylation-insensitive enzyme(s) and methylation-sensitive enzyme(s) to generate digestion products that contain one or more methylated, uncleaved restriction endonuclease sites. As shown in this figure, the hairpinned oligonucleotide adapters of FIG. 9B can be coupled to each other. The coupled hairpinned oligonucleotide adapters hybridize and ligate to their respective digestion products as shown in FIG. 9C, Step 2. An optional PCR step using universal primers detects only DNA where both sites are either unmethylated, or one or more methylated, uncleaved restriction sites was present in the fragment (FIG. 9C, Step 3). Unligated hairpinned second oligonucleotide adapters extend from their 3'OH end onto themselves until reaching the polymerase blocker (X). Signal is generated for DNA fragments where both sites are either unmethylated when cleaved by methyl-sensitive enzyme(s), and/or when methyl-insensitive sites flank one or more methylated, uncleaved restriction sites and both methyl-sensitive and methyl-insensitive enzymes are used, generating a specific 5' phosphorylated end and a specific 3' end suitable for ligation. Ligase is shown as a circle; polymerase as a diamond. FIG. 9D shows the generalized case for target fragments of about 20-40 bases or about 30-150 or more bases. Signal is generated only for DNA fragments where both sites are either unmethylated when cleaved by methyl-sensitive enzyme(s), and/or when methyl-insensitive sites flank one or more methylated, uncleaved restriction sites and both methyl-sensitive and methyl-insensitive enzymes are used, generating a specific 5' phosphorylated end and a specific 3' end suitable for ligation. Left-hand portion of FIG. 9D shows primer design when fragment generated is about 20-30 bases. Right-hand portion of FIG. 9D shows primer design when fragment generated is about 30-150 or more bases.

DETAILED DESCRIPTION OF THE INVENTION

Figure 2A:
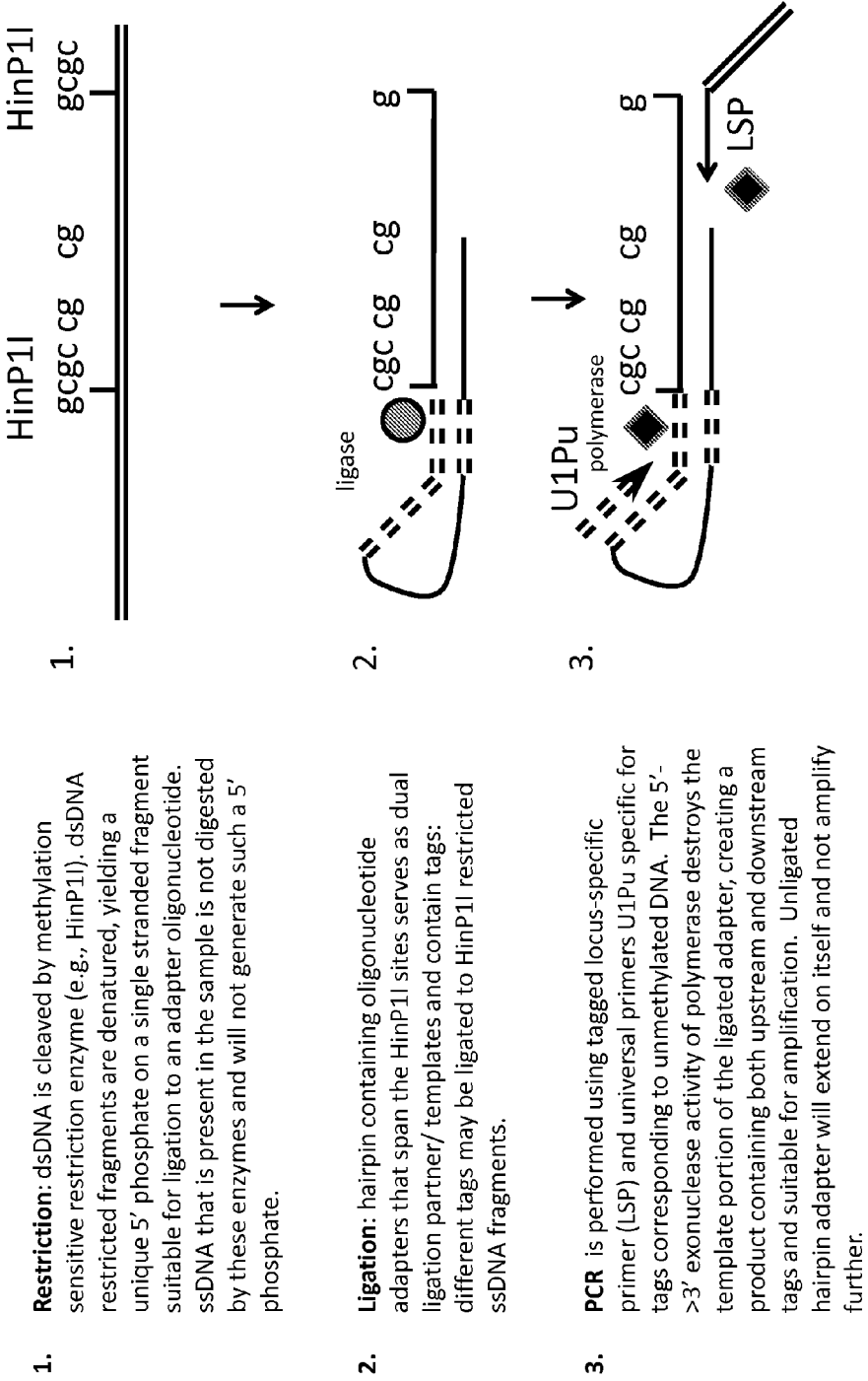

A first aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues and subjecting the one or more target nucleic acid molecules in the sample to at least one methylation insensitive enzyme digestion reaction and at least one methylation sensitive enzyme digestion reaction to form a plurality of digestion products. A plurality of oligonucleotide adapters are provided, each oligonucleotide adapter comprising a first primer-specific portion and a 3' end, said 3' end being configured to ligate to 5' portion of a digestion product and hybridized to its complement, wherein the complement of the 3' end is coupled to a region complementary to a 5' portion of a digestion product. The digestion products are subjected to a ligation reaction comprising a denaturation treatment to form single-stranded digestion products, a hybridization treatment, wherein the single-stranded digestion products hybridize to their complementary region of the oligonucleotide adapters in a sequence-specific manner such that the 3' end of the adapter is adjacent to the 5' end of the single-stranded digestion product, and ligation treatment, wherein the oligonucleotide adapters ligate to their hybridized single-stranded digestion products thereby forming adapter tagged digestion products. The method further involves providing one or more primary oligonucleotide primer sets, each primary primer set comprising (i) a first primary oligonucleotide primer having a nucleotide sequence that is the same as the first primer specific portion of the adapter tagged digestion products, and (ii) a second primary oligonucleotide primer comprising a nucleotide sequence that is complementary to a region of the digestion product that is 3' of one or more methylated, uncleaved restriction sites, and a second primer-specific portion. The plurality of adapter tagged digestion products, the one or more primary oligonucleotide primer sets, and a first polymerase are blended to form a first polymerase chain reaction mixture, and the first polymerase chain reaction mixture is subjected to one or more polymerase chain reaction cycles comprising a denaturation treatment, a hybridization treatment, and an extension treatment thereby forming primary extension products. The primary extension products are detected and distinguished, thereby identifying the presence of one or more target nucleic acid molecules differing from other nucleic acid molecules in the sample by one or more methylated residues.

FIGS. 1B and 2B depict the process of detecting one or more target nucleic acid molecules differing from other nucleic acid molecules in the sample by one or more methylated residues using the coupled restriction endonuclease-ligation-polymerase chain reaction (PCR) process of the present invention. The process begins by cleaving double stranded DNA in a sample using one or more methylation insensitive restriction endonucleases and one or more methylation sensitive restriction endonucleases (FIGS. 1B and 2B, step 1). The double-stranded digestion products are denatured to yield single-stranded DNA fragments containing unique 5' phosphate groups suitable for ligation to an adapter oligonucleotide in a sequence specific manner.

As used herein, a "methylation insensitive restriction endonuclease" is an endonuclease that cleaves a target DNA recognition sequence in the presence or in the absence of a particular methylated residue within the recognition sequence (i.e., it is insensitive to the presence of a particular methylated reside within its recognition sequence). In the context of this application, and for the examples below, the methylated residue is a 5-methyl-C, within the sequence CpG (i.e. 5-methyl-CpG), which is often methylated in clinical samples from patients. TaqI is an example of a methylation insensitive restriction enzyme that cleaves the sequence TCGA if the C is a 5-methyl-C. However, TaqI does not cleave the same recognition sequence if the A is the methylated residue. A non-limiting list of methylation insensitive restriction endonuclease enzymes that are suitable for use in the methods of the present invention include, without limitation, MspI, HaeIII, AluI, TaqI, HpyCH4V, HpyCH4III, BfaI, NlaIII, DdeI, BsaJI, or any combination thereof.

As also used herein, "methylation sensitive restriction endonuclease" is an endonuclease that will not cleave its cognate recognition sequence in a nucleic acid molecule when it contains a methylated residue (i.e., it is sensitive to the presence of a methylated residue within its recognition sequence). For the examples below, the methylated residue is a 5-methyl-C, within the sequence CpG (i.e. 5-methyl-CpG). A non-limiting list of methylation sensitive restriction endonuclease enzymes that are suitable for use in the methods of the present invention include, without limitation, AciI, HinP1I, Hpy99I, HpyCH4IV, BstUI, HpaII, HhaI, or any combination thereof.

In the next step of the coupled restriction endonuclease-ligation-PCR process, the oligonucleotide adapters are ligated to the single-stranded digestion products (see FIGS. 1B and 2B, Step 2). Each oligonucleotide adapter comprises at least a first primer-specific portion, and a 3' end that is configured to ligate to the 5' end of a digestion product and is hybridized to its complement. The complement of the 3' end is coupled to a region complementary to a 5' portion of a digestion product. In the embodiment depicted in FIG. 1B, the complement of the 3' end coupled to the region complementary to the 5' portion of the digestion product is a uracil containing oligonucleotide. The uracil containing oligonucleotide brings the 3' end of the oligonucleotide adapter adjacent to the 5' phosphate end of the digestion product and serves as a template to facilitate ligation of the oligonucleotide adapter to the digestion product to form adapter tagged digestion products. Following ligation, the uracil containing oligonucleotide is digested using, for example, uracil DNA glycosylase (FIG. 1B, Step 3).

In the embodiment depicted in FIG. 2B, the first primer specific portion of the oligonucleotide adapter is coupled to the complement of the 3' end of the oligonucleotide adapter which permits the oligonucleotide adapter to form a hairpin. As show in FIG. 2B, this hairpinned oligonucleotide adapter guides the 3' end of the adapter to the 5' phosphate end of a digestion product and serves as a template for ligation to form the adapter tagged digestion product. Following ligation, the complement of the 3' end and the region complementary to the 5' portion of the digestion product of the hairpinned oligonucleotide adapter are cleaved by the 5'→3' nuclease activity of the polymerase that is used in the subsequent PCR step (FIG. 2B, Step 3).

The ligation reaction utilized in the methods of the present invention is well known in the art. In accordance with this and all aspects of the present invention, ligases suitable for ligating oligonucleotide adaptors to their corresponding digestion products include, without limitation, *Thermus aquaticus* ligase, *E. coli* ligase, T4 DNA ligase, T4 RNA ligase, Taq ligase, 9 No ligase, and *Pyrococcus* ligase, or any other thermostable ligase known in the art.

In accordance with this and all aspects of the present invention the oligonucleotide adapters and/or the oligonucleotide primers can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, polymerase blocking groups, spacers, and mixtures thereof.

Following ligation of the oligonucleotide adapter to the 5' end of the single stranded digestion products, the adapter tagged digestion products are amplified in a PCR step as shown in Step 4 of FIG. 1B and Step 3 of FIG. 2B. The PCR is performed using a first oligonucleotide primer that has the same nucleotide sequence as the first primer-specific portion of the oligonucleotide adapter or a smaller portion thereof. The first primer-specific portion can be a universal primer portion, i.e., a primer portion that is the same for all oligonucleotide adapters regardless of the target nucleic acid molecule being detected. In accordance with this embodiment, the first oligonucleotide primer is a universal oligonucleotide primer. The second oligonucleotide primer is a tagged locus-specific primer (LSP). This second oligonucleotide primer is complementary to a region of the digestion product that is downstream of one or more methylated, uncleaved restriction sites. The second oligonucleotide primer also contains at least a second primer-specific portion.

In one embodiment of the present invention, the first and/or second oligonucleotide primers of a primer set are designed to contain a cleavable blocking group on their 3' end to enhance target-specific amplification. For example, the primers may contain a single ribonucleotide residue near their 3' end which prevents polymerase extension of the primer. Primer hybridization to complementary primer-specific portions on the adapter tagged digestion product forms a substrate for RNase H2, which cleaves the primer 5' to the RNA base thereby generating a 3'-OH on the primer that is capable of polymerase extension (see Dobosy et al., "RNase H-dependent PCR (rhPCR): Improved Specificity and Single Nucleotide Polymorphism Detection Using Blocked Cleavable Primers," *BMC Biotechnology* 11:80 (2011), which is hereby incorporated by reference in its entirety).

The polymerase chain reaction process is the well known in the art and is fully described in H. Erlich, et. al., "Recent Advances in the Polymerase Chain Reaction," *Science* 252: 1643-50 (1991); M. Innis, et. al., *PCR Protocols: A Guide to Methods and Applications*, Academic Press: New York (1990); and R. Saiki, et. al., "Primer-directed Enzymatic Amplification of DNA with a Thermostable DNA Polymerase," *Science* 239: 487-91 (1988), which are hereby incorporated by reference in their entirety.

The primary extension products resulting from the polymerase chain reaction step contain the first primer-specific portion, the digestion product, and a second-primer specific portion. Methods for detecting the primary extension products are described in detail herein.

Another aspect of the present invention is directed to a method for identifying, in a sample, one or more target nucleic acid molecules differing from other nucleic acid molecules in the sample by one or more unmethylated residues. This method involves providing a sample containing one or more target nucleic acid molecules potentially containing one or more unmethylated residues and subjecting the one or more target nucleic acid molecules in the sample to at least one methylation sensitive enzyme digestion reaction to form a plurality of digestion products comprising one or more unmethylated residues. A plurality of oligonucleotide adapters are provided, each oligonucleotide adapter comprising a first primer-specific portion and a 3' end, said 3' end being configured to ligate to a 5' portion of a digestion product and hybridized to its complement, wherein the complement of the 3' end is coupled to a region complementary to a 5' portion of a digestion product. The digestion products are subjected to a ligation reaction comprising a denaturation treatment to form single-stranded digestion products, a hybridization treatment, wherein the single-stranded digestion products hybridize to their complementary region of the oligonucleotide adapters in a sequence-specific manner such that the 3' end of the adapter is adjacent to the 5' end of the single-stranded digestion product, and ligation treatment, wherein the oligonucleotide adapters ligate to their hybridized single-stranded digestion products thereby forming adapter tagged digestion products. The method further involves providing one or more primary oligonucleotide primer sets, each primary primer set comprising (i) a first primary oligonucleotide primer comprising a nucleotide sequence that is the same as the first primer specific portion of the adapter tagged digestion products and (ii) a second primary oligonucleotide primer comprising a nucleotide sequence that is complementary to a region of the digestion product, and a second primer-specific portion. The plurality of adapter tagged digestion products, the one or more primary oligonucleotide primer sets, and a first polymerase are blended to form a first polymerase chain reaction mixture, and the first polymerase chain reaction mixture is subjected to one or more polymerase chain reaction cycles comprising a denaturation treatment, a hybridization treatment, and an extension treatment thereby forming primary extension products. The primary extension products are detected and distinguished, thereby identifying the presence of one or more target nucleic acid molecules differing from other nucleic acid molecules in the sample by one or more unmethylated residues.

FIGS. 1A and 2A depict the process of detecting one or more target nucleic acid molecules differing from other nucleic acid molecules in the sample by one or more unmethylated residues using the coupled restriction endonuclease-ligation-PCR process of the present invention. The first step of this process begins by cleaving double stranded DNA in a sample using only one or more methylation sensitive restriction endonucleases (FIGS. 1A and 2A, step 1). Suitable methylation sensitive restriction endonucleases are described supra. The resulting double-stranded digestion products contain unmethylated residues at the restriction endonuclease site on the 5' end of the digestion product. The double stranded digestion products are denatured to yield single-stranded DNA fragments containing unique 5' phosphate groups suitable for ligation to an adapter oligonucleotide in a sequence specific manner.

In the next step of the coupled restriction endonuclease-ligation-PCR process, the oligonucleotide adapters are ligated to the single-stranded digestion products. The oligonucleotide adapters depicted in FIG. 1A (Step 2), are similar to the oligonucleotide adapters described above in reference to FIG. 1B, i.e., they comprise a uracil containing oligonucleotide that guides ligation of the 3' end of the oligonucleotide adapter to the 5' phosphate end of the digestion product. As noted above, the uracil containing oligonucleotide is subsequently destroyed by uracil DNA glycosylase treatment (FIG. 1A, Step 3). Alternatively, as depicted in FIG. 2A, Step 2, the first primer-specific portion of the oligonucleotide adapter is coupled to the complement of the 3' end of the oligonucleotide adapter which permits hairpin formation. As described above in reference to FIG. 2B, this hairpinned oligonucleotide adapter guides ligation of the 3' end of the adapter to the 5' end of the digestion product.

Following ligation of the oligonucleotide adapter to the single stranded digestion products, the adapter tagged digestion products are amplified in a PCR step as show in Step 4 of FIG. 1A and Step 3 of FIG. 2A. The PCR is performed using a first oligonucleotide primer that has the same nucleotide sequence as the first primer-specific portion of the oligonucleotide adapter or a smaller portion thereof. The first oligonucleotide primer can be a universal oligonucleotide primer. The second oligonucleotide primer is a tagged LSP that is complementary to a region of the digestion product and also contains a second primer-specific portion. As described supra, one or both of the oligonucleotide primers utilized in the PCR can be designed to contain a 3' blocking group, e.g., an RNA residue, that blocks polymerase extension. Only when the primer(s) hybridizes to its complementary sequence on the adapter tagged digestion products will the 3' blocking group be cleaved (e.g., by RNase H2), thereby generating a 3'OH capable of polymerase extension (see Dobosy et al., "RNase H-dependent PCR (rhPCR): Improved Specificity and Single Nucleotide Polymorphism Detection Using Blocked Cleavable Primers," *BMC Biotechnology* 11:80 (2011), which is hereby incorporated by reference in its entirety).

The primary extension products resulting from the polymerase chain reaction step contain the first primer-specific portion, the digestion product, and a second-primer specific portion. The primary extension products are detected and distinguished, thereby identifying the presence of one or more target nucleic acid molecules differing from other nucleic acid molecules in the sample by one or more unmethylated residues.

The processes described in FIGS. 1A and 1B include the same four steps: (i) restriction of double-stranded DNA to generate unique 5' phosphate groups, (ii) ligation of oligonucleotide adapters to the 5' ends of the uniquely generated digestion products, (iii) removal of template strand, for example by UDG digestion of uracil-containing oligonucleotides, and (iv) use of locus-specific and universal primers to PCR amplify products suitable for subsequent detection and quantification. As such, the two processes may be performed on the same sample simultaneously, allowing for accurate identification and quantification of both low abundance methylation and unmethylation targets in the same reaction. Likewise, the processes described in FIGS. 2A and 2B include the same three steps: (i) restriction of double-stranded DNA to generate unique 5' phosphate groups, (ii) ligation of oligonucleotide adapters to the 5' end of uniquely generated digestion products, and (iii) use of locus-specific and universal primers to PCR amplify products suitable for subsequent detection and quantification. As such, the two processes may be performed on the same sample simultaneously, allowing for accurate identification and quantification of both low abundance methylation and unmethylation targets in the same reaction.

Figure 3:
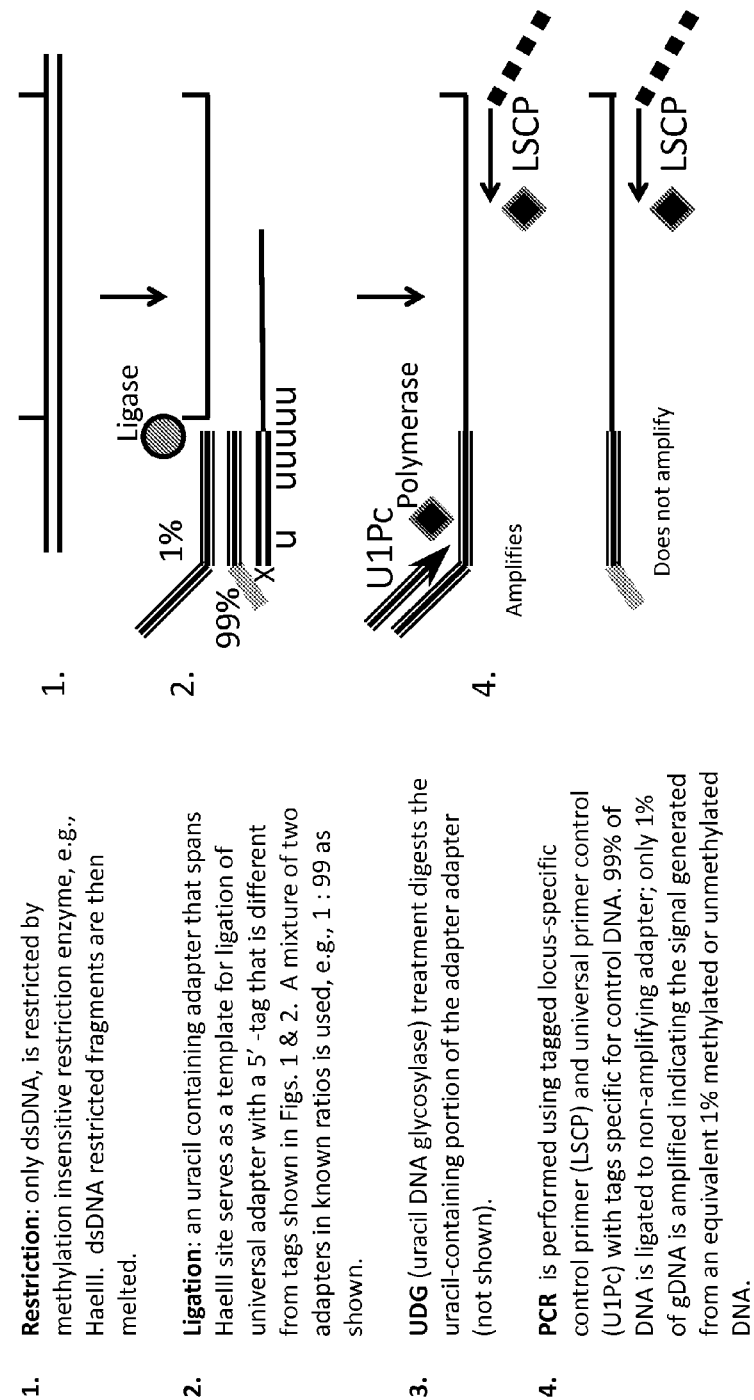
FIG. 3 demonstrates how a control region can be used as a positive control in the same reaction mixture shown in FIGS. 1 and 2, to provide a control signal equivalent to the presence of 1% of either methylated or unmethylated DNA. The oligonucleotide adapters and primers are generally different from those used in the methods depicted in FIGS. 1 and 2. Accordingly, control DNA is detected in the same reaction as methylated/unmethylated target, but using a different detection label, e.g. a fluorescent dye. After denaturing double stranded control digestion products, one of two uracil containing oligonucleotide adapters are ligated to the single-stranded template. One of the oligonucleotide adapters contains a first primer-specific portion, or other detectable tag, and the second oligonucleotide adapter does not contain the first primer-specific portion or detectable tag. The two oligonucleotide adapters are provided as a mixture in a known ratio, e.g. 1:99 as shown. After ligation, the hybridized uracil containing oligonucleotide of the adapter is digested away using uracil DNA glycosylase (UDG). PCR is performed using tagged locus-specific control primer (LSCP) and universal primer control (U1Pc) with tags specific for control DNA. 99% of DNA is ligated to non-amplifying oligonucleotide adapter and only 1% of genomic DNA is ligated to an oligonucleotide adapter that can be amplified and/or detected. The signal generated from the control reaction is equivalent to the signal that would be generated from a methylated or unmethylated target nucleic acid molecule present in 1% of the DNA sample FIG. 4 demonstrates how a control region can be used as a positive control in the same reaction mixture shown in FIGS. 1 and 2 using hairpin adapters to provide a control signal equivalent to the presence of 1% of either methylated or unmethylated DNA. The oligonucleotide adapters and primers are generally different from those used in FIGS. 1 and 2. Accordingly, control DNA is detected in the same reaction as methylated/unmethylated target, but using a different detection label, e.g. a fluorescent dye. Only dsDNA is digested by methylation insensitive restriction enzyme, e.g., HaeIII. After denaturing double stranded control digestion products, one of two hairpinned oligonucleotide adapters are ligated to the single-stranded template. One of the oligonucleotide adapters contains a first primer-specific portion, or other detectable tag, and the second oligonucleotide adapter does not contain the first primer-specific portion or detectable tag. The two oligonucleotide adapters are provided as a mixture in a known ratio, e.g. 1:99 as shown. PCR is performed using tagged locus-specific control primer (LSCP) and universal primer control (U1Pc) with tags specific for control DNA. The 5'→3' exonuclease activity of polymerase destroys the template portion of the ligated oligonucleotide adapter, creating a product containing both upstream and downstream tags and suitable for amplification. 99% of DNA is ligated to non-amplifying oligonucleotide adapters, and only 1% of DNA is ligated to an oligonucleotide adapter that can be amplified and or detected indicating the signal generated from an equivalent 1% methylated or unmethylated DNA.
Figure 4:
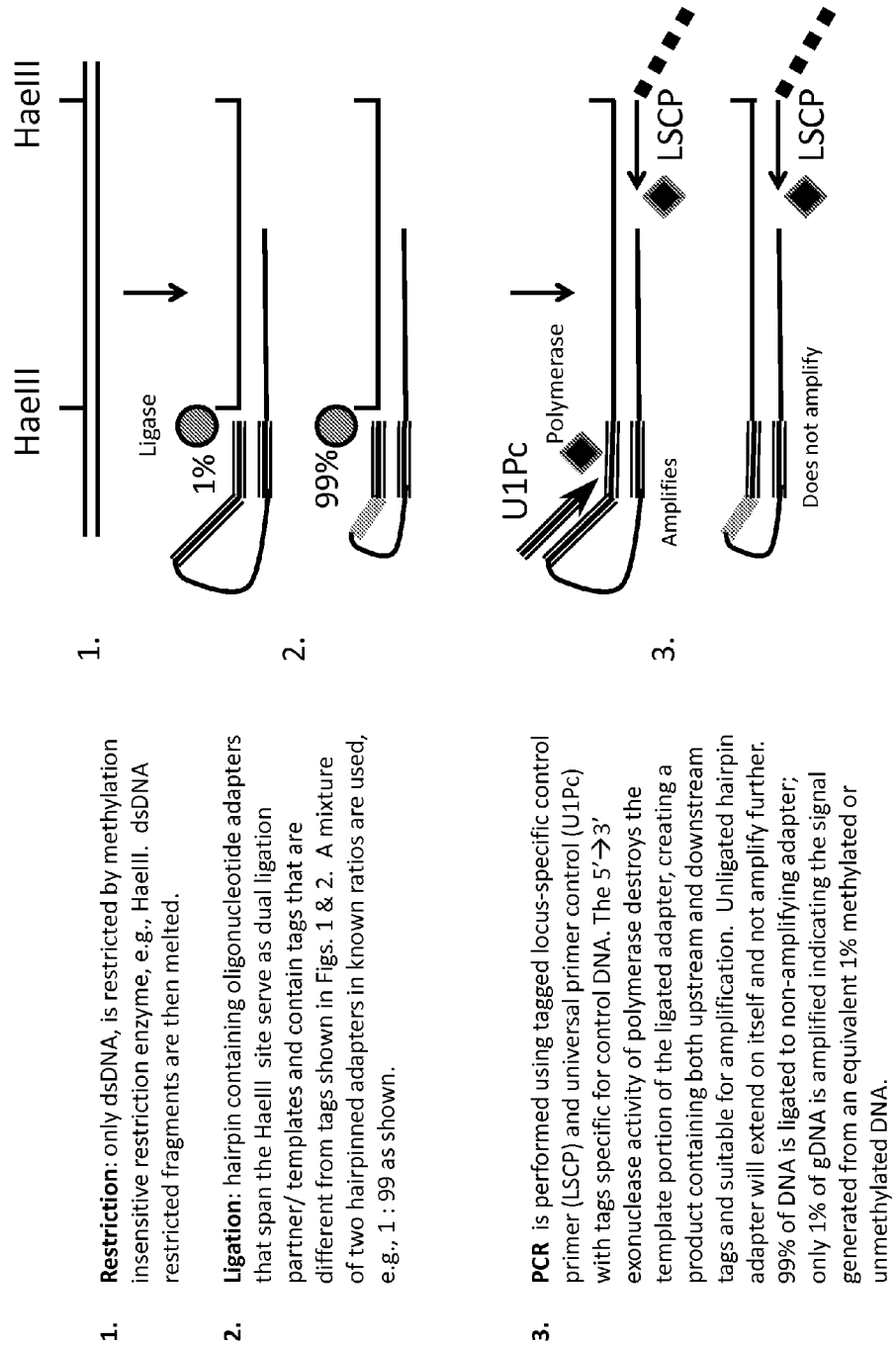

FIGS. 3 and 4 demonstrates how a known region of a nucleic acid molecule can be used as a positive control in the same reaction mixture shown in FIGS. 1 and 2, to provide a control signal equivalent to the presence of 1% of either methylated or unmethylated DNA. The oligonucleotide adapters and primers are generally different from those used in the methods depicted in FIGS. 1 and 2. Accordingly, control DNA is detected in the same reaction as methylated/unmethylated target, but using a different detection label, e.g. a fluorescent dye. As depicted in FIG. 3, after denaturing double stranded control digestion products, one of two uracil containing oligonucleotide adapters are ligated to the single-stranded template. As depicted in FIG. 4, after denaturing double stranded control digestion products, one of two hairpinned oligonucleotide adapters are ligated to the single-stranded template. In both examples, one of the oligonucleotide adapters contains a first primer-specific portion, or other detectable tag, and the second oligonucleotide adapter does not contain the first primer-specific portion or detectable tag. The two oligonucleotide adapters are provided as a mixture in a known ratio, e.g. 1:99 or 1:999, respectively. Both the uracil containing oligonucleotide adapter (FIG. 3) and the hairpinned oligonucleotide adapter (FIG. 4) are suitable for use in a control reaction. PCR is performed using tagged locus-specific control primer (LSCP) and universal primer control (U1Pc) with tags specific for control DNA. As a result of the ratio of tagged vs. untagged oligonucleotide adapters provided, 99% or 99.9% of DNA is ligated to non-amplifying (non-tagged) oligonucleotide adapter and only 1% or 0.1% of genomic DNA is ligated to an oligonucleotide adapter that can be amplified and/or detected. The signal generated from the control reaction is equivalent to the signal that would be generated from a methylated or unmethylated target nucleic acid molecule present in 1% or 0.1% of the DNA sample.

The primary extension products of the present invention can be detected using a variety of detection methods known in the art. For example, in one embodiment, of the present invention, one of the first or second oligonucleotide primers of a primer set used in the primary PCR step (i.e., Step 4 in FIGS. 1A-1B and Step 3 in FIGS. 2A-2B) contains a detectable label. Where the first oligonucleotide primer is universal primer, the detectable label is preferably coupled to the second oligonucleotide primer to achieve target-specific detection. A wide variety detectable labels are known in the art. Fluorescent dyes are particularly suitable for detecting and quantitating PCR products. Suitable fluorescent dyes include, without limitation, FAM, TET, JOE, VIC, HEX, CY3, TAMRA, TexasRed, CY5, ROX.

In another embodiment of the present invention, both the first and second primer-specific portions of the primary extension products have universal primer sequences allowing for a subsequent universal amplification of all primary extension products formed under a single set of conditions. This is particularly useful when detecting low abundance target nucleotide molecules. Accordingly, following primary extension product formation, a universal PCR amplification is performed to proportionally amplify all extension products in the sample. In accordance with this embodiment, the oligonucleotide adapters and/or second oligonucleotide primer of the primary oligonucleotide primer set are designed to contain one or more target-specific primer-specific portions or other detections portions (e.g., zip-code portion or unitaq portion) as described below to facilitated detection and/or quantitation.

In one embodiment of the present invention, detection of the primary extension products is facilitated by a zip-code portion. In accordance with this embodiment, either the oligonucleotide adapter or the second oligonucleotide primer of the primary primer set further comprises a zip-code portion. As used herein, a zip-code is a short nucleotide sequence, e.g., between 16 to 24 nucleotides in length, that has no sequence identity to the target nucleotide sequence, and preferably, little or no sequence identify to any genomic nucleotide sequence. In a collection of zip-codes, each zip-code differs in sequence from the sequence of other zip-codes in the collection by at least 25%, yet all zip-codes of a collection are designed to have similar melting temperatures so as to facilitate hybridization to complementary capture oligonucleotides under uniform hybridization conditions with little or no non-specific hybridization to non-capture oligonucleotide sequences. In one embodiment of the present invention, the zip-code portion is used to identify and distinguish different primary extension products in a sample, therefore the zip-code portion for each different primary extension product has a different nucleotide sequence. In an alternative embodiment, where the goal is to simply detect the presence or absence of one or more methylated or unmethylated residues in a particular genomic region, but the identity of the particular methylated or unmethylated residues within that region is not critical, the same zip-code portion may be used to detect different primary extension products. In either embodiment, incorporation of a zip-code into the oligonucleotide adapter or the second oligonucleotide primer of the primary primer set allows for highly multiplexed detection of various target sequences simultaneously. Methods of designing collections of zip-code sequences and their complementary capture oligonucleotides sequences are described in detail in U.S. Pat. Nos. 6,852,487, 7,455,965, and 6,506,594 all to Barany et al., which are hereby incorporated by reference in their entirety.

Detection using the zipcode can be carried out using traditional Taqman™ detection (see U.S. Pat. No. 6,270,967 to Whitcombe et al., and U.S. Pat. No. 7,601,821 to Anderson et al., which are hereby incorporated by reference in their entirety). In accordance with this embodiment, either the oligonucleotide adapter or second oligonucleotide primer of the primary primer set contains a zip-code portion such that the resulting primary extension product contains a zip-code portion. A collection of capture oligonucleotides is provided, where each capture oligonucleotide comprises a quencher molecule and a detectable label that are separated from each other (i.e., the Taqman™ probe). The quencher molecule and detectable label are in close enough proximity for the quencher molecule to quench any signal from the detectable label.

In one approach, the collection of capture oligonucleotides is added to the first polymerase chain reaction mixture (i.e., Step 4 of FIGS. 1A-1B and Step 3 of FIGS. 2A-2B). In accordance with this approach, the oligonucleotide adapter contains the zip-code portion such that the resulting adapter tagged digestion product also contains the zip-code. During the hybridization treatment of each PCR cycle, the capture oligonucleotides of the collection hybridize to their complementary zip-code portions of the adapter tagged digestion product or complements thereof. During the extension treatment of each PCR cycle, the secondary primer extends and cleaves the quencher molecule and/or the detectable label from hybridized capture oligonucleotides and the target nucleic acid molecule is detected upon the separation of the detectable label from the quencher molecule.

Figure 5:
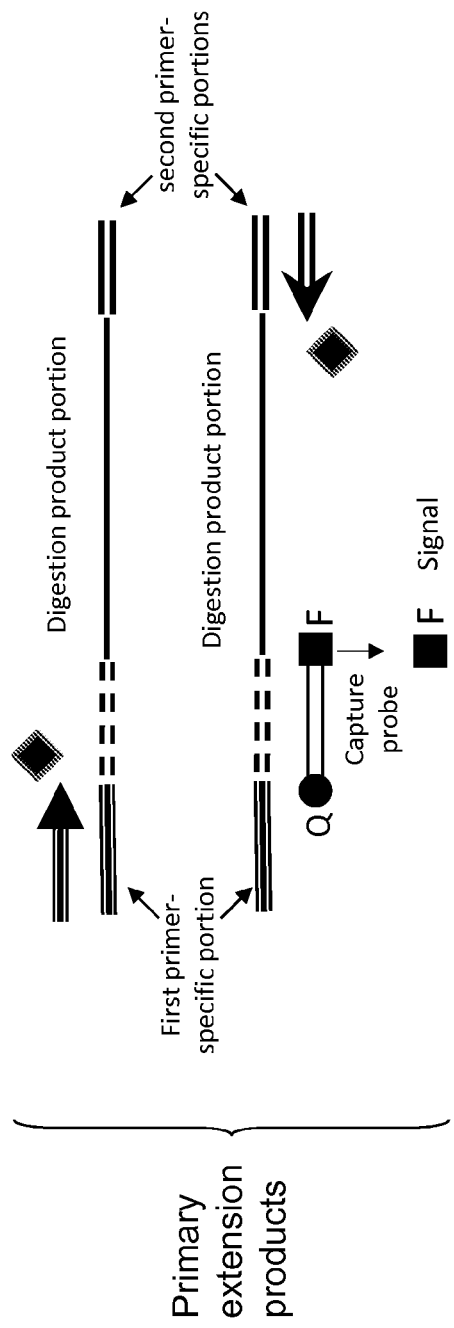
FIG. 5 shows detection of primary extension products generated by the restriction endonuclease-ligation-polymerase process of the present invention using the zip-code in a traditional Taqman® (Roche Molecular Systems, Pleasanton, Calif.) type assay where the capture oligonucleotide serves as the Taqman® probe.

In another approach, the primary extension products are detected by hybridization and cleavage of the capture oligonucleotide probes after the initial PCR step shown in Step 4 of FIGS. 1A and 1B and Step 3 of FIGS. 2A and 2B. This approach, which is shown in FIG. 5, is particularly suitable when detecting low abundance target nucleic acid sequences. In this approach, the collection of capture oligonucleotides, each comprising a quencher molecule and a detectable label that are in close proximity but separated from each other, are provided along with a secondary oligonucleotide primer set that is capable of hybridizing to the primary extension products. The capture oligonucleotides, the secondary oligonucleotide primers, and a polymerase are blended with the primary extension products to form a second PCR reaction. During the hybridization treatment of the second PCR reaction, the capture oligonucleotides hybridize to complementary zip-code portions of the primary extension products, and the secondary oligonucleotide primers hybridize to complementary regions of the primary extension products. During the extension treatment of each PCR cycle, the secondary primer extends and cleaves the quencher molecule and/or the detectable label from a hybridized capture oligonucleotide. The target nucleic acid molecule is detected upon the separation of the detectable label from the quencher molecule.

In yet another approach, the primary extension products may further include one or more unique sequences (ranging from 0 to 10 bases) internal to the first and second primer-specific portion (i.e., Unique Ai, Unique Bi), represented as follows.

Primer Portion 1-Unique Ai-Zipcode Zi-Target DNA-Unique Bi-Primer Portion 2

These unique sequences are introduced into the primary extension products via the oligonucleotide adapter and the second oligonucleotide primer of the primary primer set. For detection using Zipcode Taqman assays, after the 8-20 cycles of universal amplification, the sample would be diluted 10- to 100-fold and unique primers would be added that overlap with the Unique Ai and Unique Bi sequence for each product. The Taqman probe would be a capture oligonucleotide that is complementary to the zip-code sequence.

Another detection approach utilizing zipcodes involves having the zipcode portion split into two parts within the resulting adapter tagged digestion product. The split zipcode portions are brought in proximity to each other using a short region of complementary sequence on both sides of the split parts. In particular, the first oligonucleotide adapter comprises a first portion of the zip-code and a first tag portion that is 3' to the first zip-code portion, and the second oligonucleotide primer of the primary oligonucleotide primer set comprises a second portion of the zip-code and a second tag portion that is 5' to the second zip-code portion. The first and second tag portions of a primary extension product are complementary to each other, and preferably are between about 5 to 8 bases long. When the two tags are on the same single strand of an extension product, hybridization between the two tags allows for transient hairpin formation of the extension product. The hairpin is stabilized by hybridizing both halves of the zipcode sequence, which are brought in proximity to each other as a result of tag hybridization, to a full length complementary capture oligonucleotide.

Figure 6:
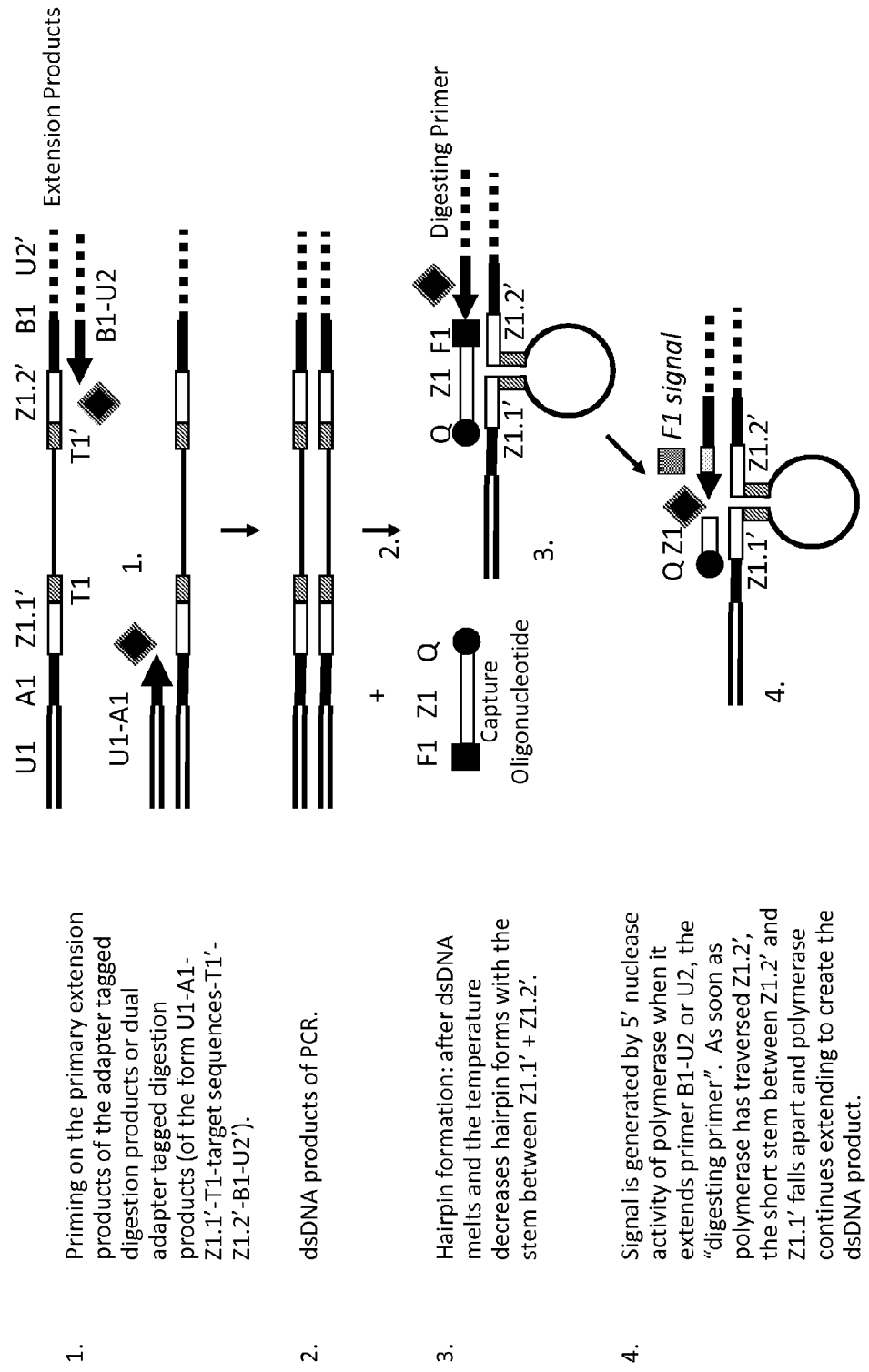
FIG. 6 shows an example of universal Taqman® split zip-code hairpin detection of products formed using the nuclease-ligation-PCR process of the present invention. The starting products can be the primary extension products of the adapter tagged digestion products, dual adapter tagged digestion products, or primary extension products of the dual tagged digestion products.

FIG. 6 shows an example of universal Taqman split zipcode hairpin detection. In this figure, and in accordance with the methods described above, the first oligonucleotide adapter comprises a first primer-specific portion (depicted in FIG. 6 as U1 and A1), a first portion of the zip-code (Z1.1'), and a first tag portion (T1) that is 3' to the first zip-code portion. The second oligonucleotide primer of the primary oligonucleotide primer set comprises a second portion of the zip-code (Z1.2'), a second tag portion (T1') that is 5' to the second zip-code portion, and the second primer-specific portion (B1-U2). The resulting primary extension products as shown in step 1 of FIG. 6, contain the (i) first primer-specific portion, U1-A1, where U1 is a universal primer specific portion and A1 is a unique, product-specific primer portion, (ii) the first zip-code portion (Z1.1'), (iii) the first tag portion (T1), (iv) the digestion product portion, (v) the second tag portion (T1'), (vi) the second portion of the zip-code (Z1.2'), and (vii) the second primer specific portion, B1-U2, where B1 is a unique, product-specific primer portion and U2 is a universal primer portion.

As shown in FIG. 6, Step 1, the A1 and B1 unique sequences serve to facilitate a product-specific PCR amplification of the primary extension product sequence when the PCR primers that are utilized span the universal primer portions and the A1 and B1 portions, respectively. This target-specific PCR amplification can optionally be preceded by a universal PCR amplification reaction using primers that hybridize to the 5' and 3' universal primer-specific portions (i.e., U1 and U2). A first universal amplification reaction is particularly suitable when detecting low abundance target nucleic acid sequences in a sample.

Following the target-specific PCR amplification of the primary extension products (FIG. 6, Step 1), the double stranded DNA products are denatured (FIG. 6, Step 2). As the temperature decreases, the first and second tag portions (T1 and T1') on one strand transiently hybridize together, bringing the first portion of the zipcode sequence (Z1.1' from the oligonucleotide adapter) in proximity to the second zipcode sequence (Z1.2' from the second oligonucleotide primer). The transient hybridization between T1 and T1' is stabilized by the simultaneous hybridization of a labeled capture oligonucleotide (Z1) that is complementary to the adjacently positioned split zipcode sequences (FIG. 6, Step 3). In one embodiment, the capture oligonucleotide has a quencher molecule (Q) and a detectable label (F) that are separated from each other, where the detectable label is quenched when in close proximity to the quencher molecule. Signal is generated by 5' nuclease activity of a polymerase as it extends a primer (i.e., the "digesting primer") that is bound to the universal primer-specific portion (U2), the unique B1 portion, or a combination thereof, and cleaves the hybridized capture oligonucleotide. Primer extension cleaves the detectable label from the capture oligonucleotide releasing the detectable label from the quencher molecule, enabling detection (FIG. 6, Step 4). As soon as polymerase has traversed Z1.2', the short stem between Z1.2' and Z1.1' falls apart and polymerase continues extending to create a dsDNA product. A wide variety of detectable labels, i.e., fluorescent dyes are known in the art and are commercially available, e.g., FAM, TET, JOE, VIC, HEX, CY3, TAMRA, TexasRed, CY5, ROX. Similarly, quencher molecules, e.g., MGB-NFQ, BHQ-[0123], ZEN quencher from IDT, are also well known to those skilled in the art.

Figure 7:
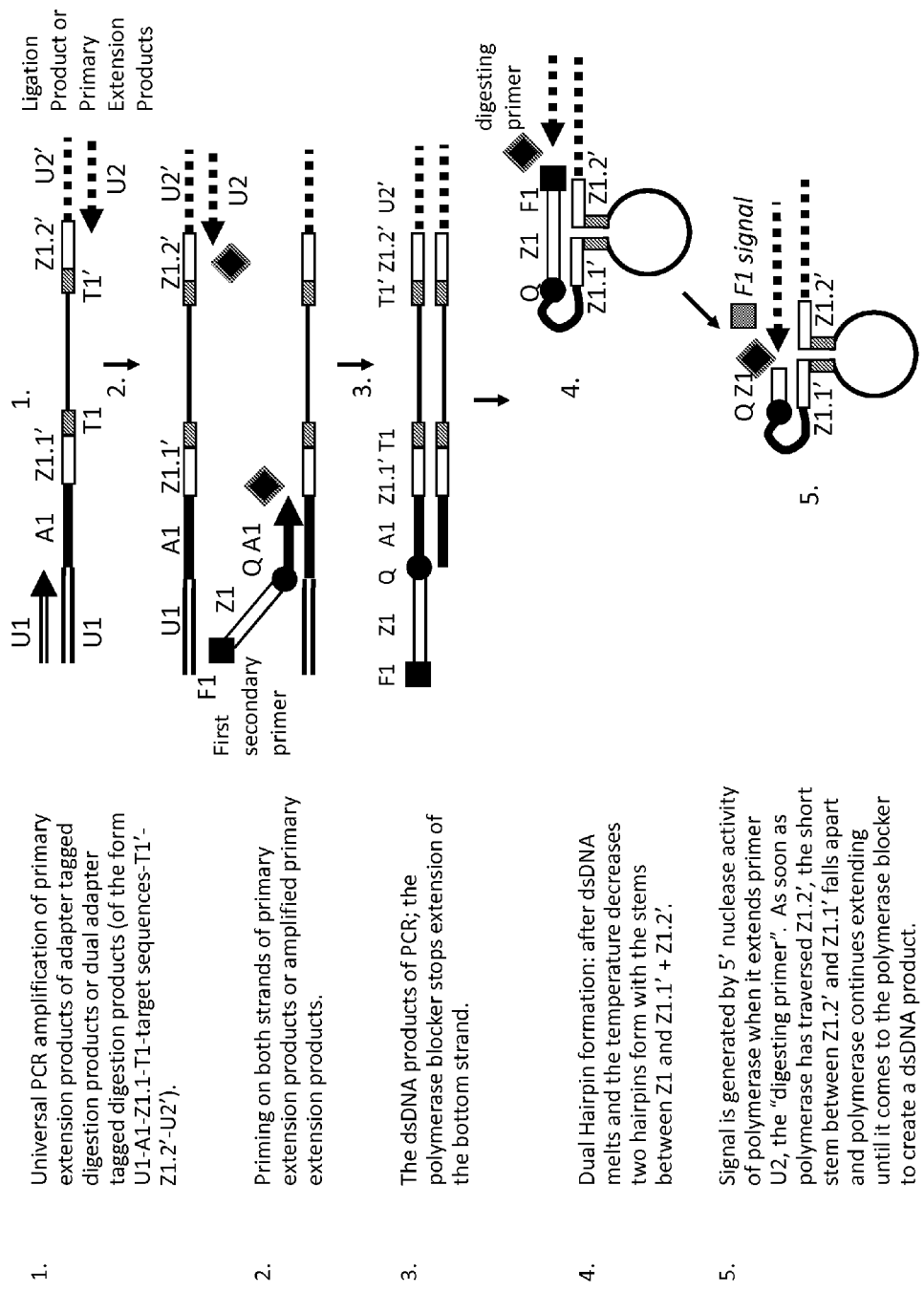
FIG. 7 shows an example of universal split zip-code hairpin detection of products formed using the nuclease-ligation-PCR process of the present invention. The starting products can be the primary extension products of the adapter tagged digestion products, dual adapter tagged digestion products, or primary extension products of the dual tagged digestion products.

FIG. 7 shows another example of split zip-code hairpin detection. In this figure, the primary extension products are formed using oligonucleotide adapters having a first primer-specific portion (U1 and A1), a first portion of the zip-code (Z1.1') and a first tag portion (T1) that is 3' to the first zip-code portion. The second oligonucleotide primer of the primary oligonucleotide primer set comprises a second portion of the zip-code (Z1.2'), a second tag portion (T1') that is 5' to the second zip-code portion, and the second primer-specific portion (U2). The resulting primary extension products as shown in step 1 of FIG. 7, contain the (i) first primer-specific portion, U1-A1, where U1 is a universal primer specific portion and A1 is a unique, product-specific primer portion (i.e., a third-primer portion), (ii) the first zip-code portion (Z1.1'), (iii) the first tag portion (T1), (iv) the digestion product portion, (v) the second tag portion (T1'), (vi) the second portion of the zip-code (Z1.2'), and (vii) the second primer specific portion (U2).

In Step 1 of FIG. 7, the primary extension products are optionally initially amplified using a universal oligonucleotide primer set that bind to the U1 and U2 primer portions of the primary extension products. The amplified primary extension products formed from this universal PCR step are subject to a secondary PCR step (FIG. 7, step 2) using a secondary primer set that includes a first secondary oligonucleotide primer having (i) a nucleotide sequence that is the same as the A1 primer portion (A1), (ii) a capture oligonucleotide portion (Z1) that is complementary to adjacently positioned first and second zip-code portions of an extension product (i.e., Z1.1' and Z1.2'), (iii) a quencher molecule (Q) and a detectable label (F) that are separated by said capture oligonucleotide portion. The second secondary oligonucleotide primer (U2) of the primer set has the same nucleotide sequence as the second primer specific portion of the second primary oligonucleotide primer. The quencher molecule of the first secondary primer can serve as a polymerase blocker to block polymerase extension of its complementary strand. Alternatively, a polymerase blocker such as HEG (hexethylene glycol), THF (tetrahydrofuran), Sp-18, or any other blocker known in the art that is sufficient to stop polymerase extension can be positioned proximal to the quencher moiety. The resulting double stranded DNA products (shown in FIG. 7, Step 3) are denatured, and the temperature decreased to allow dual hairpin formation with stems between Z1.1' and Z1.2' (stem formed by hybridization between T1 and T1') and between the capture oligonucleotide portion (Z1) and Z1.1'/Z1.2' (FIG. 7, Step 4). Signal is generated by 5' nuclease activity of polymerase when it extends a "digesting primer" complementary to the 5' universal primer-specific portion. Primer extension cleaves the detectable label (F) or the quencher molecule (Q) from the capture oligonucleotide releasing the detectable label (F) from the quencher molecule (Q), enabling detection (FIG. 7, Step 5). As soon as the polymerase has traversed Z1.2', the short stem between Z1.2' and Z1.1' falls apart and polymerase continues extending until it comes to the polymerase blocker to create a dsDNA product similar to that in step 1.

An alternative approach to utilizing the zipcode/capture oligonucleotide sequences for detection of the methylated or unmethylated products formed using the restriction endonuclease-ligation-PCR process of the present invention involves the UniTaq approach. The UniTaq system is fully described in U.S. Patent Application Publication No. 2011/0212846 to Spier, which is hereby incorporated by reference in its entirety. The UniTaq system involves the use of two to three short (1-10 nucleotides) unique "tag" sequences, where at least one of the unique tag sequences (Ai) is present in the oligonucleotide adapter, and the second and third unique tag portions (Bi and Ci) are in the second oligonucleotide primer of the primary oligonucleotide primer set. The resulting primary extension products contain the Ai sequence-digestion product sequences-Bi sequence-Ci sequence. The essence of the UniTaq approach is that a detectable signal is only detected when the oligonucleotide adapter correctly ligates to its corresponding digestion product in a sequence specific manner and the second oligonucleotide primer of the primary oligonucleotide primer correctly hybridizes to its corresponding adapter tagged digestion product.

In one embodiment of the present invention, the UniTaq tag portions of an oligonucleotide adapter and the second oligonucleotide primer are used to identify and distinguish individual primary extension products formed in a sample. In accordance with this embodiment, the UniTaq portions for each different primary extension product are different. In an alternative embodiment, the same UniTaq tag portions can be used to detect different ligation products.

Figure 8A:
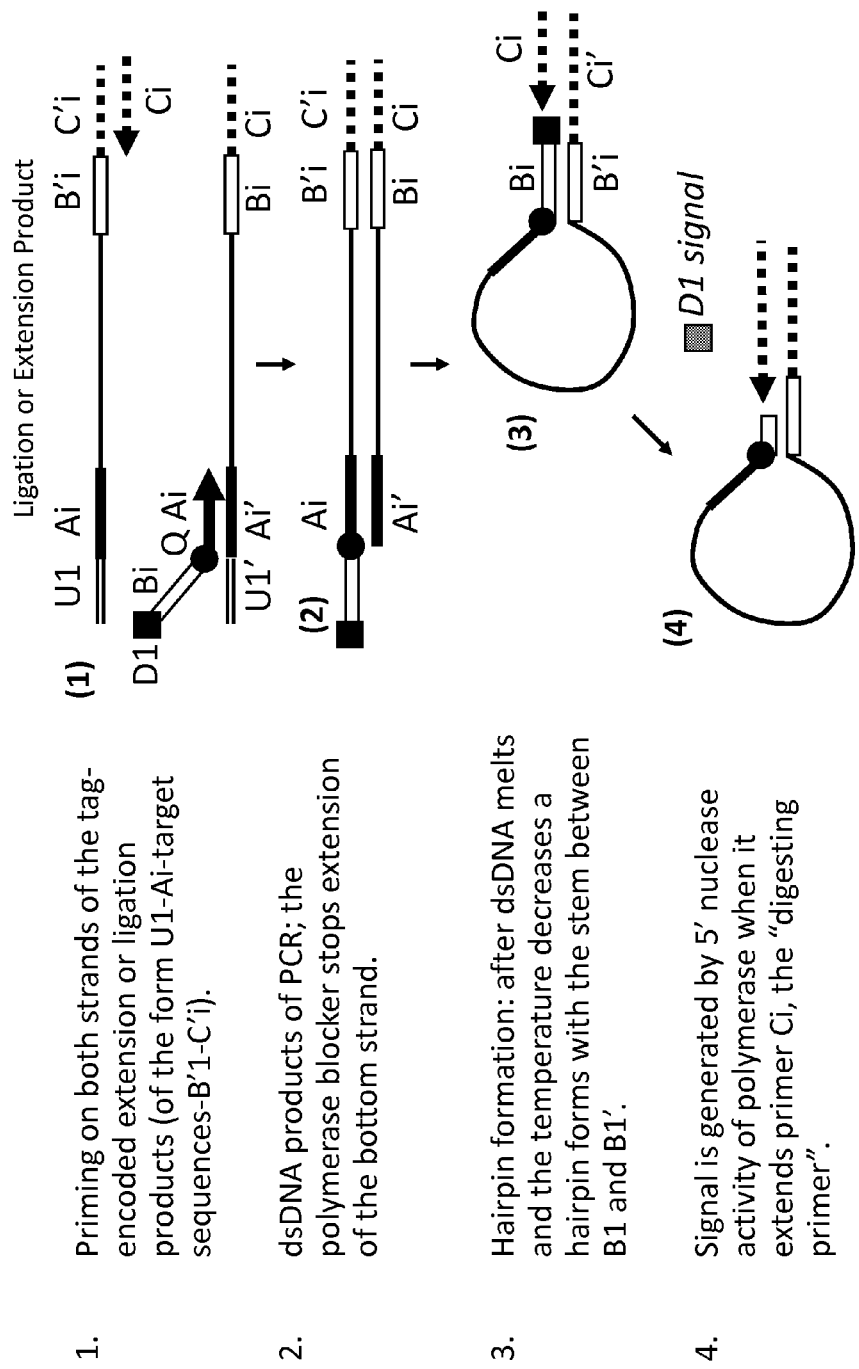
FIGS. 8A-8C show three examples for PCR detection of nuclease-ligase products of the present invention using UniTaq mediate hairpin (FIG. 8A), UniTaq 5' nuclease (aka Taqman®) probes (FIG. 8B), and UniTaq circle detection (FIG. 8C).
Figures 8B, 8C:
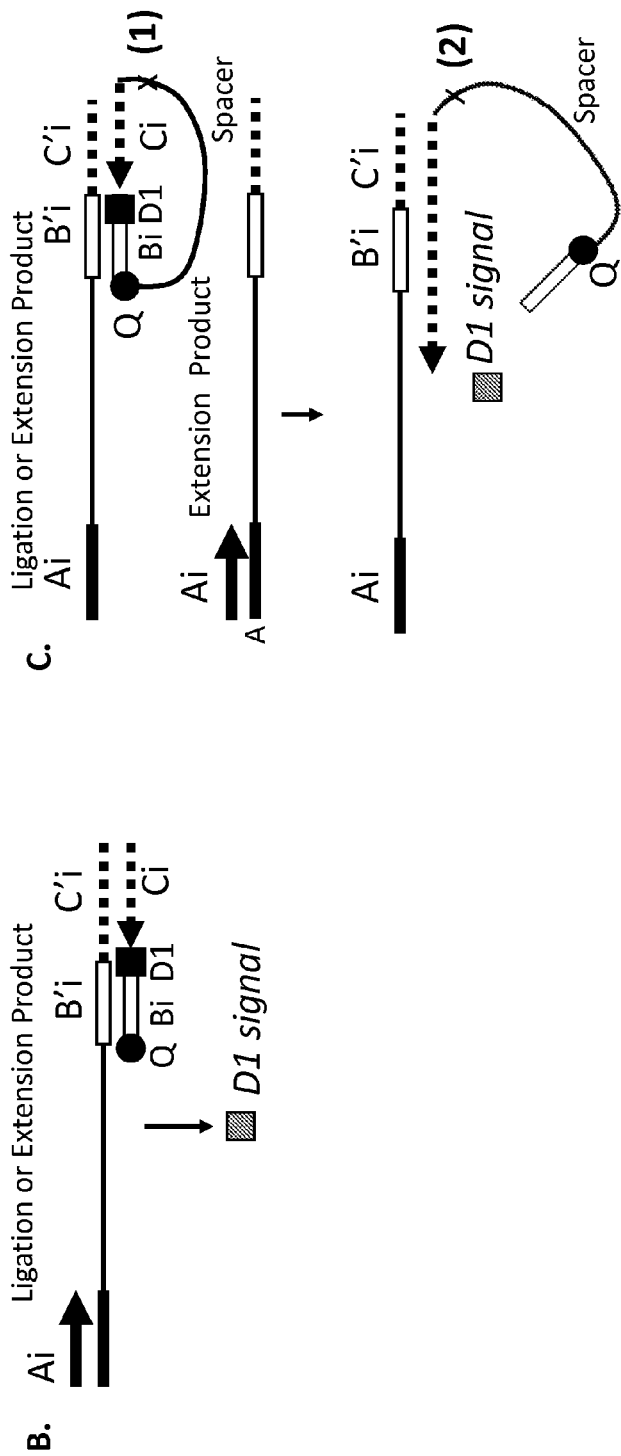

FIGS. 8A-8C show various ways in which the UniTaq tag system can be incorporated into the restriction endonuclease-ligation-PCR process of the present invention. In the first approach, shown in FIG. 8A, the primary extension product contains a first primer-specific portion, U1-Ai, where U1 is a universal primer-specific portion and Ai is a unique UniTaq product specific primer portion. The primary extension product also contains B'i (a UniTaq detection portion), and C'i (a second primer-specific portion), which are introduced into the primary extension products via the second oligonucleotide primer of the primary primer set. The primary extension products are primed on both strands using a secondary oligonucleotide primer set that comprises a first secondary oligonucleotide primer having the same nucleotide sequence as Ai, and a second oligonucleotide primer that is complementary to C'i (i.e., Ci). The first secondary oligonucleotide primer also includes a UniTaq detection probe (Bi) that has a detectable label D1 on one end and a quencher molecule (Q) on the other end (D1-Bi-Q-Ai). Optionally positioned proximal to the quencher is a polymerase blocking unit, e.g., HEG, THF, Sp-18, or any other blocker known in the art that is sufficient to stop polymerase extension. A polymerase blocker may not be required if the 5'-tail that folds into a stem has one or more bases at the 5' end that are not complementary to the middle universal tag sequence, so that the hairpin formed by the opposite strand of DNA (with the 3'-end at the end of the stem) is not extendable during PCR. One can also design a small hairpin into the 5' portion of the first secondary primer, so that the dye and the quencher are brought closer together, similar to "Sunrise" primers and probes to improve quenching and decrease background fluorescence. For example, see U.S. Pat. Nos. 5,866,336 and 6,270,967, which are hereby incorporated by reference in their entirety.

PCR amplification using the second oligonucleotide primer set generates the double stranded product shown in FIG. 8A, step 2. In this example, a polymerase blocking unit prevents a polymerase from copying the 5' portion (Bi) of the first universal primer, such that the complementary strand (i.e., bottom strand) of product cannot form a hairpin when it becomes single-stranded. Formation of such a hairpin would result in the 3' end of the stem annealing to the amplicon such that polymerase extension of this 3' end would terminate the PCR reaction.

The double stranded PCR products are melted (e.g., by raising the temperature to approximately 95° C.) to separate the upper strand from the lower strand, and when the temperature is subsequently decreased, the upper strand of product forms a hairpin having a stem between 5' portion (Bi) of the first secondary oligonucleotide primer and portion B'i at the opposite end of the strand (FIG. 8A, step 3). Also during this step, the second oligonucleotide primer (Ci) anneals to the 5'-primer specific portion (C'i). Intra-molecular hairpin formation occurs rapidly and is driven by thermodynamics: the free energy is determined by stem length, GC-content and loop length. It is important that the melting temperature (Tm) of the hairpin be significantly higher (e.g., approximately 10° C. or higher) than the Tm of the second oligonucleotide primer. This way, when the temperature is decreased, nearly 100% of the molecules will form the hairpin before the second oligonucleotide primer anneals and is extended. Upon extension of the second secondary primer in step 4, 5' nuclease activity of the polymerase cleaves the detectable label (D1) or the quencher molecule (Q) from the 5' end of the amplicon, thereby increasing the distance between the label and the quencher or FRET dye and permitting detection of the label.

In the approach shown in FIG. 8B, a traditional Taqman™ type assay is used to detect the ligation product. This method involves providing a UniTaq detection probe (Bi) that is complementary to the UniTaq detection portion (B'i). The UniTaq detection probe comprises a quencher molecule (Q) and a detectable label (D1) that are separated from each other. The UniTaq detection probe (Bi) hybridizes to its complementary UniTaq detection portion on the extension product at the same time the second oligonucleotide primer (Ci) hybridizes to the 5' C'i primer-specific portion of the primary extension product during a secondary PCR reaction.

Extension of the second oligonucleotide primer (Ci) generates a signal by 5' exonuclease cleavage of D1, separating D1 from the quencher.

A further exemplary detection format involves the formation of a universal circle as schematically illustrated in FIG. 8C. As above, the primary extension product in FIG. 8C contains a first primer-specific portion (Ai), target-specific digestion product portion, a UniTaq detection portion (B'i), and a second primer-specific portion (C'i). The extension product is amplified using a first oligonucleotide primer (Ai) that has the same nucleotide sequence as the Ai primer specific portion of the extension product, and a second oligonucleotide primer that includes (i) a primer portion (Ci) that is complementary to the 5' C'i primer specific portion of an extension product, (ii) a spacer region containing a polymerase blocker (x), (iii) a quencher molecule (Q), (iv) a UniTaq detection probe (Bi), and (v) a detectable label (D1) that is quenched when in close proximity to the quencher molecule. During a PCR reaction using these primers, the primer portion of the second oligonucleotide primer (Ci) anneals to its corresponding primer-specific portion of the extension product while the UniTaq detection probe (Bi) hybridizes to its complementary UniTaq detection portion of the extension product (FIG. 8C, Step 1). In this example, extension of the second oligonucleotide primer (FIG. 8C, Step 2) cleaves the hybridized UniTaq detection probe (Bi) thereby releasing the detectable label. The release of the detectable label from the quencher molecule generates a detectable signal.

Another aspect of the present invention is directed to a method for identifying, in a sample, one or more target nucleic acid molecules differing from other nucleic acid molecules in the sample by one or more unmethylated residues. This method involves providing a sample containing one or more target nucleic acid molecules potentially containing one or more unmethylated residues and subjecting the one or more target nucleic acid molecules in the sample to a methylation sensitive enzyme digestion that digests unmethylated, but not methylated nucleic acid molecules to form a plurality of digestion products comprising one or more unmethylated residues. A plurality of oligonucleotide adapter sets are provided, each oligonucleotide adapter set comprising (a) a first oligonucleotide adapter having a 3' end configured to ligate to a 5' end of a digestion product and hybridized to its complement, wherein the complement of the 3' end is coupled to a region complementary to a 5' portion of a digestion product and (b) a second oligonucleotide adapter having a 5' end configured to ligate to a 3' end of a digestion product and hybridized to its complement, wherein the complement of the 5' end is coupled to a region complementary to a 3' portion of a digestion product. The digestion products are subjected to a ligation reaction comprising a denaturation treatment to form single-stranded digestion products, a hybridization treatment, wherein the single-stranded digestion products hybridize to their complementary regions of the first and second oligonucleotide adapters of an oligonucleotide adapter set in a sequence-specific manner such that the 3' end of the first adapter is adjacent to the 5' end of the single-stranded digestion product and the 5' end of the second adapter is adjacent to the 3' end of the single-stranded digestion product, and a ligation treatment, wherein the oligonucleotide adapters ligate to their hybridized single-stranded digestion products thereby forming dual adapter tagged digestion products. The dual adapter tagged digestion products are detected, thereby identifying one or more target nucleic acid molecules differing from other nucleic acid molecules in the sample by one or more unmethylated residues.

Figure 9A:
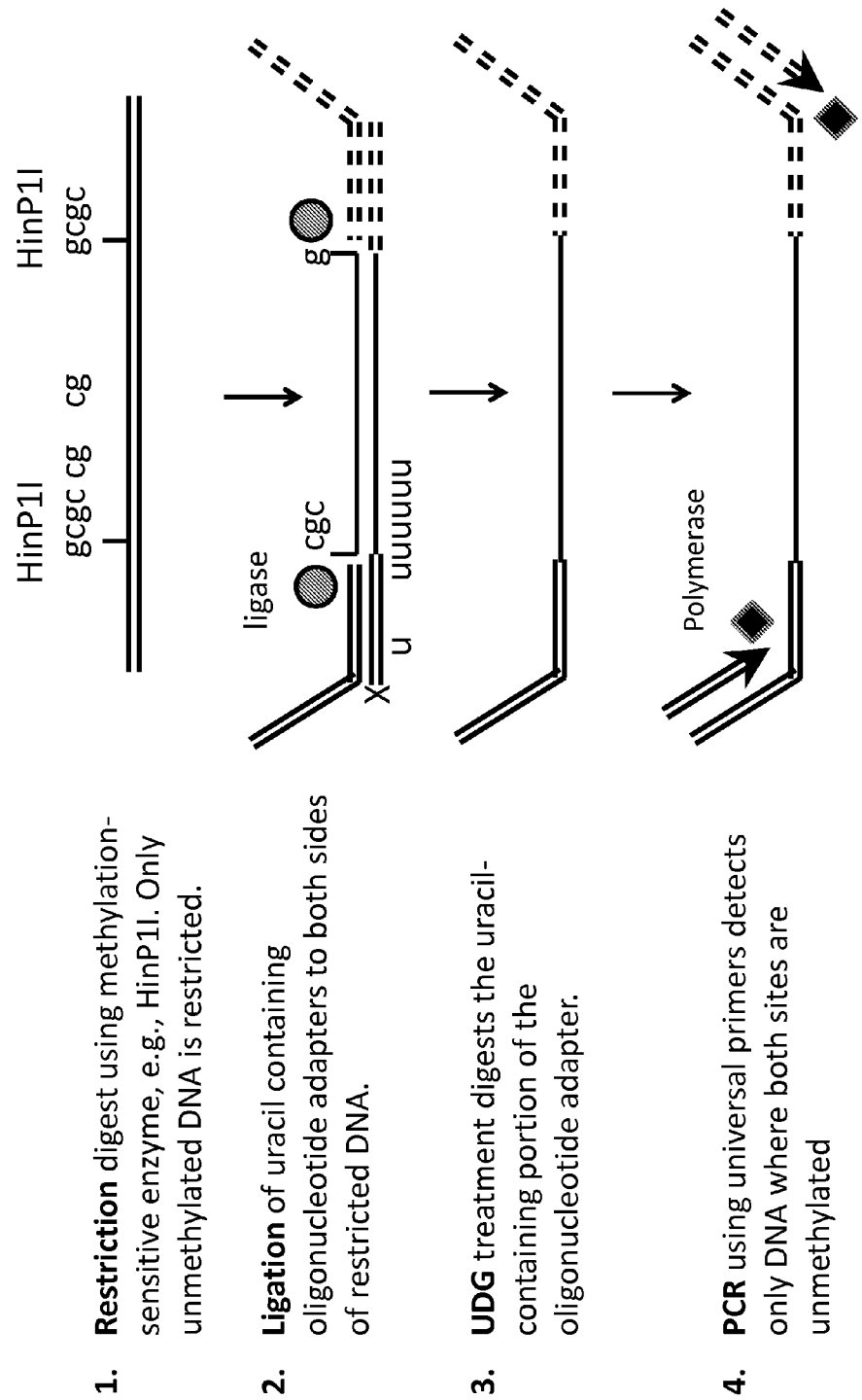

FIGS. 9A-9B depict two embodiments of this aspect of the present invention. As shown in FIG. 9A (step 1), double-stranded target DNA is cleaved by methylation sensitive restriction enzyme(s) (e.g., HinP1I) to produce unmethylated digestion products (i.e., the restriction endonuclease recognition sites on the 5' and 3' end of the digestion products are not methylated). Suitable methylation sensitive restriction enzymes are disclosed supra. dsDNA digested fragments are denatured, generating single-stranded digestion products having a unique ligation competent 5' $PO_4$ as well as a unique ligation competent 3'OH that are suitable for ligation to first and second oligonucleotide adapters, respectively. Single stranded DNA that is present in the sample is not digested by the methylation sensitive restriction enzymes and will not generate such 5' phosphate or 3' OH ligation competent ends. A plurality of oligonucleotide adapter sets are added, each oligonucleotide adapter set comprising a first oligonucleotide adapter having a 3' end configured to ligate to a 5' end of a digestion product, where the 3' end is hybridized to its complement. The complement of the 3' end of the first oligonucleotide adapter is coupled to a region complementary to a 5' portion of the digestion product. The second oligonucleotide adapter of an adapter set has a 5' end configured to ligate to a 3' end of a digestion product and is hybridized to its complement. The complement of the 5' end of the second oligonucleotide adapter is coupled to a region complementary to a 3' portion of a digestion product. As shown in FIG. 9A, the complement of the 3' end of the first adapter that is coupled to the region complementary to a 5' portion of the digestion product and/or the complement of the 5' end of the second adapter that is coupled to a region complementary to a 3' portion of the digestion product comprise uracil containing oligonucleotides. The single-stranded digestion products arising from the methylation sensitive restriction endonuclease digestion hybridize to complementary regions of the first oligonucleotide adapters in a sequence-specific manner such that the 3' end of the first adapter is adjacent to the 5' phosphorylated end of the single-stranded digestion product (FIG. 9A, Step 2). Likewise, the digestion products also hybridize to complementary regions of the second oligonucleotide adapters in a sequence-specific manner such that the 5' phosphorylated end of the second adapter is adjacent to the 3' OH end of the single-stranded digestion product (FIG. 9A, Step 2). In the presence of a DNA ligase, the oligonucleotide adapters ligate to their hybridized single-stranded digestion products to form dual adapter tagged digestion products. Subsequently, the hybridized uracil containing oligonucleotides are digested away using uracil DNA glycosylase (UDG) (FIG. 9A, Step 3).

As noted above, the method shown in FIG. 9A generates dual adapter tagged digestion products where both restriction endonuclease sites of the digestion product were unmethylated. In samples where at least one site is methylated or DNA is single-stranded, the same digestion does not occur and the particular digestion product is not generated. Accordingly, in the absence of the appropriate digestion product, there is no adapter ligation.

Following ligation of the oligonucleotide adapters (FIG. 9A, Step 2), the ligation products can be detected directly if either the first or second oligonucleotide adapter further comprises a detectable label (not shown). However, in many instances, especially when the target nucleic acid molecule is a low abundance target nucleic acid molecule, an optional primary PCR is performed prior to detecting as shown in FIG. 9A, Step 4. In accordance with this embodiment of the present invention, the first oligonucleotide adapter of an oligonucleotide adapter set further comprises a first primer-specific portion and the second oligonucleotide adapter of the oligonucleotide adapter set comprises a second primer-specific portion. Following ligation, the dual adapter tagged digestion products comprise the first primer specific portion, the digestion product, and the second primer-specific portion. The uracil containing portions of the oligonucleotide adapters are removed by digestion with UDG as shown in FIG. 9, step 3. As shown in FIG. 9A, step 4, PCR is performed using a primary primer set comprising (i) a first primary oligonucleotide primer comprising a nucleotide sequence that is the same as the first primer specific portion of the dual adapter tagged digestions product and (ii) a second primary oligonucleotide primer comprising a nucleotide sequence that is complementary to the second primer-specific portion of the dual adapter tagged digestions products. The plurality of dual adapter tagged digestion products, the one or more primary oligonucleotide primer sets and a first polymerase are blended to form a first polymerase chain reaction mixture. The first polymerase chain reaction mixture is subject to one or more PCR cycles comprising a denaturation treatment, a hybridization treatment, and an extension treatment to form primary extension products. In some embodiments of the present invention, the first or second oligonucleotide primer of the primary primer set may additionally comprise a detectable label. Accordingly, the unmethylated target nucleic acid molecule is identified by detecting and distinguishing labeled primary extension products.

In one embodiment of the present invention, the first and/or second oligonucleotide primers of a primer set are designed to contain a cleavable blocking group on their 3' end to enhance target-specific amplification. For example, the primers may contain a single ribonucleotide residue near their 3' end which prevents polymerase extension of the primer. Primer hybridization to complementary primer-specific portions on the dual adapter tagged digestion product forms a substrate for RNase H2, which cleaves the primer 5' to the RNA base thereby generating a 3'-OH on the primer that is capable of polymerase extension (see Dobosy et al., "RNase H-dependent PCR (rhPCR): Improved Specificity and Single Nucleotide Polymorphism Detection Using Blocked Cleavable Primers," *BMC Biotechnology* 11:80 (2011), which is hereby incorporated by reference in its entirety).

In the embodiment depicted in FIG. 9B, double-stranded target DNA is cleaved by methylation sensitive restriction enzyme(s) (e.g., HinP1I) to generate digestion products having two unmethylated restriction sites (i.e., unmethylated digestion products) (FIG. 9B, Step 1). dsDNA digested fragments are denatured, generating single-stranded digestion products having a unique ligation competent 5' $PO_4$ as well as a unique ligation competent 3'OH that are suitable for ligation to first and second oligonucleotide adapters, respectively. As depicted in this embodiment of the present invention, the 3' end and the complement of the 3' end of the first oligonucleotide adapter are coupled to permit the first oligonucleotide adapter to form a hairpin. Likewise, the 5' end and the complement of the 5' end of the second oligonucleotide adapter are coupled to permit the second oligonucleotide adapter to form a hairpin. In one embodiment, the second hairpinned oligonucleotide adapter can also have a 5' oligonucleotide flap portion containing a nucleotide sequence that is complementary to a 3' region of the second oligonucleotide adapter. The 5' oligonucleotide flap portion may contain an overlapping identical base to the base at the 3' OH of the digestion product. This overlapping identical base is subject to cleavage by a 5' nuclease, producing a ligation competent 5' end on the second oligonucleotide adapter. The "X" in the region of the second oligonucleotide adapter that is complementary to a 3' portion of the digestion product indicates a blocked 3' end, e.g., a phosphate, C3, or any other moiety that is non-extendable by a polymerase.

After denaturation, the single-stranded digestion products hybridize to their complementary regions of the first and second oligonucleotide adapters in a sequence-specific manner, respectively (FIG. 9B, step 2). Such hybridization brings the 3' end of the first oligonucleotide adapter adjacent to the 5' phosphorylated end of the single-stranded digestion product, and the 5' flap portion of the second oligonucleotide adapter to the 3' OH end of the single-stranded digestion product. As noted above, in the presence of a DNA polymerase having 5' nuclease activity, the 5' flap portion of the second oligonucleotide adapter is cleaved generating a ligation competent 5' phosphate. DNA ligase ligates the oligonucleotide adapters to their hybridized single-stranded digestion products to form dual adapter tagged digestion products. As in FIG. 9A, the ligation products can be directly detected if one of the oligonucleotide adapters is coupled to a detectable label. Alternatively, the first and second oligonucleotide adapters each further comprise a first and second primer-specific portion, respectively, and an optional PCR is performed (FIG. 9B, step 3) as described above in reference to FIG. 9A. The 5'→3' exonuclease activity of the polymerase used in this PCR step destroys the template portion of both ligated oligonucleotide adapters (i.e., the complement of the 3' end of the first oligonucleotide adapter, the region complementary to the 5' portion of the digestion product, and complement of the 5' end of the second oligonucleotide adapter, and the region complementary to a 3' portion of the digestion product). Optionally, the PCR primers may be designed to have a 3' cleavable blocking group that prevents non-specific polymerase extension of the primers when hybridized to something other than their corresponding complementary sequence on the dual adapter tagged digestion product as described supra.

It is usually desirable to occlude unligated oligonucleotide probes from the sample containing ligated product sequences prior to PCR amplification to prevent unligated probe extension and/or amplification that may generate false positive signals. One approach for occluding the unligated oligonucleotide probes in accordance with this aspect of the present invention is to incorporate the 5' flap portion of the second oligonucleotide adapter. In the absence of ligation the 5' flap portion hybridizes back onto its complementary 3' region of the second oligonucleotide adapter forming a hairpin that will extend on itself precluding any amplification. An alternative approach for avoiding target independent signal arising from non-ligated adapters is to incorporate an exonuclease digestion step after ligation and prior to PCR amplification (L-H Guo and R. Wu, *Methods in Enzymology* 100:60-96 (1985). All circularized ligated products are protected from cleavage by the exonuclease, while unligated adapter oligonucleotides and other non-ligated target fragments are digested by the exonuclease.

Another aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues, and subjecting the one or more target nucleic acid molecules in the sample to at least one methylation insensitive enzyme digestion reaction and at least one methylation sensitive enzyme digestion reaction to form a plurality of digestion products comprising one or more methylated uncleaved restriction sites. A plurality of oligonucleotide adapter sets are provided, each oligonucleotide adapter set comprising (a) a first oligonucleotide adapter having a 3' end configured to ligate to a 5' end of a digestion product and hybridized to its complement, wherein the complement of the 3' end is coupled to a region complementary to a 5' portion of a digestion product and (b) a second oligonucleotide adapter having a 5' end configured to ligate to a 3' end of a digestion product and hybridized to its complement, wherein the complement of the 5' end is coupled to a region complementary to a 3' portion of a digestion product. The digestion products are subject to a ligation reaction comprising a denaturation treatment to form single-stranded digestion products, a hybridization treatment, wherein the single-stranded digestion products hybridize to their complementary regions of the first and second oligonucleotide adapters of an oligonucleotide adapter set in a sequence-specific manner such that the 3' end of the first adapter is adjacent to the 5' end of the single-stranded digestion product and the 5' end of the second adapter is adjacent to the 3' end of the single-stranded digestion product, and a ligation treatment, wherein the oligonucleotide adapters ligate to their hybridized single-stranded digestion products thereby forming dual adapter tagged digestion products. The dual adapter tagged digestion products are detected, thereby identifying one or more target nucleic acid molecules differing from other nucleic acid molecules in the sample by one or more methylated residues.

FIG. 9C depicts an embodiment of this aspect of the present invention. In this figure, double-stranded target DNA is cleaved by one or more methylation insensitive enzymes to form fragments having at least one internal methylation sensitive restriction site (FIG. 9C, Step 1). The double-stranded target DNA is further cleaved with one or more methylation sensitive enzymes to generate a plurality of digestion products containing one or more internal uncleaved methylated restriction sites (FIG. 9C, Step 1). The oligonucleotide adapters depicted in this figure are hairpinned as describe in FIG. 9B and further coupled to each other (i.e., the 5' end of the first oligonucleotide adapter is coupled to the 3' end of the second oligonucleotide adapter) (FIG. 9C, Step 2). The coupled adapters comprise a polymerase blocking group ("X"). This blocking group interferes with polymerase extension of an unligated first adapter, but does not interfere with the 5'→3' exonuclease activity of polymerase in the subsequent extension of ligation products. The second oligonucleotide adapter may optionally contain a 5' flap portion that is cleaved by the nuclease activity of a polymerase after hybridization of the second oligonucleotide adapter to the digestion product and prior to ligation.

As shown in FIG. 9C, step 2, the coupled oligonucleotide adapters hybridize to their corresponding digestion product in a sequence specific manner, bringing the 3' end of the first oligonucleotide adapter adjacent to the 5' end of the digestion product and the 5' flapped end of the second oligonucleotide adapter adjacent to the 3' end of the digestion product. The 5' flap on the second oligonucleotide is cleaved when it comprises a nucleotide that overlaps and is identical to the nucleotide on the 3' of the digestion product. In the absence of this cleavage, the 5' flap hybridizes back on a 3' complementary region of the second oligonucleotide adapter to inhibit priming of the unligated adapter. DNA ligase ligates the first and second coupled adapters to the digestion product such that the 5' end of the digestion product is coupled to the 3' end of the digestion product (FIG. 9C, Step 2).

As noted above, the ligation products formed in FIG. 9C, Step 2 can be directly detected when at least one of the oligonucleotide adapters is coupled to a detectable label. Alternatively, the first and second oligonucleotide adapters each further comprise a first and second primer-specific portion respectively, and an optional PCR is performed (FIG. 9C, step 3) as described above in reference to FIG. 9A. The 5'→3' exonuclease activity of the polymerase used in this PCR destroys the template portion of both ligated oligonucleotide adapters (i.e., the complement of the 3' end of the first oligonucleotide adapter, the region complementary to the 5' portion of the digestion product, and complement of the 5' end of the second oligonucleotide adapter, and the region complementary to a 3' portion of the digestion product). Optionally, the PCR primers may be designed to have a 3' cleavable blocking group that prevents non-specific polymerase extension of the primers when hybridized to something other than their corresponding complementary sequence on the dual adapter tagged digestion product as described supra.

As described supra, an exonuclease digestion step can be included after ligation and prior to PCR amplification of the ligation products to destroy unligated adapter oligonucleotides.

While FIGS. 9A and 9B depict methods for detecting unmethylated residues within a sample (i.e., the double stranded DNA is only digested with a methylation-sensitive enzyme), and FIG. 9C shows a method for detecting methylated residues with in a sample (i.e., the double stranded DNA is digested with both methylation sensitive and methylation insensitive enzymes), one of skill in the art readily would appreciate that the various oligonucleotide adapter designs shown in FIGS. 9A-9C can be used in either method. In other words, the uracil containing oligonucleotide adapters of FIG. 9A and the hairpinned non-coupled oligonucleotide adapters of FIG. 9B can be utilized in a method to detect methylated residues, and the hairpinned coupled oligonucleotide adapters shown in FIG. 9C can be utilized in a method to detect unmethylated residues.

Figure 9D:
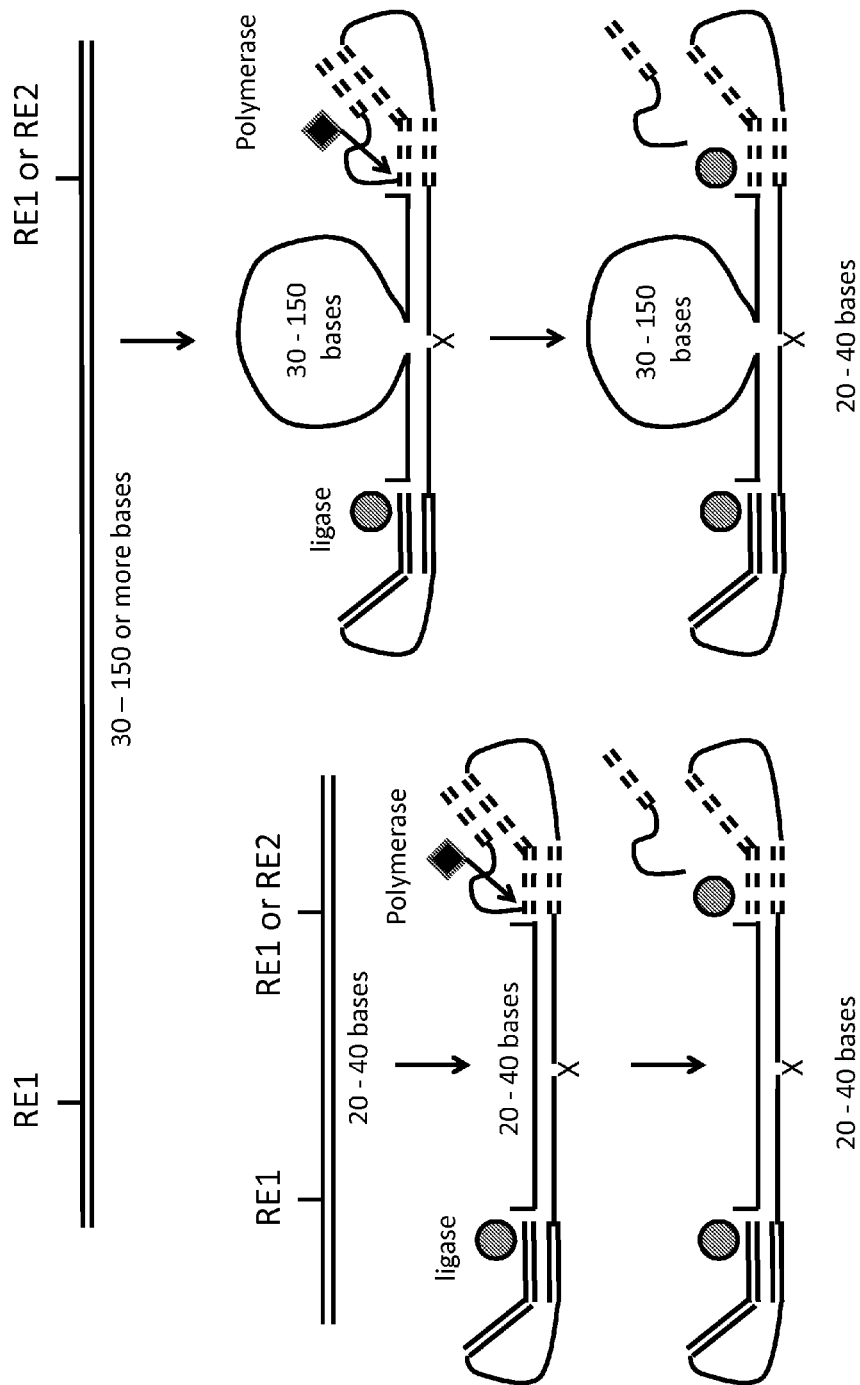

FIG. 9D shows the applicability of the restriction endonuclease-ligation-PCR method of the present invention for detecting target fragments of about 20-40 bases (FIG. 9D, left-hand side) or about 30-150 or more bases (FIG. 9D, right-hand side). Signal is generated only if specific fragments where both sites are either (i) methylated or (ii) unmethylated are generated, thereby generating a specific 5' phosphorylated end and a specific 3' end suitable for ligation.

The processes described in FIG. 9A include the following four steps: (i) restriction of double-stranded DNA to generate unique 5' phosphate and 3'OH groups, (ii) ligation of oligonucleotide adapters to both the 5' and 3' ends of uniquely generated digestion products, (iii) removal of template strand, for example by UDG digestion of uracil-containing oligonucleotides, and (iv) use of universal primers to PCR amplify products suitable for subsequent detection and quantification. As such, the processes described in FIGS. 1A, 1B, and 9A, or any combination thereof, may be performed on the same sample simultaneously, allowing for accurate identification and quantification of both low abundance methylated and unmethylated targets in the same reaction. Likewise, the processes described in FIGS. 9B, 9C, and 9D include the same three steps: (i)

restriction of double-stranded DNA to generate unique 5' phosphate and 3'OH groups, (ii) ligation of oligonucleotide adapters to both the 5' and 3' ends of uniquely generated digestion products, and (iii) use of universal primers to PCR amplify products suitable for subsequent detection and quantification. As such, the processes described in FIGS. 2A, 2B, 9B, 9C, and 9D, or any combination thereof, may be performed on the same sample simultaneously, allowing for accurate identification and quantification of both low abundance methylated and unmethylated targets in the same reaction.

The ligated product sequences or primary extension product thereof that are formed in accordance with the aspects of the present invention depicted in FIGS. 9A-9D can be detected and distinguished in a number of ways. As described above, one of the oligonucleotide adapters of an adapter set may be coupled to a detectable label to facilitate detection of the ligation product. In another embodiment, the oligonucleotide adapters of an adapter set comprise first and second primer-specific portions to facilitate the formation of primary extension products which can be directly detected using labeled PCR primers. In another embodiments, the oligonucleotide adapters further comprise a zip-code portion or UniTaq detection portion, which facilitates detection via one or more alternative methods as described in more detail below.

In one embodiment of the present invention, one or both of the first or second oligonucleotide adapters of an adapter set further comprise a zip-code portion. As described above, a zip-code is a short nucleotide sequence, e.g., between 16 to 24 nucleotides in length, that has no sequence identity to the target nucleotide sequence, and, preferably, little or no sequence identify to any genomic nucleotide sequence. Zip-codes hybridize to complementary capture oligonucleotides from a collection of capture oligonucleotides as also described above.

Detection using the zipcode can be carried out using traditional Taqman™ detection which is described above in reference to FIG. 5 (see U.S. Pat. No. 6,270,967 to Whitcombe et al., and U.S. Pat. No. 7,601,821 to Anderson et al., which are hereby incorporated by reference in their entirety). In accordance with this embodiment, the first oligonucleotide adapter comprises a first primer-specific portion, and the second oligonucleotide adapter comprises a second primer-specific portion. Additionally, either the first or second oligonucleotide adapter of the adapter set further contains a zip-code portion. Following ligation, the dual adapter tagged digestion products comprise the first primer-specific portion, the zip-code portion, the digestion product portion, and the second primer-specific portion. The dual adapter tagged digestion products can be detected by providing a collection of capture oligonucleotides, where each capture oligonucleotide comprises a quencher molecule and a detectable label that are separated from each other (i.e., the Taqman™ probe). In one approach, the collection of capture oligonucleotides is blended with the dual adapter tagged digestion products, a primary oligonucleotide primer set as described above in reference to FIG. 9A (i.e., comprising a first oligonucleotide primer having a nucleotide sequence that is the same as the first primer-specific portion of the dual adapter tagged digestion product and a second oligonucleotide primer having a nucleotide sequence that is complementary to the second primer-specific portion of the dual adapter tagged digestion product), and a polymerase to form a first polymerase chain reaction mixture. The capture oligonucleotides of the collection hybridize to their complementary zip-code portions of the dual adapter tagged digestion products or complements thereof during the hybridization treatment of the first PCR. The quencher molecule and/or the detectable label are cleaved from the hybridized capture oligonucleotides during the extension treatment of the PCR, and the detectable label, separated from the quencher molecule, is detected. In an alternative embodiment, which is shown in FIG. 5, dual tagged ligation products are subject to the first PCR reaction in the absence of the collection of capture oligonucleotide probes. The primary extension products formed from the first PCR are then blended with the collection of capture oligonucleotide probes, a secondary oligonucleotide primer set that is capable of hybridizing to the primary extension products, and a second polymerase to form a second PCR. This approach is particularly suitable when detecting low abundance target nucleic acid sequences. The capture oligonucleotides of the collection hybridize to their complementary zip-code portions of the primary extension products and the secondary oligonucleotide primers likewise hybridize to the primary extension products. Extension of the secondary primer cleaves the quencher molecule and/or the detectable label from the hybridized capture oligonucleotides during the extension treatment of the PCR, and the detectable label, separated from the quencher molecule is detected.

In yet another approach, the dual adapter digestion products or the primary extension products, thereof may further contain one or more unique sequences (ranging from 0 to 10 bases) internal to the first and second primer-specific portion (Unique Ai, Unique Bi), represented as follows.

Primer Portion 1-Unique Ai-Zipcode Zi-Target DNA-Unique Bi-Primer Portion 2

These unique sequences are introduced via the first and second oligonucleotide adapters. For detection using Zipcode Taqman assays, the sample is diluted 10- to 100-fold after the 8-20 cycles of universal amplification, and more unique primers that overlap with the Unique Ai and the Unique Bi sequence are added for each product. The Taqman probe is a capture oligonucleotide that is complementary to the zipcode sequence.

Another detection approach utilizing zipcodes involves having the zipcode portion split into two parts, which are brought in proximity to each other using a short region of complementary sequence on both sides of the split zipcode parts as described above in reference to FIG. 6 and FIG. 7.

In accordance with this aspect of the present invention and in reference to FIG. 6, the first oligonucleotide adapter of an adapter set comprises a first primer-specific portion (U1 and A1), a first portion of the zip-code (Z1.1') and a first tag portion (T1) that is 3' to the first zip-code portion. The second oligonucleotide adapter of an adapter set comprises a second portion of the zip-code (Z1.2'), a second tag portion (T1') that is 5' to the second zip-code portion, and the second primer-specific portion (B1-U2). The resulting dual adapter tagged digestion products contain the (i) first primer-specific portion, U1-A1, where U1 is a universal primer specific portion and A1 is a unique, target-specific primer portion, (ii) the first zip-code portion (Z1.1'), (iii) the first tag portion (T1), (iv) the digestion product portion, (v) the second tag portion (T1'), (vi) the second portion of the zip-code (Z1.2'), and (vii) the second primer specific portion, B1-U2, where Bi is a unique, target-specific primer portion and U2 is a universal primer portion.

As shown in FIG. 6, step 1, the A1 and B1 unique sequences serve to facilitate a target-specific PCR amplification of the dual adaptor tagged digestion products when the PCR primers that are utilized span the universal primer portion and the A1 and B1 portions, respectively. This target-specific PCR amplification can optionally be preceded by a universal PCR amplification reaction using primers that hybridize to the 5' and 3' universal primer-specific portions. A first universal amplification reaction is particularly suitable when detecting low abundance target nucleic acid sequences in a sample.

Following the target-specific PCR amplification of the dual tagged digestion products or primary extension products thereof (FIG. 6, Step 1), the double stranded DNA extension products are denatured (FIG. 6, Step 2). As the temperature decreases, the first and second tag portions (T1 and T1') transiently hybridize together, bringing the first portion of the zipcode sequence (Z1.1' from the first oligonucleotide adapter) in proximity to the second zipcode sequence (Z1.2' from the second oligonucleotide adapter). The transient hybridization is stabilized by the simultaneous hybridization of a labeled capture oligonucleotide (Z1) that is complementary to the adjacently positioned zipcode sequences (i.e., Z1.1' and Z1.2'; FIG. 6, Step 3). In one embodiment, the capture oligonucleotide has a quencher molecule (Q) and a detectable label (F) that are separated from each other, where the detectable label is quenched when in close proximity to the quencher molecule. Signal is generated by 5' nuclease activity of a polymerase as it extends a primer (i.e., the "digesting primer") that is bound to the universal primer-specific portion (U2), the unique B1 portion, or a combination thereof, and cleaves the hybridized capture oligonucleotide. Primer extension cleaves the detectable label from the capture oligonucleotide releasing the detectable label from the quencher molecule, enabling detection (FIG. 6, Step 4). As soon as polymerase has traversed Z1.2', the short stem between Z1.2' and Z1.1' falls apart and polymerase continues extending to create the dsDNA product. A wide variety of detectable labels, i.e., fluorescent dyes are known in the art and commercially available for use in this embodiment of the present invention, e.g., FAM, TET, JOE, VIC, HEX, CY3, TAMRA, TexasRed, CY5, ROX. Similarly, quencher molecules, e.g., MGB-NFQ, BHQ-[0123], ZEN quencher from IDT, are also well known to those skilled in the art and available for use in this embodiment of the present invention.

FIG. 7 shows the other example of split zipcode hairpin detection. In this figure, the dual adapter digestion products are formed from a first oligonucleotide adapter having a first primer-specific portion (U1 and A1), a first portion of the zip-code (Z1.1') and a first tag portion (T1) that is 3' to the first zip-code portion. The second oligonucleotide adapter of the oligonucleotide adapter set comprises a second portion of the zip-code (Z1.2'), a second tag portion (T1') that is 5' to the second zip-code portion, and the second primer-specific portion (U2). The resulting dual adapter tagged digestion products as shown in step 1 of FIG. 7, contain the (i) first primer-specific portion, U1-A1, where U1 is a universal primer specific portion and A1 is a unique, target-specific primer portion (i.e., a third-primer portion), (ii) the first zip-code portion (Z1.1'), (iii) the first tag portion (T1), (iv) the digestion product portion, (v) the second tag portion (T1'), (vi) the second portion of the zip-code (Z1.2'), and (vii) the second primer specific portion (U2).

In Step 1 of FIG. 7, the dual adapter tagged digestion products are optionally initially amplified using a universal oligonucleotide primer set that binds to the U1 and U2 primer portions of the dual adapter tagged digestion products. The primary extension products formed from this universal PCR step are subject to a secondary PCR step (FIG. 7, step 2) using a secondary primer set that includes a first secondary oligonucleotide primer having (a) a nucleotide sequence that is the same as the A1 primer portion (A1), (b) a capture oligonucleotide portion (Z1) that is complementary to adjacently positioned first and second zip-code portions of an oligonucleotide probe set, (c) a quencher molecule (Q) and a detectable label (F) separated by said capture oligonucleotide portion. The second secondary oligonucleotide primer (U2) of the primer set has the same nucleotide sequence as the second primer specific portion of the second primary oligonucleotide primer. The quencher molecule of the first secondary primer can serve as a polymerase blocker to block polymerase extension of the bottom strand. Alternatively, a polymerase blocker such as HEG (hexethylene glycol), THF (tetrahydrofuran), Sp-18, or any other blocker known in the art that is sufficient to stop polymerase extension can be positioned proximal to the quencher moiety. The double stranded DNA products (shown in FIG. 7, Step 3) are denatured and the temperature decreased to allow dual hairpin formation with stems between Z1.1' and Z1.2' (stem formed by hybridization between T1 and T1') and between the capture oligonucleotide portion (Z1) and Z1.1'/Z1.2' (FIG. 7, Step 4). Signal is generated by 5' nuclease activity of polymerase when it extends a "digesting primer" complementary to the 5' universal primer-specific portion. Primer extension cleaves the detectable label (F) or the quencher molecule (Q) from the capture oligonucleotide releasing the detectable label (F) from the quencher molecule (Q), enabling detection (FIG. 7, Step 5). As soon as polymerase has traversed Z1.2', the short stem between Z1.2 and Z1.1' falls apart and polymerase continues extending until it comes to the polymerase blocker to create a dsDNA product similar to that in step 1, but lacking the fluorescent signal.

An alternative approach to utilizing the zipcode/capture oligonucleotide sequences for detection involves the UniTaq approach described supra.

FIGS. 8A-8C show various ways in which the UniTaq tag system can be incorporated into the dual adapter tagged digestion products formed using the nuclease-ligation-PCR process of the present invention. In each of these approaches, which are described in detail above, the first oligonucleotide adapter of an adapter set comprises a first primer-specific portion (U1 or U1-Ai), and the second oligonucleotide adapter of an adapter set comprises UniTaq detection portion (B'i) and a second primer-specific portion (C'i). Accordingly, and as depicted in the embodiment shown in FIG. 8A, the dual tagged digestion products contain (i) a first primer-specific portion, U1-Ai, where U1 is a universal primer-specific portion and Ai is a unique, UniTaq specific primer portion, (ii) the digestion product, (iii) a UniTaq detection portion (B'i), and (iv) a second primer-specific portion (C'i). In FIG. 8A step 1, primary extension products of the dual tagged digestion products that were formed in an initial universal PCR reaction, are primed using a secondary oligonucleotide primer set that comprises a first secondary oligonucleotide primer having the same nucleotide sequence as Ai, and a second oligonucleotide primer that is complementary to C'i (i.e., Ci). The first secondary oligonucleotide primer also includes a UniTaq detection probe (Bi) that has a detectable label D1 on one end and a quencher molecule (Q) on the other end (D1-Bi-Q-Ai). Optionally positioned proximal to the quencher is a polymerase blocking unit, e.g., HEG, THF, Sp-18, or any other blocker known in the art that is sufficient to stop polymerase extension.

One of skill in the art would readily appreciate that the dual adapter tagged digestion products can be the starting material in FIG. 8A, step 1 (i.e., denoted as "ligation product"), instead of the primary extension products.

PCR amplification of the primary extension products of the dual adapter tagged digestion products using the second oligonucleotide primer set generates the double stranded extension products shown in FIG. 8A, step 2. Detection of the PCR products produced with the secondary oligonucleotide primer set proceeds as described supra with regard to FIG. 8A steps 2-4.

In the approach shown in FIG. 8B, a traditional Taqman™ assay is used to detect the dual adapter tagged digestion products as described in detail above. The starting material in FIG. 8B, Step 1, can be the dual adapter tagged digestion product ("ligation product") or primary extension products thereof formed in a first universal PCR. Likewise, the detection format shown in FIG. 8C and described in detail above can also be used to detect dual adapter tagged digestion products. One of skill in the art readily appreciates that the starting material in FIG. 8C, Step 1, can be the dual adapter tagged digestion product ("ligation product") or primary extension products thereof formed in a first universal PCR.

The challenge to developing reliable diagnostic and screening tests based on changes in DNA methylation, is to distinguish those markers emanating from the tumor or fetus that are indicative of disease (i.e. early cancer) vs. presence of the same markers emanating from normal tissue. There is also a need to balance the number of markers examined and the cost of the test, with the specificity and sensitivity of the assay. This is a challenge that needs to address the biological variation in diseases such as cancer. In many cases the assay should serve as a screening tool, requiring the availability of secondary diagnostic follow-up (i.e. colonoscopy, amniocentesis).

Compounding the biological problem is the need to reliably detect changes in DNA methylation in a very small number of initial cells (i.e., from CTCs), or when the cancer or fetus-specific signal is in the presence of a majority of nucleic acid emanating from normal cells.

Finally, there is the technical challenge to distinguish true signal resulting from detecting the desired disease-specific nucleic acid methylation marker vs. false signal generated from normal nucleic acids present in the sample vs. false signal generated in the absence of the disease-specific nucleic acid methylation marker.

The methods of the present invention described herein provide solutions to these challenges. These solutions share some common themes highlighted below.

The first theme is multiplexing. PCR works best when primer concentration is relatively high, from 50 nM to 500 nM, limiting multiplexing. Further, the more PCR primer pairs added, the chances of amplifying incorrect products or creating primer-dimers increase exponentially. In contrast, for ligation detection reaction (LDR) probes, low concentrations on the order of 4 nM to 20 nM are used, and probe-dimers are limited by the requirement for adjacent hybridization on the target to allow for a ligation event. Use of low concentrations of gene-specific PCR primers or LDR probes with universal primer sequence "tails" allows for subsequent addition of higher concentrations of universal primers to achieve proportional amplification of the initial PCR or LDR products. Herein, the traditional LDR approach is flipped by using oligonucleotide adapters as templates to capture and append specific tags to very low-abundance single-stranded target fragments.

The second theme relates to fluctuations in signal due to low input target nucleic acids. Often, the target nucleic acid originated from a few cells, either captured as CTCs, or from tumor cells that underwent apoptosis and released their DNA as small fragments (140 to 160 bp) in the serum. Under such conditions, it is preferable to perform some level of proportional amplification to avoid missing the signal altogether or reporting inaccurate copy number due to Poisson distribution when distributing small numbers of starting molecules into individual wells (for real-time, or digital PCR quantification). As long as these initial universal amplifications are kept at a reasonable level (approximately 8 to 20 cycles), the risk of carryover contamination during opening of the tube and distributing amplicons for subsequent detection/quantification (using real-time, or droplet PCR) is minimized. If needed, carryover signal may be eliminated by standard uracil incorporation during the universal amplification step, and using UNG and AP endonuclease in the pre-amplification workup procedure. Alternatively, carryover signal may be avoided altogether by performing multiple steps in a closed system, such as plastic microfabricated "lab on a chip" devices.

The third theme is target-independent signal. This would arise from either polymerase or ligase reactions that occur in the absence of the correct target. Some of this signal may be minimized by judicious primer design. For ligation reactions, the 5'→3' nuclease activity of polymerase may be used to liberate the 5' phosphate of the downstream ligation primer (only when hybridized to the target), so it is suitable for ligation. In the invention presented herein, the specificity of methyl sensitive and methyl insensitive restriction endonucleases is used to generate ligation competent 5' phosphate and 3'OH groups at defined positions in the target.

The fourth theme is either suppressed (reduced) amplification or incorrect (false) amplification due to unused primers in the reaction. One approach to eliminate such unused primers is to capture genomic DNA on a solid support, allow ligation primers to hybridize and ligate, and then remove primers or products that are not hybridized to the genomic DNA on a solid support. Another approach is to eliminate oligonucleotide template adapter strands, either by using uracil DNA glycosylase to digest uracil-containing artificial template, or by using the 5'→3' nuclease activity of polymerase to digest the template strand of a ligated product. Still another approach is to design the upstream hairpin oligonucleotide adapter so in the absence of ligation it extends on itself and will not amplify further. Still another approach is to design the downstream hairpin oligonucleotide adapter to comprise a 5' flap that is cleaved off by the 5'→3' nuclease activity of polymerase when hybridized to the cut fragment, but uncut flap hybridizes back to a complementary region on the adapter such that it inhibits subsequent priming of an unligated oligonucleotide. Still another approach is to incorporate a blocking group within the adapter oligonucleotide that interferes with extension of the 3' end. Still another approach is to use a blocking group that prevents extension of an unligated upstream hairpinned adapter past the blocking group and therefore, avoids the generation of an amplification competent artificial template, but said blocking group does not interfere with the 5'→3' nuclease activity of polymerase to digest the template strand of a ligated product. Still another approach is to use universal primer designs on either PCR or oligonucleotide adapter primers, which are slightly shorter than Universal primers. This allows initial universal amplification at a lower cycling temperature (i.e., 55° C. annealing) followed by higher cycling temperature (i.e., 65° C. annealing) such that the universal primers bind preferentially to the desired product (compared to composite PCR or oligonucleotide adapter primers binding to incorrect products).

The methods of the present invention described herein are capable of detecting and quantifying one or more low abundance target nucleic acid molecules that have one or more methylated residues and/or one or more unmethylated residues. As used herein "low abundance target nucleic acid molecule" refers to a target nucleic acid molecule that is present at levels as low as 1% to 0.01% of the sample. In other words, a low abundance nucleic acid molecule with one or more methylated residues or one or more unmethylated residues can be distinguished from a 100 to 10,000-fold excess of nucleic acid molecules in the sample having a similar nucleotide sequence as the low abundance nucleic acid molecules but without the one or more methylated residues or with one or more methylated residues, respectively. In some embodiments of the present invention, the copy number of one or more low abundance target nucleotide sequences are quantified relative to the copy number from an excess of nucleic acid molecules in the sample having a similar nucleotide sequence as the low abundance nucleic acid molecules. In other embodiments of the present invention, the one or more low abundance target nucleotide sequences are quantified in the sample. This quantitation can be absolute or relative to other nucleotide sequences in the sample. In other embodiments of the present invention, the relative copy number of one or more target nucleotide sequences are quantified.

The low abundance target nucleic acid molecules to be detected can be present in any biological sample, including, without limitation, tissue, cells, serum, blood, plasma, amniotic fluid, sputum, urine, bodily fluids, bodily secretions, bodily excretions, cell-free circulating nucleic acids, cell-free circulating fetal nucleic acids in pregnant woman, circulating tumor cells, tumor, tumor biopsy, and exosomes.

With regard to early cancer detection, the methods of the present invention are suitable for high sensitivity methylation marker detection for promoter hypermethylation (when present at 1% to 0.01%) in methyl enriched DNA, or even total serum DNA, e.g., promoter hypermethylation in p16 and other tumor suppressor genes, CpG "islands", September 9, Vimentin, etc. The methods of the present invention are also suitable for high sensitivity unmethylated marker detection, for example, promoter hypomethylation when present at 1% to 0.1% in total serum DNA. For example, the method is useful for detecting promoter hypomethylation in potential oncogenes, CpG "shoreline" regions, and loss of methylation in Alu or other repeat sequences.

The presence and absence of methylation in certain genetic regions has prenatal diagnostic and prognostic applications. For example, aberrant methylation on regions on chromosomes 13, 18, 21, X, and Y can be used to diagnose Down Syndrome (Patsalis et al., "A New Non-Invasive Prenatal Diagnosis of Down Syndrome through Epigenetic Markers and Real-Time qPCR," Exp. Opin. Biol. Ther. 12(Suppl. 1): S155-S161 (2012), which is hereby incorporated by reference in its entirety). Because fetal DNA and maternal DNA are differentially methylated, cell-free fetal DNA in maternal plasma can provide a source of fetal DNA, which can be obtained non-invasively and utilized to assess the methylation state of the aforementioned chromosomes. Since cell-free fetal DNA only accounts for 3-6% of total DNA in maternal circulation during the first trimester, the highly sensitive methods of the present invention are particularly suitable for use in these types of non-invasive prenatal diagnostic assays. The present invention allows for non-invasive prenatal detection of chromosomal anueploidies in fetal DNA by using digital PCR to quantify methylation in chromosomal regions that are unmethylated in normal serum, and/or by using digital PCR to quantify the lack of methylation in chromosomal regions that are methylated in DNA isolated from normal serum.

PROPHETIC EXAMPLES

The following examples are provided to illustrate prophetic embodiments of the present invention but they are by no means intended to limit its scope Prophetic Example 1—Detection of Highly Sensitivity Methylation Marker for Promoter Hypermethylation (Present at 1% to 0.01%)

A number of groups have determined methylation status of both normal and tumor DNA on a genome wide scale (Irizarry et al., "The Human Colon Cancer Methylome Shows Similar Hypo- and Hypermethylation at Conserved Tissue-Specific CpG Island Shores," Nat. Genetics 41(2): 178-186 (2009), and Hinoue et al., "Genome-Scale Analysis of Aberrant DNA Methylation in Colorectal Cancer," Genome Res. 22:271-282 (2012), which are hereby incorporated by reference in their entirety). These studies inform selection of markers.

Overview of Approach:

Isolated genomic DNA, or methyl enriched DNA is treated with a cocktail of methyl sensitive enzymes (AciI, HinP1I, Hpy99I, HpyCH4IV, BstUI, HpaII, HhaI or a combination thereof), as well as by methyl insensitive enzymes (MspI, HaeIII, AluI, TaqI, HpyCH4V, HpyCH4III, BfaI, NlaIII, DdeI, BsaJI, or a combination thereof). The idea is to generate a fragment of DNA of approximately 40 bases or more, wherein the 5' phosphate of the fragment originated from a methyl insensitive enzyme. The fragment should have at least 3 methyl sensitive enzyme sites, such that cleavage would cause these fragments to dissipate. One strand of the genomic fragment is then hybridized onto an artificial template containing uracil, wherein the upstream region is unrelated to genomic DNA, and an upstream primer hybridizes to that region, and can ligate to the genomic fragment at the 5' phosphate. The template strand is then destroyed with UNG and AP endonuclease. A downstream oligonucleotide that hybridizes to the genomic fragment is now added downstream of where it hybridized to the template strand. Both upstream and downstream oligonucleotides have UniTaq specific sequences, a zipcode specific sequence, and universal sequences outside, allowing for simultaneous "preamplification" for 8-20 cycles, prior to tube opening, and dividing into the appropriate UniTaq taqman assays. For each promoter region, there will be three positions of interrogation, such it is seen when the signal appears (Ct value indicating relative quantity of methylated sequence) as well as total signal strength (i.e. =1, 2, or 3 sites methylated for that promoter).

The UNG and AP endonuclease step is needed to destroy template so that primers do not accidentally amplify just the template. By insisting on having an endonuclease generate the 5' phosphate, this avoids false signal, and should get rid of any non-specific ligation signal as well. Thus, any rare fragment of genomic DNA that was single-stranded after purification, or did not get cleaved will not form a productive substrate for subsequent PCR amplifications, as the artificial template has non-genomic sequences on both sides.

To summarize the levels of discrimination of the above approach for detection of low-abundance methylation:
1. Use of methylation insensitive restriction enzyme to generate a unique 5' phosphate on double-stranded target DNA.
2. Use of methylation sensitive restriction enzymes to cleave double-stranded target when not methylated.
3. Use of ligation fidelity of thermostable ligase to ligate correct tag to target strand on template.
4. Use of uracil DNA glycosylase to destroy template strands.
5. Use of locus specific primer and polymerase to amplify ligated target strands.

Detailed Protocol: Detection of Highly Sensitivity Methylation Marker for Promoter Hypermethylation (Present at 1% to 0.01%) in Methyl Enriched DNA or Total Serum DNA (See FIG. 1B)

Step 1: Cleave isolated genomic DNA, or methyl enriched DNA with a cocktail of methyl sensitive enzymes (AciI, HinP1I, Hpy99I, HpyCH4IV, BstUI, HpaII, HhaI or a combination thereof), as well as by methyl insensitive enzymes (MspI, HaeIII, AluI, TaqI, HpyCH4V, HpyCH4III, BfaI, NlaIII, DdeI, BsaJI, or a combination thereof). Generate fragments of approximately 40 bases or more that have a 5' phosphate from a methylation insensitive site (i.e. MspI, HaeIII, AluI, TaqI, HpyCH4V, HpyCH4III, BfaI, NlaIII, DdeI, or BsaJI), and at least one methyl sensitive sites (that are not cleaved because they were methylated). Preferably, three such fragments per promoter are generated.

Step 2: Heat kill endonucleases (65° C. for 15 minutes, 80° C. for 20 minutes for thermophilic but not thermostable endonucleases) and denature DNA (94° C. 1 minute). Add artificial templates (containing uracil, and from 3' side complementary to UniTaq Ai, and complementary to target DNA with Tm of about 72° C. to 5' side), upstream primers (containing 5' Universal Primer U1Pm, followed by UniTaq Ai), and thermostable ligase, and incubate at 60° C. to allow for hybridization and ligation of upstream primers to 5' phosphate of target DNA if and only if it was methylated and hybridized to the correct template.

Step 3: Add UNG and AP endonuclease, Hot-start Taq polymerase, dNTPs, Universal Primer UPm1, Universal Primer U2, and downstream primers (containing 5' Universal Primer U2, followed by UniTaq Bi, followed by target locus-specific sequence complementary to the target fragment with sequence that is just downstream of the artificial template strand sequence). Incubate at 37° C. for 30 minute to destroy artificial template strand, activate polymerase at 95° C. for 5 minutes, and then allow amplification to proceed for 8-20 cycles. Ideally, the universal primer tails U1Pm and U2 on the LDR and PCR compound primers are slightly shorter than Universal primers U1 and U2. This allows initial universal amplification at a lower cycling temperature (i.e. 55° C. annealing) followed by higher cycling temperature (i.e. 65° C. annealing) such that the universal primers U1Pm and U2 bind preferentially to the desired product (compared to composite primers binding to incorrect products). Further the universal primers U1Pm and U2 contain a short sequence in common (i.e. 6-10 bases) to avoid primer dimer formation. In an optional variation to minimize target independent amplifications, the downstream PCR primers contain a susceptible base and a blocked 3' end, which is liberated by an enzyme that cleaves the susceptible base when the primer is hybridized to its target. For example, the susceptible base may be an RNA nucleotide, with the cleavage enzyme being an RNaseH (See Dobosy et al. BMC Biotechnology 2011, 11:80), which is hereby incorporated by reference in its entirety). These conditions amplify products of the sequence:

Univ.Primer U1Pm-UniTaq Ai-Target DNA-UniTaq Bi'-Univ.Primer U2'

Step 4: dilute 10- to 100-fold and distribute aliquots to Taqman wells, each well containing the following primers: Universal Primer U2 and UniTaq specific primers of the format F1-UniTaq Bi-Q-UniTaq Ai. (where F1 is a fluorescent dye that is quenched by Quencher Q). Under these conditions, the following product will form:

F1-UniTaq Bi-Q-UniTaq Ai-Target DNA-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

Highly sensitive methylation detection may be performed using Zipcode array, Zipcode Taqman, or traditional Taqman detection as described supra. For example, the upstream primer need only contain a 5' Univ.Primer U1 followed by a zipcode sequence. The downstream primer need only contain 5' Univ.Primer U2 followed by target DNA. After universal PCR amplification, these conditions amplify fragments of the sequence:

Univ.Primer U1 Zipcode Zi-Target-DNA-Univ.Primer U2'

For detection using universal arrays containing capture oligonucleotides, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array containing capture oligonucleotides.

In an alternative approach, highly sensitive methylation detection may be performed using split Zipcode sequences. This approach would use upstream first oligonucleotide primers (5' Univ.Primer U1 followed by a first half zipcode sequence Ai and a short sequence Ci), and downstream second oligonucleotide primers (5' Univ.Primer U2 followed by a second half zipcode sequence Ai, the short sequence Ci, and target DNA). After universal PCR amplification, these conditions amplify fragments of the sequence:

Univ.Primer U1-$1^{st}$ ½ Zipcode Zi-Short Ci-Target-DNA-Short Ci'-$2^{nd}$ ½ Zipcode Zi-Univ.Primer U2'

When the Short Ci transiently hybridizes to Short Ci', the $1^{st}$ ½Zipcode Zi sequence is brought in proximity to the $2^{nd}$ ½ Zipcode Zi, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.

Univ.Primer U1-Unique Ai-$1^{st}$ ½ Zipcode Zi-Short Ci-Target DNA-Short Ci'-$2^{nd}$ ½ Zipcode Zi-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing.

Detailed Protocol: Detection of Highly Sensitivity Methylation Marker for Promoter Hypermethylation (Present at 1% to 0.01%) in Methyl Enriched DNA or Total Serum DNA (See FIG. 2B)

Overview of Approach:

Isolated genomic DNA, or methyl enriched DNA is treated with a cocktail of methyl sensitive enzymes (AciI, HinP1I, Hpy99I, HpyCH4IV, BstUI, HpaII, HhaI or a combination thereof), as well as by methyl insensitive enzymes (MspI, HaeIII, AluI, TaqI, HpyCH4V, HpyCH4III, BfaI, NlaIII, DdeI, BsaJI, or a combination thereof). The idea is to generate a fragment of DNA of approximately 40 bases or more, wherein the 5' phosphate of the fragment originated from a methyl insensitive enzyme. The fragment should have at least 3 methyl sensitive enzyme sites, such that cleavage would cause these fragments to dissipate. One strand of the genomic fragment is then hybridized onto an artificial template containing a hairpin, with and upstream region, which is unrelated to genomic DNA, and can ligate to the genomic fragment at the 5' phosphate. A downstream oligonucleotide that hybridizes to the genomic fragment downstream of where it hybridized to the template strand is added. When extending the locus-specific primer, the 5'→3' exonuclease activity of polymerase destroys the template portion of the ligated oligonucleotide, creating a product containing both upstream and downstream tags and suitable for amplification. Unligated hairpin oligonucleotide will extend on itself and not amplify further. Both upstream and downstream oligonucleotides have UniTaq specific sequences, a zipcode specific sequence, and universal sequences outside, allowing for simultaneous "preamplification" for 8-20 cycles, prior to opening tube, and dividing into the appropriate UniTaq taqman assays. For each promoter region, there will be three positions of interrogation, such that it can be seen when the signal appears (Ct value indicating relative quantity of methylated sequence) as well as total signal strength (i.e. =1, 2, or 3 sites methylated for that promoter).

To summarize the levels of discrimination of the above approach for detection of low-abundance methylation:
1. Use of methylation insensitive restriction enzyme to generate a unique 5' phosphate on double-stranded target DNA.
2. Use of methylation sensitive restriction enzymes to cleave double-stranded target when not methylated.
3. Use of ligation fidelity of thermostable ligase to ligate correct tag to target strand.
4. Use of locus specific primer and polymerase to amplify ligated target strands.
5. Use of sequences on the 3' end of tag oligonucleotides, such that when they are not ligated, form hairpins and extend on themselves to form products that do not amplify.

Step 1: Cleave isolated genomic DNA, or methyl enriched DNA with a cocktail of methyl sensitive enzymes (AciI, HinP1I, Hpy99I, HpyCH4IV, BstUI, HpaII, HhaI or a combination thereof), as well as by methyl insensitive enzymes (MspI, HaeIII, AluI, TaqI, HpyCH4V, HpyCH4III, BfaI, NlaIII, DdeI, BsaJI, or a combination thereof). Generate fragments of approximately 40 bases or more that have a 5' phosphate from a methylation insensitive site (i.e. MspI, HaeIII, AluI, TaqI, HpyCH4V, HpyCH4III, BfaI, NlaIII, DdeI, or BsaJI), and at least one methyl sensitive sites (that are not cleaved because they were methylated). Preferably, generate three such fragments per promoter. Heat kill endonucleases (65° C. for 15 minutes, 80° C. for 20 minutes if using thermophilic endonuclease) and denature DNA (94° C. 1 minute). Artificial templates contain upstream primer region (5' Universal Primer U1Pm, followed by UniTaq Ai) as well as a region complementary to UniTaq Ai, and a region complementary to target DNA with Tm of about 72° C.). Incubate at 60° C. to allow for hybridization and ligation of hairpinned oligonucleotides to 5' phosphate of target DNA if and only if it was methylated and hybridized to the correct template.

Step 2: Add Hot-start Taq polymerase, dNTPs, Universal Primer U1Pm, Universal Primer U2, and downstream primers (containing 5' Universal Primer U2, followed by UniTaq Bi, followed by target locus-specific sequence complementary to the target fragment with sequence that is just downstream of the artificial template strand sequence). When extending the locus-specific primer, the 5'→3' exonuclease activity of polymerase destroys the template portion of the ligated oligonucleotide, creating a product containing both upstream and downstream tags and suitable for amplification. Unligated hairpin oligonucleotide will extend on itself and not amplify further. Ideally, the universal primer tails U1Pm and U2 on the LDR and PCR compound primers are slightly shorter than Universal primers U1 and U2. This allows initial universal amplification at a lower cycling temperature (i.e. 55° C. annealing) followed by higher cycling temperature (i.e. 65° C. annealing) such that the universal primers U1Pm and U2 bind preferentially to the desired product (compared to composite primers binding to incorrect products). Further, the universal primers U1Pm and U2 contain a short sequence in common (i.e. 6-10 bases) to avoid primer dimer formation. In an optional variation to minimize target independent amplifications, the downstream PCR primers contain a uracil base and a blocked 3' end, which is liberated by an RNase-H that cleaves the uracil base when the primer is hybridized to its target. These conditions generate universal amplification products of the sequence: Univ.Primer U1Pm-UniTaq Ai-Target DNA-UniTaq Bi'-Univ.Primer U2'

Step 3: Open tube, dilute 10- to 100-fold and distribute aliquots to Taqman wells, each well containing the following primers: Universal Primer U2 and UniTaq specific primers of the format F1-UniTaq Bi-Q-UniTaq Ai (where F1 is a fluorescent dye that is quenched by Quencher Q). Under these conditions, the following secondary extension products will form:
F1-UniTaq Bi-Q-UniTaq Ai-Target DNA-UniTaq Bi'-Univ.Primer U2'
This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

As a control for the total amount of DNA present, one can choose a nearby target fragment where the 5' phosphate is generated by a methyl insensitive enzyme (HaeIII or MspI), and the rest of the fragment is lacking in methyl sensitive enzyme sites. The upstream oligonucleotide that is ligated to the target fragment is a mixture of two oligonucleotides: (i) An oligonucleotide present at 1 in 100 with the correct UniTaq specific sequence, and (ii) an oligonucleotide present at 99 in 100 with a sequence that has about 8-10 bases complementary to its 3' end. After the ligation event and destroying template with UNG and AP endonuclease, the universal primers are added for PCR amplification. The ligation product containing the UniTaq sequences amplifies and will give a signal equivalent to 1 in 100 of the original template. The majority ligation product lacks the universal sequence on the 5' end, and does not amplify exponentially. Unligated upstream primer will form a hairpin back on itself, and extend its own 3' sequence on itself, taking it out of contention for becoming part of another PCR amplicon. Alternatively or in addition, the control may use a different ratio of the two oligonucleotides, for example 1:10 or 1:1,000 to allow for accurate comparisons to low-levels of the methylated DNA present at the promoter site of interest. (Please see FIG. 3).

An alternative control uses a mixture of two oligonucleotides: (i) A hairpinned oligonucleotide present at 1 in 100 with the correct UniTaq specific sequence, and (ii) A hairpinned oligonucleotide present at 99 in 100 without the UniTaq sequence. After the ligation event, the universal primers are added for PCR amplification. When extending the locus-specific primer, the 5'→3' exonuclease activity of polymerase destroys the template portion of the ligated oligonucleotide, creating a product containing both upstream and downstream tags and suitable for amplification. Unligated hairpin oligonucleotide will extend on itself and not amplify further. The ligation product containing the UniTaq sequences amplifies and will give a signal equivalent to 1 in 100 of the original template. The majority ligation product lacks the universal sequence on the 5' end, and does not amplify exponentially. (Please see FIG. 4).

Highly sensitive methylation detection may be performed using Zipcode array, Zipcode Taqman, or traditional Taqman detection as described supra. For example, the upstream primer need only contain a 5' Univ.Primer U1 followed by a zipcode sequence. The downstream primer need only contain 5' Univ.Primer U2 followed by target DNA. After universal PCR amplification, these conditions amplify fragments of the sequence:
Univ.Primer U1-Zipcode Zi-Target-DNA-Univ.Primer U2'

For detection using universal arrays containing capture oligonucleotides, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array containing capture oligonucleotides.

In an alternative approach, highly sensitive methylation detection may be performed using split Zipcode sequences. This approach would use upstream first oligonucleotide primers (5' Univ.Primer U1 followed by a first half zipcode sequence Ai and a short sequence Ci), and downstream second oligonucleotide primers (5' Univ.Primer U2 followed by a second half zipcode sequence Ai, the short sequence Ci, and target DNA). After universal PCR amplification, these conditions amplify fragments of the sequence:
Univ.Primer U1-$1^{st}$ ½ Zipcode Zi-Short Ci-Target-DNA-Short Ci'-$2^{nd}$ ½ Zipcode Zi-Univ.Primer U2'

When the Short Ci transiently hybridizes to Short Ci', the $1^{st}$ ½ Zipcode Zi sequence is brought in proximity to the $2^{nd}$ ½ Zipcode Zi, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.

Univ.Primer U1-Unique Ai-$1^{st}$ ½ Zipcode Zi-Short Ci-Target DNA-Short Ci'-$2^{nd}$ ½ Zipcode Zi-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing.

Figure 10:
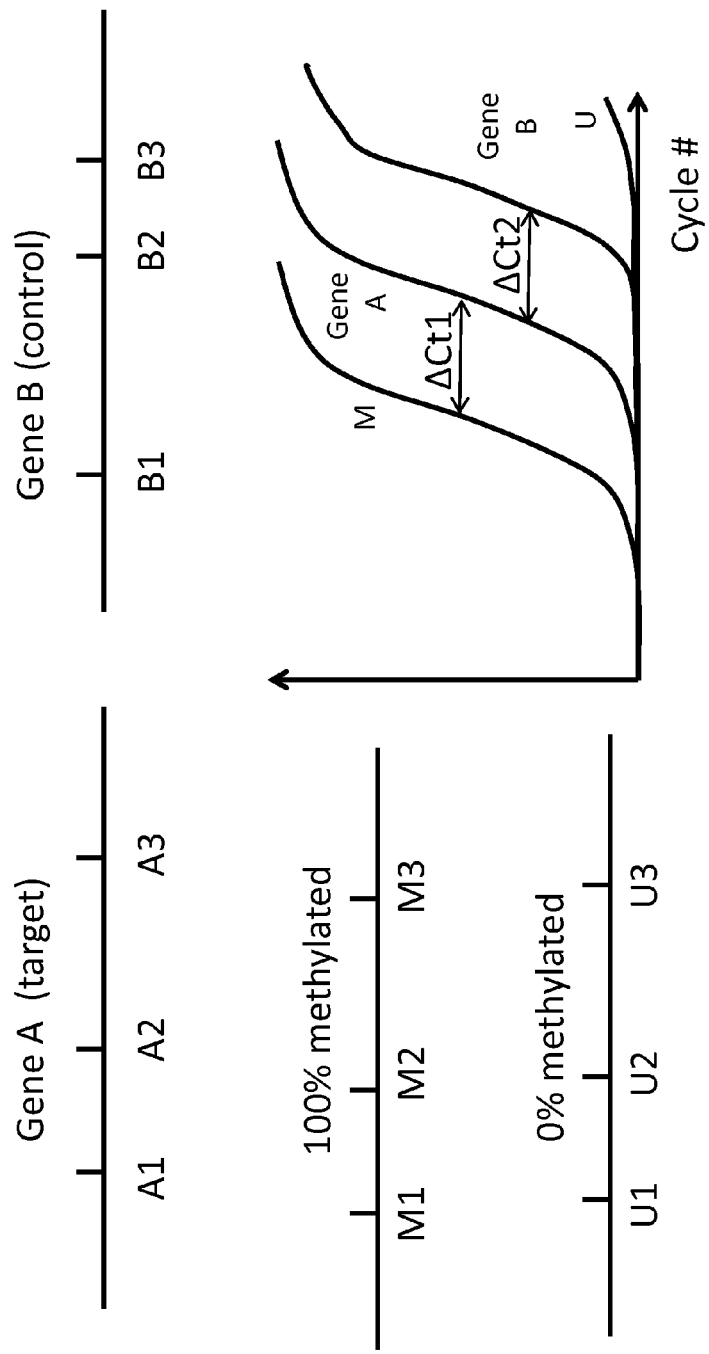
FIG. 10 shows how to combine signal from several methylation sites and normalize signal to a control gene. There may be several target and several control genes. Signal "M" is from fully methylated template. Signal "Gene A" is from methylation level of gene A. Signal "Gene B" is from methylation level of gene B (control). Signal "U" is from unmethylated template. ΔCt1 is used to estimate percentage methylation relative to 100% methylated; ΔCt2 measures differential methylation between the two genes. As described in FIGS. 3 and 4, using a mixture of amplification incompetent ligation primers with amplification competent ligation primers at ratios of 99:1 or 999:1 will provide a control signal that represents 1% or 0.1%, respectively, of starting total input DNA template. In this manner, low levels of methylated DNA in an excess of unmethylated DNA can be accurately quantified.

Fluorescent Labeling:

Consider an instrument that can detect 5 fluorescent signals, F1, F2, F3, F4, and F5, respectively. For each promoter region, there will be one, two, or three positions of interrogation, such that it can be seen when the signal appears (Ct value indicating relative quantity of methylated or unmethylated sequence) as well as total signal strength (i.e. =1, 2, or 3 sites methylated or unmethylated for that promoter). (Please see FIG. 10). To expand on this concept a bit further, the UniTaq reaction provides two types of signal, the Ct value and the end point, or total signal strength. During the universal amplification step (2.3c above, see also FIG. 5), the Universal Primer U2 is used in all the amplicons, and should be in excess, while each UniTaq specific primer F1-UniTaq Bi-Q-UniTaq Ai can be used to provide a specific signal strength. For example, consider that the scale is 1,000 FU (fluorescent units). By titrating both fluorescently labeled (F1-UniTaq Bi-Q-UniTaq Ai) and unlabeled primers (UniTaq Bi-Q-UniTaq Ai) of the same sequence, the end signal strength can be calibrated to a particular level, for example, 100FU. Consider the following 3 Gene Promoter Methylation, DNA quantification control, and unmethylated DNA controls, with an instrument that can detect 5 fluorescent signals, F1, F2, F3, F4, and F5, respectively. The potential products would be:
Gene 1 Promoter Methylation
F1-UniTaq B1-Q-UniTaq A1-Target DNA-UniTaq B1'-Univ.Primer U2'
F1-UniTaq B2-Q-UniTaq A2-Target DNA-UniTaq B2'-Univ.Primer U2'
F1-UniTaq B3-Q-UniTaq A3-Target DNA-UniTaq B3'-Univ.Primer U2'
Gene 2 Promoter Methylation
F2-UniTaq B4-Q-UniTaq A4-Target DNA-UniTaq B4'-Univ.Primer U2'
F2-UniTaq B5-Q-UniTaq A5-Target DNA-UniTaq B5'-Univ.Primer U2'
F2-UniTaq B6-Q-UniTaq A6-Target DNA-UniTaq B6'-Univ.Primer U2'
Gene 3 Promoter Methylation
F3-UniTaq B7-Q-UniTaq A7-Target DNA-UniTaq B7'-Univ.Primer U2'
F3-UniTaq B8-Q-UniTaq A8-Target DNA-UniTaq B8'-Univ.Primer U2'
F3-UniTaq B9-Q-UniTaq A9-Target DNA-UniTaq B9'-Univ.Primer U2'
DNA Quantification Control (1:100)
F4-UniTaq B10-Q-UniTaq A10-Target DNA-UniTaq B10'-Univ.Primer U2'
Unmethylated DNA Control
F5-UniTaq B11-Q-UniTaq A11-Target DNA-UniTaq B11'-Univ.Primer U2'

(Products without fluorescent labels are not shown for clarity. For each fluorescent product, in the next round of amplification, the Fluorescent group is cleaved off to create signal.)

In this example, a promoter is only counted as methylated if 2/3 or 3/3 signals are positive. Consider the following results after 45 cycles:

F1, Ct=31.5, final FU=220
F2, Ct=38.5, final FU=90
F3, Ct>45
F4, Ct=28.5, final FU=110
F5, Ct>45

The above result suggests that Gene 1 Promoter (F1 signal) is fully methylated in 2/3 of the fragments interrogated. With a ΔCt value of 3 compared to the 1:100 control, the methylated DNA is present at 1/800, or about 0.12%. This would be consistent with cfDNA arising from a tumor. The Gene 2 Promoter (F2) on the other hand gave some signal, suggesting that 1/3 fragments was methylated, but with a ΔCt value of 10 compared to the 1:100 control, the methylated DNA is present at 1/102,400, or about 0.0009%. This is probably at the limit of genome equivalents interrogated in the serum sample, and thus most likely represents stochastic methylation due to aging. The Gene 3 Promoter and the unmethylated controls gave no signal.

It is recognized that identifying a fragment of the desired length flanked by the appropriate restriction sites depends on the sequence of the particular promoter. Nevertheless, this approach is amenable to detecting low levels of unmethylated promoters, methylated promoters (analogous to scheme in FIG. 2B), as well as control amplifications analogous to the scheme in FIG. 4.

Prophetic Example 2—Detection of Highly Sensitivity Unmethylation Marker for Promoter Hypomethylation (Present at 1% to 0.01%)

The majority of methylation changes in tumors are due to hypomethylation. When such hypomethylation occurs in a promoter region that was previously methylated, it may cause increased expression of a gene, such as an oncogene. Further, repetitive element regions and mobile elements are generally silenced by overall methylation, but such silencing is lost when the tumor becomes hypomethylated.

Overview of Approach:

While methyl-sensitive restriction enzymes may be used to help selectively amplify and identify low levels of methylated sequences, the approach does not work for identifying low levels of unmethylated sequences. Bisulfite treatment and use of PCR primers directed to convert unmethylated DNA may be used, although such primers are very AT rich and there may be difficulty amplifying all desired fragments, especially when attempting multiplexed PCR.

The beauty of the restriction enzyme/LDR/PCR protocol described in Section 1 (above) is that it can be used directly to also look for unmethylated sequences. In this case, one needs fragments that are bounded on one side by a methyl sensitive enzyme, and then the fragment needs to be about 30-40 bases without any additional sites. (Please see FIGS. 1A and 2A and discussion in Section 1).

There is the chance that a given site is unmethylated, while other nearby sites are methylated. When scoring for just a single site to be unmethylated, it is required that at least 2 of 3 sites within the promoter region give signal, and generally an entire promoter region is either methylated or unmethylated.

One approach to improve the significance of scoring for unmethylated sites is to require both sides of a fragment to come from cleavage of unmethylated sites. Below is a scheme that requires ligation on both sides of an unmethylated fragment.

To summarize the levels of discrimination of the above double-site cleavage approach for detection of low-abundance unmethylated sites:

1. Use of methylation sensitive restriction enzymes to cleave double-stranded target when not methylated at both sites.
2. Use of ligation fidelity of thermostable ligase to ligate correct tags to target strand on both sides.
3. Use of uracil DNA glycosylase to destroy template strands.

Detailed Protocol for Highly Sensitive Detection of Promoter Unmethylation (Present at 1% to 0.01%) Using Two Sites (FIG. 8):

Step 1: Cleave isolated genomic DNA, or methyl enriched DNA with a cocktail of methyl sensitive enzymes (AciI, HinP1I, Hpy99I, HpyCH4IV, BstUI, HpaII, HhaI or a combination thereof). As an option, when simultaneously scoring for low-abundance methylated sites, methyl insensitive enzymes (MspI, HaeIII, AluI, TaqI, HpyCH4V, HpyCH4III, BfaI, NlaIII, DdeI, BsaJI, or a combination thereof) may be included in the cleavage reaction. Generate fragments of approximately 25-35 bases that have a 5' phosphate from an AciI, HinP1I, Hpy99I, HpyCH4IV, BstUI, HpaII, or HhaI site, and no additional methyl sensitive sites. Preferably, generate three such fragments per promoter. The mixture also contains downstream primers of the sequence UniTaq Bi'-Univ.Primer U2', where the 5' end either already contains a phosphate group, or alternatively is part of a restriction sequence that is cut by one of the restriction enzymes to properly unmask a 5' phosphate suitable for subsequent ligation. (This may be achieved by using a restriction site within a hairpin loop at the 5' end of the oligonucleotide.)

Step 2: Heat kill endonucleases (65° C. for 15 minutes) and denature DNA (94° C. 1 minute). Add artificial templates (containing uracil, and from 3' side complementary to UniTaq Ai, complementary to target DNA with a Tm of about 72° C., complementary to UniTaq Bi to 5' side), upstream primers (containing 5' Universal Primer U1, followed by UniTaq Ai), (downstream primers with liberated 5' ends will already be present) and thermostable ligase, and incubate at 60° C. to allow for hybridization and ligation of upstream primers to 5' phosphate of target DNA and downstream primer to the 3' OH end of the target DNA if and only if it was unmethylated on both sites, and hybridized to the correct template.

Step 3: Add UNG and AP endonuclease, Hot-start Taq polymerase, dNTPs, Universal Primer U1, Universal Primer U2. Incubate at 37° C. for 30 minute to destroy artificial template strand, activate polymerase at 95° C. for 5 minutes, and then allow amplification to proceed for 8-20 cycles. Ideally, the universal primer tails U1 and U2 on the ligation compound primers are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR primers binding to incorrect products). Further the universal primers U1 and U2 contain a short sequence in common (i.e. 6-10 bases) to avoid primer dimer formation. These universal PCR conditions amplify fragments of the sequence:
Univ.Primer U1-UniTaq Ai-Target DNA-UniTaq Bi'-Univ.Primer U2'

Step 4: dilute 10- to 100-fold and distribute aliquots to Taqman wells, each well containing the following primers: Universal Primer U2 and UniTaq specific primers of the format F1-UniTaq Bi-Q-UniTaq Ai. (where F1 is a fluorescent dye that is quenched by Quencher Q). Under these conditions, the following product will form:
F1-UniTaq Bi-Q-UniTaq Ai-Target DNA-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

Detailed Protocol for Highly Sensitive Detection of Promoter Unmethylation (Present at 1% to 0.01%) Using Two Sites (FIG. 9A):

A second variation would use both upstream and downstream hairpinned oligonucleotides. However, to be effective, the downstream hairpinned LDR primer would need to be activated after the restriction digestion. Use of Taq polymerase 5'→3' nuclease would not necessarily activate the 5' side of the target fragment without requiring a restriction digest. This can be avoided by having a mismatch between the fragment sequence (i.e. GCGC) and the target sequence (i.e. complementary target portion reads 3'→5' AGCG instead of CGCG). Unligated upstream hairpin oligonucleotides will extend on themselves and not amplify further. The downstream ligation oligonucleotide has a 5' tail that is cleaved off by the 5'→3' activity of Taq polymerase when hybridized to the cut fragment, but uncut tail hybridizes back to the Universal Primer U2' region such that it inhibits priming of the unligated oligonucleotide.

To summarize the levels of discrimination of the above double-site cleavage approach for detection of low-abundance unmethylated sites:
1. Use of methylation sensitive restriction enzymes to cleave double-stranded target when not methylated at both sites.
2. Use of ligation fidelity of thermostable ligase to ligate correct tags to target strand on both sides.
3. Use of 5'-3' nuclease activity of polymerase or Fen nuclease on downstream tag.

Step 1: Prepare mix containing restriction enzymes, artificial hairpinned templates (see below), optional Taq polymerase (see below), and thermostable ligase. Cleave isolated genomic DNA, or methyl enriched DNA with a cocktail of methyl sensitive enzymes (AciI, HinP1I, Hpy99I, HpyCH4IV, BstUI, HpaII, HhaI or a combination thereof). As an option, when simultaneously scoring for low-abundance methylated sites, methyl insensitive enzymes (MspI, HaeIII, AluI, TaqI, HpyCH4V, HpyCH4III, BfaI, NlaIII, DdeI, BsaJI, or a combination thereof) may be included in the cleavage reaction. Generate fragments of approximately 40 bases that have a 5' phosphate from an AciI, HinP1I, Hpy99I, HpyCH4IV, BstUI, HpaII, or HhaI site, and no additional methyl sensitive sites. Preferably, generate three such fragments per promoter. Heat kill endonucleases (65° C. for 15 minutes, or 80° C. for 20 minutes when using thermophilic enzymes) and denature DNA (94° C. 1 minute). Artificial templates contain upstream primer region (5' Universal Primer U1, followed by UniTaq Ai) as well as a region complementary to UniTaq Ai, and a region complementary to target DNA with Tm of about 72° C.). Artificial templates contain downstream primer region (UniTaqBi' followed by Universal Primer U2') as well as a region complementary to UniTaq Bi', and a region complementary to target DNA with Tm of about 72° C.). In the preferred variation, the downstream ligation oligonucleotide has a 5' tail that is cleaved off by the 5'→3' activity of Taq polymerase when hybridized to the cut fragment, but uncut tail hybridizes back to the Universal Primer U2' region such that it inhibits priming of the unligated oligonucleotide. Incubate at 60° C. to allow for hybridization, cleavage, and ligation of hairpinned oligonucleotides to 5' phosphate and 3' OH of target DNA if and only if it was unmethylated at both restriction sites, and hybridized to the correct template.

Step 2: Add Hot-start or regular dNTPs, Universal Primer U1, and Universal Primer U2. When extending with Universal Primer U2, the 5'→3' exonuclease activity of polymerase destroys the template portion of both ligated oligonucleotides, creating a product containing both upstream and downstream tags and suitable for amplification. Unligated upstream hairpin oligonucleotides will extend on themselves and not amplify further. Ideally, the universal primer tails U1 and U2 on the hairpinned primers are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite primers binding to incorrect products). Further the universal primers U1 and U2 contain a short sequence in common (i.e. 6-10 bases) to avoid primer dimer formation. These universal PCR conditions amplify fragments of the sequence:
Univ.Primer U1-UniTaq Ai-Target DNA-UniTaq Bi'-Univ.Primer U2'

Step 4: dilute 10- to 100-fold and distribute aliquots to Taqman wells, each well containing the following primers: Universal Primer U2 and UniTaq specific primers of the format F1-UniTaq Bi-Q-UniTaq Ai. (where F1 is a fluorescent dye that is quenched by Quencher Q). Under these conditions, the following product will form:
F1-UniTaq Bi-Q-UniTaq Ai-Target DNA-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

Detailed Protocol for Highly Sensitive Detection of Promoter Methylation or Unmethylation (Present at 1% to 0.01%) Using Two Sites and Tethered Probes (FIG. 9B):

The above approach can also be extended to detect low abundance methylation as well. Further, the concept of using ligation on both sides may be extended in a general sense by tethering the two artificial hairpinned templates to each other so they form a single template for the fragment. The advantage of using a tethered design is that now correctly cleaved target need hybridize to only a single artificial template, and this allows use of lower concentration oligonucleotides. The artificial template has within it a link or spacer region that would block polymerase extending the 3' end of unligated hairpin all the way across the template so that it can't ligate to itself in the absence of target, but not interfere with the 5'-3' nuclease activity of polymerase when extending Univ.Primer U2 to destroy the artificial template strand of a properly ligated target.

Step 1: Prepare mix containing restriction enzymes, artificial hairpinned templates (see below), optional Taq polymerase (see below), and thermostable ligase. (i) For high sensitivity detection of methylated DNA, cleave isolated genomic DNA, or methyl enriched DNA with a cocktail of methyl sensitive enzymes (AciI, HinP1I, Hpy99I, HpyCH4IV, BstUI, HpaII, HhaI or a combination thereof), as well as by methyl insensitive enzymes (MspI, HaeIII, AluI, TaqI, HpyCH4V, HpyCH4III, BfaI, NlaIII, DdeI, BsaJI, or a combination thereof). Generate fragments of approximately 20-40 bases or more that have a 5' phosphate from a MspI, HaeIII, AluI, TaqI, HpyCH4V, HpyCH4III, BfaI, NlaIII, DdeI, or BsaJI site, and at least one methyl sensitive site(s) (that is/are not cleaved because they were methylated). Preferably, generate three such fragments per promoter. (ii) For high sensitivity detection of unmethylated DNA, cleave isolated genomic DNA with a cocktail of methyl sensitive enzymes (AciI, HinP1I, Hpy99I, HpyCH4IV, BstUI, HpaII, HhaI or a combination thereof). Optionally, if also detecting low-abundance methylated target, include methyl insensitive enzymes (MspI, HaeIII, AluI, TaqI, HpyCH4V, HpyCH4III, BfaI, NlaIII, DdeI, BsaJI, or a combination thereof). Generate fragments of approximately 20-40 bases or more that have a 5' phosphate from an AciI, HinP1I, Hpy99I, HpyCH4IV, BstUI, HpaII, or HhaI site, and no additional methyl sensitive sites. Preferably, generate three such fragments per promoter. Heat kill endonucleases (65° C. for 15 minutes) and denature DNA (94° C. 1 minute). Artificial templates contain upstream primer region (5' Universal Primer U1, followed by UniTaq Ai) as well as a region complementary to UniTaq Ai, and a region complementary to target DNA, a spacer or nucleotide analogue that terminates polymerase extension, a region complementary to target DNA, a region complementary to UniTaq Bi', Universal Primer U2', followed by UniTaqBi'. Artificial template is not cleaved by restriction enzymes by using: (i) 5-methyl C in the template, and/or (ii) altering the sequence at the ligation junctions so they are not recognized by the restriction enzyme. In the preferred variation, the downstream portion of the tethered ligation oligonucleotide has a 5' tail that is cleaved off by the 5'→3' activity of Taq polymerase when hybridized to the cut fragment, but uncut tail hybridizes back to the Universal Primer U2' region such that it inhibits priming of the unligated oligonucleotide. Incubate at 60° C. to allow for hybridization, cleavage, and ligation of tethered hairpinned oligonucleotides to 5' phosphate and 3' OH of target DNA if and only if it was either methylated (using enzymes as in (i)) or unmethylated (using enzymes as in (ii)) at both restriction sites, and hybridized to the correct template.

Step 2: Add Hot-start or regular dNTPs, Universal Primer U1, and Universal Primer U2. When extending with Universal Primer U2, the 5'→3' exonuclease activity of polymerase destroys the template portion of the ligated oligonucleotide, creating a product containing both upstream and downstream tags and suitable for amplification. The upstream hairpin of unligated oligonucleotides will extend on themselves until they reach the spacer or blocking region in the template, and not amplify further. Ideally, the universal primer tails U1 and U2 on the hairpinned oligonucleotides are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite primers binding to incorrect products). Further the universal primers U1 and U2 contain a short sequence in common (i.e. 6-10 bases) to avoid primer dimer formation. These universal PCR conditions amplify fragments of the sequence:
Univ.Primer U1-UniTaq Ai-Target DNA-UniTaq Bi'-Univ.Primer U2'

Step 4: dilute 10- to 100-fold and distribute aliquots to Taqman wells, each well containing the following primers: Universal Primer U2 and UniTaq specific primers of the format F1-UniTaq Bi-Q-UniTaq Ai. (where F1 is a fluorescent dye that is quenched by Quencher Q). Under these conditions, the following product will form:
F1-UniTaq Bi-Q-UniTaq Ai-Target DNA-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

Highly sensitive unmethylation or methylation detection may be performed using Zipcode array, Zipcode Taqman or traditional Taqman detection as described supra. For example, the upstream primer need only contain a 5' Univ.Primer U1 followed by a zipcode sequence. The downstream primer need only contain 5' Univ.Primer U2 followed by target DNA. After universal PCR amplification, these conditions amplify fragments of the sequence:
Univ.Primer U1-Zipcode Zi-Target-DNA-Univ.Primer U2'

For detection using universal arrays containing capture oligonucleotides, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array containing capture oligonucleotides.

In an alternative approach, highly sensitive methylation detection may be performed using split Zipcode sequences. This approach would use upstream first oligonucleotide primers (5' Univ.Primer U1 followed by a first half zipcode sequence Ai and a short sequence Ci), and downstream second oligonucleotide primers (5' Univ.Primer U2 followed by a second half zipcode sequence Ai, the short sequence Ci, and target DNA). After universal PCR amplification, these conditions amplify fragments of the sequence:
Univ.Primer U1-$1^{st}$ ½ Zipcode Zi-Short Ci-Target-DNA-Short Ci'-$2^{nd}$ ½ Zipcode Zi-Univ.Primer U2'

When the Short Ci transiently hybridizes to Short Ci', the $1^{st}$ ½ Zipcode Zi sequence is brought in proximity to the $2^{nd}$ ½ Zipcode Zi, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.
Univ.Primer U1 Unique Ai-$1^{st}$ ½ Zipcode Zi-Short Ci-Target DNA-Short Ci'-$2^{nd}$ ½ Zipcode Zi-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing.

Although the invention has been described in detail for the purpose of illustration, it is understood that such details are solely for that purpose and variations can be made therein by those skilled in the art without departing from the spirit and scope of the invention which is defined by the following claims.

What is claimed is:

1. A method for identifying, in a sample, one or more target nucleic acid molecules differing from other nucleic acid molecules in the sample by one or more methylated residues, said method comprising:
   providing a sample containing one or more target nucleic acid molecules potentially containing one or more methylated residues;
   subjecting the one or more target nucleic acid molecules in the sample to at least one methylation insensitive enzyme digestion reaction and at least one methylation sensitive enzyme digestion reaction to form a plurality of digestion products;
   providing a plurality of oligonucleotide adapters, each oligonucleotide adapter comprising a first primer-specific portion and a 3' end, said 3' end being configured to ligate to a 5' portion of a digestion product and hybridized to its complement, wherein the complement of the 3' end is coupled to a region complementary to a 5' portion of a digestion product;
   subjecting the digestion products to a ligation reaction comprising a denaturation treatment to form single-stranded digestion products, a hybridization treatment, wherein the single-stranded digestion products hybridize to their complementary region of the oligonucleotide adapters in a sequence-specific manner such that the 3' end of the adapter is adjacent to the 5'end of the single-stranded digestion product, and ligation treatment, wherein the oligonucleotide adapters ligate to their hybridized single-stranded digestion products thereby forming adapter tagged digestion products;
   providing one or more primary oligonucleotide primer sets, each primary primer set comprising (i) a first primary oligonucleotide primer comprising a nucleotide sequence that is the same as the first primer specific portion of the adapter tagged digestion products and (ii) a second primary oligonucleotide primer comprising a nucleotide sequence that is complementary to a region of the digestion product that is 3' to one or more methylated, uncleaved restriction sites, and a second primer-specific portion;
   blending the plurality of adapter tagged digestion products, the one or more primary oligonucleotide primer sets, and a first polymerase to form a first polymerase chain reaction mixture;
   subjecting the first polymerase chain reaction mixture to one or more polymerase chain reaction cycles comprising a denaturation treatment, a hybridization treatment, and an extension treatment thereby forming primary extension products; and
   detecting and distinguishing the primary extension products, thereby identifying the presence of one or more target nucleic acid molecules differing from other nucleic acid molecules in the sample by one or more methylated residues.

2. The method of claim 1, wherein each complement of the 3' end coupled to the region complementary to the 5' portion of the digestion product is a uracil containing oligonucleotide.

3. The method of claim 1, wherein the first primer specific portion and the complement of the 3' end of each oligonucleotide adapter are coupled to permit said oligonucleotide adapter to form a hairpin.

4. The method of claim 1, wherein the methylation insensitive digestion reaction is carried out using one or more restriction endonuclease enzymes selected from the group consisting of MspI, HaeIII, AluI, TaqI, HpyCH4V, HpyCH4III, BfaI, NlaIII, DdeI, BsaJI, and combinations thereof.

5. The method of claim 1, wherein the methylation sensitive digestion reaction is carried out using one or more restriction endonuclease enzymes selected from the group consisting of AciI, HinP1I, Hpy99I, HpyCH4IV, BstUI, HpaII, HhaI, and combinations thereof.

6. The method of claim 1, wherein one of the first or second oligonucleotide primers of an oligonucleotide primer set comprises a detectable label, whereby said detecting involves detection of labeled primary extension products.

7. The method of claim 1, wherein the oligonucleotide adapters further comprise a zip-code portion, wherein the zip-code portions hybridize to complementary capture oligonucleotides of a collection of capture oligonucleotides under uniform hybridization conditions.

8. The method of claim 1, wherein the second primary oligonucleotide primer of the primary oligonucleotide primer set further comprises an oligonucleotide detection portion, thereby forming primary extension products comprising the first primer-specific portion, the target-specific portions, the oligonucleotide detection portion, and the second primer-specific portion, said method further comprising:
   providing one or more detection probes, wherein each detection probe comprises a nucleotide sequence that is complementary to the oligonucleotide detection portion, a quencher moiety, and a detectable label, where the quencher moiety and the detectable label are separated from each other;
   providing one or more secondary oligonucleotide primer sets comprising a first secondary oligonucleotide primer and a second secondary oligonucleotide primer, said first and second secondary oligonucleotide primers capable of hybridizing to the primary extension products;
   blending the one or more detection probes, the one or more secondary oligonucleotide primer sets, the primary extension products, and a polymerase to form a second polymerase chain reaction mixture;
   subjecting the second polymerase chain reaction mixture to one or more polymerase chain reaction cycles comprising (i) a denaturation treatment, (ii) a hybridization treatment, wherein the one or more detection probes hybridize to their complementary oligonucleotide detection portions of the primary extension products, and the secondary oligonucleotide primers hybridize to the primary extension products, and (iii) an extension treatment, wherein the hybridized secondary oligonucleotide primers are extended thereby forming secondary extension products; and
   cleaving the quencher moiety and/or the detectable label from the one or more hybridized detection probes during said extension treatment, whereby said detecting involves the detection of the detectable label separated from the quencher moiety.

9. The method of claim 1, wherein (i) the second primary oligonucleotide primer of the primary oligonucleotide primer set further comprises an oligonucleotide detection portion, thereby forming primary extension products comprising the first primer-specific portion, the target-specific portions, the oligonucleotide detection portion, and the second primer-specific portion, said method further comprising:
    providing one or more secondary oligonucleotide primer sets comprising (i) a first secondary oligonucleotide primer having (a) a nucleotide sequence that is the same as a portion of the first primer-specific portion of the oligonucleotide adapter, (b) a detection probe comprising a nucleotide sequence that is the same as the oligonucleotide detection portion nucleotide sequence of the second primary oligonucleotide primer, (c) a quencher moiety and a detectable label separated by said detection probe, and (ii) a second secondary oligonucleotide primer having the same nucleotide sequence as a portion of the second primer-specific portion of the second primary oligonucleotide primer;
    blending the primary extension products, the one or more secondary oligonucleotide primer sets, and a polymerase to form a second polymerase chain reaction mixture;
    subjecting the second polymerase chain reaction mixture to one or more polymerase chain reaction cycles thereby forming secondary extension products; and
    subjecting the secondary extension products to conditions effective for the detection probe of the secondary extension products to hybridize to its complementary oligonucleotide detection portion, thereby forming hairpinned secondary extension products;
    cleaving the quencher moiety or the detectable label of the hairpinned secondary extension products, whereby said detecting involves the detection of the detectable label separated from the quencher moiety.

10. A method for identifying, in a sample, one or more target nucleic acid molecules differing from other nucleic acid molecules in the sample by one or more unmethylated residues, said method comprising:
    providing a sample containing one or more target nucleic acid molecules potentially containing one or more unmethylated residues;
    subjecting the one or more target nucleic acid molecules in the sample to a methylation sensitive enzyme digestion that digests unmethylated, but not methylated nucleic acid molecules to form a plurality of digestion products comprising one or more unmethylated residues;
    providing a plurality of oligonucleotide adapter sets, each oligonucleotide adapter set comprising (a) a first oligonucleotide adapter having a 3' end configured to ligate to a 5' end of a digestion product and hybridized to its complement, wherein the complement of the 3' end is coupled to a region complementary to a 5' portion of a digestion product, and (b) a second oligonucleotide adapter having a 5' end configured to ligate to a 3' end of a digestion product and hybridized to its complement, wherein the complement of the 5' end is coupled to a region complementary to a 3' portion of a digestion product;
    subjecting the digestion products to a ligation reaction comprising a denaturation treatment to form single-stranded digestion products, a hybridization treatment, wherein the single-stranded digestion products hybridize to their complementary regions of the first and second oligonucleotide adapters of an oligonucleotide adapter set in a sequence-specific manner such that the 3' end of the first adapter is adjacent to the 5' end of the single-stranded digestion product and the 5' end of the second adapter is adjacent to the 3' end of the single-stranded digestion product, and a ligation treatment, wherein the oligonucleotide adapters ligate to their hybridized single-stranded digestion products thereby forming dual adapter tagged digestion products; and
    detecting dual adapter tagged digestion products, thereby identifying one or more target nucleic acid molecules differing from other nucleic acid molecules in the sample by one or more unmethylated residues.

11. The method of claim 10, wherein one of the oligonucleotide adapters of the oligonucleotide adapter set comprises a detectable label.

12. The method of claim 10, wherein each complement of the 3' end of the first oligonucleotide adapter coupled to the region complementary to the 5' portion of the digestion product and each complement of the 5' end of the second oligonucleotide adapter coupled to the region complementary to the 3' portion of the digestion product is a uracil containing oligonucleotide.

13. The method of claim 10, wherein the 3' end and the complement of the 3' end of the first oligonucleotide adapter are coupled to permit said first oligonucleotide adapter to form a hairpin, and wherein the 5' end and the complement of the 5' end of the second oligonucleotide adapter are coupled to permit the second oligonucleotide adapter to form a hairpin.

14. The method of claim 13, wherein the second oligonucleotide adapter of an adapter set further comprises a 5' oligonucleotide flap portion containing a nucleotide sequence that is complementary to a 3' region of the second oligonucleotide adapter, wherein said 5' oligonucleotide flap portion is cleaved prior to said ligation treatment.

15. The method of claim 10, wherein the methylation sensitive digestion reaction is carried out using one or more restriction endonuclease enzymes selected from the group consisting of AciI, HinP1I, Hpy99I, HpyCH4IV, BstUI, HpaII, HhaI, and combinations thereof.

16. The method of claim 10, wherein the first oligonucleotide adapter of an oligonucleotide adapter set further comprises a first primer-specific portion coupled to the 3' end and the second oligonucleotide adapter of the oligonucleotide adapter set comprises a second primer-specific portion coupled to the 5' end, said dual adapter tagged digestion products comprising the first primer specific portion, the digestion product, and the second primer-specific portion, said method further comprising:
    providing one or more primary oligonucleotide primer sets, each primary primer set comprising (i) a first oligonucleotide primer having a nucleotide sequence that is the same as the first primer-specific portion of the dual adapter tagged digestion products and (ii) a second oligonucleotide primer having a nucleotide sequence that is complementary to the second primer-specific portion of the dual adapter tagged digestion products;
    blending the plurality of dual adapter tagged digestion products, the one or more primary oligonucleotide primer sets, and a first polymerase to form a first polymerase chain reaction mixture; and
    subjecting the first polymerase chain reaction mixture to one or more polymerase chain reaction cycles comprising a denaturation treatment, a hybridization treatment, and an extension treatment thereby forming primary extension products, whereby said detecting involves detection of the primary extension products.

17. The method of claim 16, wherein one of the first or second oligonucleotide primers of an oligonucleotide primer set comprises a detectable label, whereby said detecting involves detection of labeled primary extension products.

18. The method of claim 16, wherein one or both of the oligonucleotide adapters of an oligonucleotide adapter set further comprise a zip-code portion, wherein the zip-code portions hybridize to complementary capture oligonucleotides of a collection of capture oligonucleotides under uniform hybridization conditions.

19. The method of claim 16, wherein the second oligonucleotide adapter of an oligonucleotide adapter set further comprises an oligonucleotide detection portion, said method further comprising:
   providing one or more detection probes, wherein each detection probe comprises a nucleotide sequence that is complementary to said oligonucleotide detection portion of a dual adapter tagged digestion product, a quencher moiety, and a detectable label, where said quencher moiety and detectable label are separated from each other;
   adding the one or more detection probes to the first polymerase chain reaction mixture; and
   hybridizing the one or more detection probes to their complementary oligonucleotide detection portions of the dual adapter tagged digestion products or complements thereof during said subjecting, whereby the quencher moiety and/or the detectable label are cleaved from the hybridized detection probe during said extension treatment, whereby said detecting involves the detection of the detectable label separated from the quencher moiety.

20. The method of claim 16, wherein the second oligonucleotide adapter of an oligonucleotide adapter set further comprises an oligonucleotide detection portion, thereby forming primary extension products comprising the first primer-specific portion, the digestion product, the oligonucleotide detection portion, and the second primer-specific portion, said method further comprising:
   providing one or more detection probes, wherein each detection probe comprises a nucleotides sequence that is complementary to an oligonucleotide detection portion, a quencher moiety, and a detectable label, where the quencher moiety and the detectable label are separated from each other;
   providing one or more secondary oligonucleotide primer sets comprising a first secondary oligonucleotide primer and a second secondary oligonucleotide primer, said first and second secondary oligonucleotide primers capable of hybridizing to the primary extension products;
   blending the one or more detection probes, the one or more secondary oligonucleotide primer sets, the primary extension products, and a polymerase to form a second polymerase chain reaction mixture;
   subjecting the second polymerase chain reaction mixture to one or more polymerase chain reaction cycles comprising (i) a denaturation treatment, (ii) a hybridization treatment, wherein the one or more detection probes hybridize to complementary oligonucleotide detection portions of the primary extension products, and the secondary oligonucleotide primers hybridize to the primary extension products, and (iii) an extension treatment, wherein the hybridized secondary oligonucleotide primers are extended thereby forming secondary extension products; and
   cleaving the quencher moiety and/or the detectable label from the one or more hybridized detection probes during said extension treatment, whereby said detecting involves the detection of the detectable label separated from the quencher moiety.

21. The method of claim 16, wherein (i) the second oligonucleotide adapter of an oligonucleotide adapter set further comprises an oligonucleotide detection portion, thereby forming dual adapter tagged digestion products comprising the first primer-specific portion, the digestion product, the oligonucleotide detection portion, and the second primer-specific portion, (ii) the first oligonucleotide primer of the primary oligonucleotide primer set further comprises a detection probe comprising a nucleotide sequence that is complementary to the oligonucleotide detection portion of the ligated product sequence, a quencher moiety, and a detectable label, where the quencher moiety and the detectable label are separated by said detection probe, and (iii) the primary extension products formed during said subjecting comprise the detectable label, the oligonucleotide detection probe, the quencher moiety, the first primer-specific portion, the digestion product, the oligonucleotide detection portion, and the second primer-specific portion, said method further comprising:
   subjecting primary extension products to conditions effective for the detection probe of a particular primary extension product to hybridize to its complementary oligonucleotide detection portion, thereby forming hairpinned primary extension products; and
   cleaving the quencher moiety or the detectable label from the detection probe of the hairpinned primary extension product, whereby said detecting involves detection of the detectable label separated from the quencher moiety.

22. The method of claim 16, wherein (i) the second oligonucleotide adapter of an oligonucleotide adapter set further comprises an oligonucleotide detection portion, thereby forming primary extension products comprising the first primer-specific portion, the digestion product, the oligonucleotide detection portion, and the second primer-specific portion, said method further comprising:
   providing one or more secondary oligonucleotide primer sets comprising (i) a first secondary oligonucleotide primer having (a) a nucleotide sequence that is the same as a portion of the first primer-specific portion of the first oligonucleotide adapter, (b) a detection probe comprising a nucleotide sequence that is the same as the oligonucleotide detection portion nucleotide sequence of the second oligonucleotide adapter, (c) a quencher moiety and a detectable label separated by said detection probe, and (ii) a second secondary oligonucleotide primer having the same nucleotide sequence as the second primer-specific portion of the second oligonucleotide adapter;
   blending the primary extension products, the one or more secondary oligonucleotide primer sets, and a polymerase to form a second polymerase chain reaction mixture;
   subjecting the second polymerase chain reaction mixture to one or more polymerase chain reaction cycles thereby forming secondary extension products;
   subjecting the secondary extension products to conditions effective for the detection probe of particular secondary extension products to hybridize to its complementary oligonucleotide detection portion, thereby forming a hairpinned secondary extension product; and
   cleaving the quencher moiety or the detectable label of the hairpinned secondary extension products, whereby said detecting involves detection of the detectable label separated from the quencher moiety.

23. A method for identifying, in a sample, one or more target nucleic acid molecules differing from other nucleic acid molecules in the sample by one or more unmethylated residues, said method comprising:
providing a sample containing one or more target nucleic acid molecules potentially containing one or more unmethylated residues;
subjecting the one or more target nucleic acid molecules in the sample to at least one methylation sensitive enzyme digestion reaction to form a plurality of digestion products comprising one or more unmethylated residues;
providing a plurality of oligonucleotide adapters, each oligonucleotide adapter comprising a first primer-specific portion and a 3' end, said 3' end being configured to ligate to a 5' portion of a digestion product and hybridized to its complement, wherein the complement of the 3' end is coupled to a region complementary to a 5' portion of a digestion product;
subjecting the digestion products to a ligation reaction comprising a denaturation treatment to form single-stranded digestion products, a hybridization treatment, wherein the single-stranded digestion products hybridize to their complementary region of the oligonucleotide adapters in a sequence-specific manner such that the 3' end of the adapter is adjacent to the 5'end of the single-stranded digestion product, and ligation treatment, wherein the oligonucleotide adapters ligate to their hybridized single-stranded digestion products thereby forming adapter tagged digestion products;
providing one or more primary oligonucleotide primer sets, each primary primer set comprising (i) a first primary oligonucleotide primer comprising a nucleotide sequence that is the same as the first primer specific portion of the adapter tagged digestion products and (ii) a second primary oligonucleotide primer comprising a nucleotide sequence that is complementary to a region of the digestion product portion of the adapter tagged digestion product, and a second primer-specific portion;
blending the plurality of adapter tagged digestion products, the one or more primary oligonucleotide primer sets, and a first polymerase to form a first polymerase chain reaction mixture;
subjecting the first polymerase chain reaction mixture to one or more polymerase chain reaction cycles comprising a denaturation treatment, a hybridization treatment, and an extension treatment thereby forming primary extension products; and
detecting and distinguishing the primary extension products, thereby identifying the presence of one or more target nucleic acid molecules differing from other nucleic acid molecules in the sample by one or more unmethylated residues.

24. A method for identifying, in a sample, one or more target nucleic acid molecules differing from other nucleic acid molecules in the sample by one or more methylated residues, said method comprising:
providing a sample containing one or more target nucleic acid molecules potentially containing one or more methylated residues;
subjecting the one or more target nucleic acid molecules in the sample to at least one methylation insensitive enzyme digestion reaction and at least one methylation sensitive enzyme digestion reaction to form a plurality of digestion products comprising one or more methylated uncleaved restriction sites;
providing a plurality of oligonucleotide adapter sets, each oligonucleotide adapter set comprising (a) a first oligonucleotide adapter having a 3' end configured to ligate to a 5' end of a digestion product and hybridized to its complement, wherein the complement of the 3' end is coupled to a region complementary to a 5' portion of an digestion product, and (b) a second oligonucleotide adapter having a 5' end configured to ligate to a 3' end of a digestion product and hybridized to its complement, wherein the complement of the 5' end is coupled to a region complementary to a 3' portion of a digestion product;
subjecting the digestion products to a ligation reaction comprising a denaturation treatment to form single-stranded digestion products, a hybridization treatment, wherein the single-stranded digestion products hybridize to their complementary regions of the first and second oligonucleotide adapters of an oligonucleotide adapter set in a sequence-specific manner such that the 3' end of the first adapter is adjacent to the 5'end of the single-stranded digestion product and the 5' end of the second adapter is adjacent to the 3' end of the single-stranded digestion product, and a ligation treatment, wherein the oligonucleotide adapters ligate to their hybridized single-stranded digestion products thereby forming dual adapter tagged digestion products; and
detecting dual adapter tagged digestion products, thereby identifying one or more target nucleic acid molecules differing from other nucleic acid molecules in the sample by one or more methylated residues.

25. The method of claim 24, wherein the methylation insensitive digestion reaction is carried out using one or more restriction endonuclease enzymes selected from the group consisting of MspI, HaeIII, AluI, TaqI, HpyCH4V, HpyCH4III, BfaI, NlaIII, DdeI, BsaJI, and combinations thereof.

* * * * *